(12) United States Patent
Wahlberg

(10) Patent No.: US 10,364,280 B2
(45) Date of Patent: Jul. 30, 2019

(54) POLYPEPTIDE

(71) Applicant: AFFIBODY AB, Solna (SE)

(72) Inventor: Elisabet Wahlberg, Sigtuna (SE)

(73) Assignee: AFFIBODY AB, Solna (SE)

(*) Notice: Subject to any disclaimer, the term of this patent is extended or adjusted under 35 U.S.C. 154(b) by 0 days.

(21) Appl. No.: 15/767,801

(22) PCT Filed: Oct. 28, 2016

(86) PCT No.: PCT/EP2016/076027
§ 371 (c)(1),
(2) Date: Apr. 12, 2018

(87) PCT Pub. No.: WO2017/072273
PCT Pub. Date: May 4, 2017

(65) Prior Publication Data
US 2018/0305437 A1 Oct. 25, 2018

(30) Foreign Application Priority Data

Oct. 30, 2015 (EP) .................................. 15192367
Feb. 24, 2016 (EP) .................................. 16157190

(51) Int. Cl.
*A61K 38/17* (2006.01)
*A61P 31/18* (2006.01)
*A61P 31/20* (2006.01)
*A61P 35/02* (2006.01)
*C07K 14/705* (2006.01)
*C07K 14/745* (2006.01)

(52) U.S. Cl.
CPC ...... *C07K 14/70532* (2013.01); *C07K 14/745* (2013.01); *A61K 38/1774* (2013.01); *A61P 31/18* (2018.01); *A61P 31/20* (2018.01); *A61P 35/02* (2018.01); *C07K 2319/00* (2013.01)

(58) Field of Classification Search
CPC .......................... A61K 38/1709; A61K 47/551
See application file for complete search history.

(56) References Cited

U.S. PATENT DOCUMENTS 5,595,756 A * 1/1997 Bally .................. A61K 9/1272
264/4.1
2018/0312565 A1 11/2018 Wahlberg et al.

FOREIGN PATENT DOCUMENTS

| CN | 103304638 A | 9/2013 |
| CN | 103936835 A | 7/2014 |
| CN | 104086627 A | 10/2014 |
| CN | 104761633 A | 7/2015 |
| WO | 2009089149 A1 | 7/2009 |
| WO | 2014140366 A1 | 9/2014 |
| WO | 2015095418 A1 | 6/2015 |
| WO | 2017072280 A1 | 5/2017 |

OTHER PUBLICATIONS

Sporn et at, "Chemoprevention of Cancer," Carcinogenesis, vol. 21 (2000), 525-530 (Year: 2000).*
Aggarwal, et al, Models for prevention and treatment of cancer: problems v promises, Biochemical Pharmacology 78 (2009) 1083-1094 (Year: 2009).*
Gura, "Cancer Models: Systems for Identifying New Drugs Are Often Faulty," Science vol. 278 (1997), 1041-1042 (Year: 1997).*
Fan Wang et al., "Synthetic small peptides acting on B7H1 enhance apoptosis in pancreatic caner cells", Molecular Medicine Reports, vol. 6, Jun. 27, 2012, pp. 553-557.
Hao-Nan Chang et al., "Blocking of the PD-1/PD-L1 Interaction by a D-Peptide Antagonist for Cancer Immunotherapy", Angewandte Comminication, Cancer Immunotherapy, International Edition, vol. 54, No. 40, Aug. 10, 2015, pp. 11760-11764.
International Search Report issued in International Application No. PCT/EP2016/076027 dated Feb. 8, 2017, 5 pages.
Written Opinion issued in International Application No. PCT/EP2016/076027 dated Feb. 8, 2017, 6 pages.

* cited by examiner

*Primary Examiner* — Thomas S Heard
(74) *Attorney, Agent, or Firm* — Cantor Colburn LLP

(57) ABSTRACT

The present disclosure relates to a class of engineered polypeptides having a binding affinity for programmed death-ligand 1 (PD-L1), and provides a PD-L1 binding polypeptide comprising the sequence $ERTX_4AX_6WEIX_{10}X_{11}LPNLX_{16}X_{17}X_{18}QX_{20}GAFIX_{25}X_{26}LHD$. The present disclosure also relates to the use of such a PD-L1 binding polypeptide a prognostic and/or diagnostic agent as well as a therapeutic agent.

25 Claims, 8 Drawing Sheets

Specification includes a Sequence Listing.

Figure 1

| Designation | Sequence | SEQ ID NO |
|---|---|---|
| Z13166 | VDAKYAKERTVAVWEIVQLPNLTAWQKGAFINKLHDDPSQSSELLSEAKKLNDSQAPK | 1 |
| Z13178 | VDAKYAKERTWAVWEIMDLPNLTAGQRGAFINKLHDDPSQSSELLSEAKKLNDSQAPK | 2 |
| Z13359 | VDAKYAKERTIAVWEIMDLPNLTSWQRGAFIDKLHDDPSQSSELLSEAKKLNDSQAPK | 3 |
| Z13398 | VDAKYAKERTMATWEIVQLPNLTARQKGAFIWKLHDDPSQSSELLSEAKKLNDSQAPK | 4 |
| Z15171-Cys | AEAKYAKERTVAVWEIVQLPNLTAWQKGAFINKLHDDPSQSSELLSEAKKLNDSQAPKVDC | 5 |

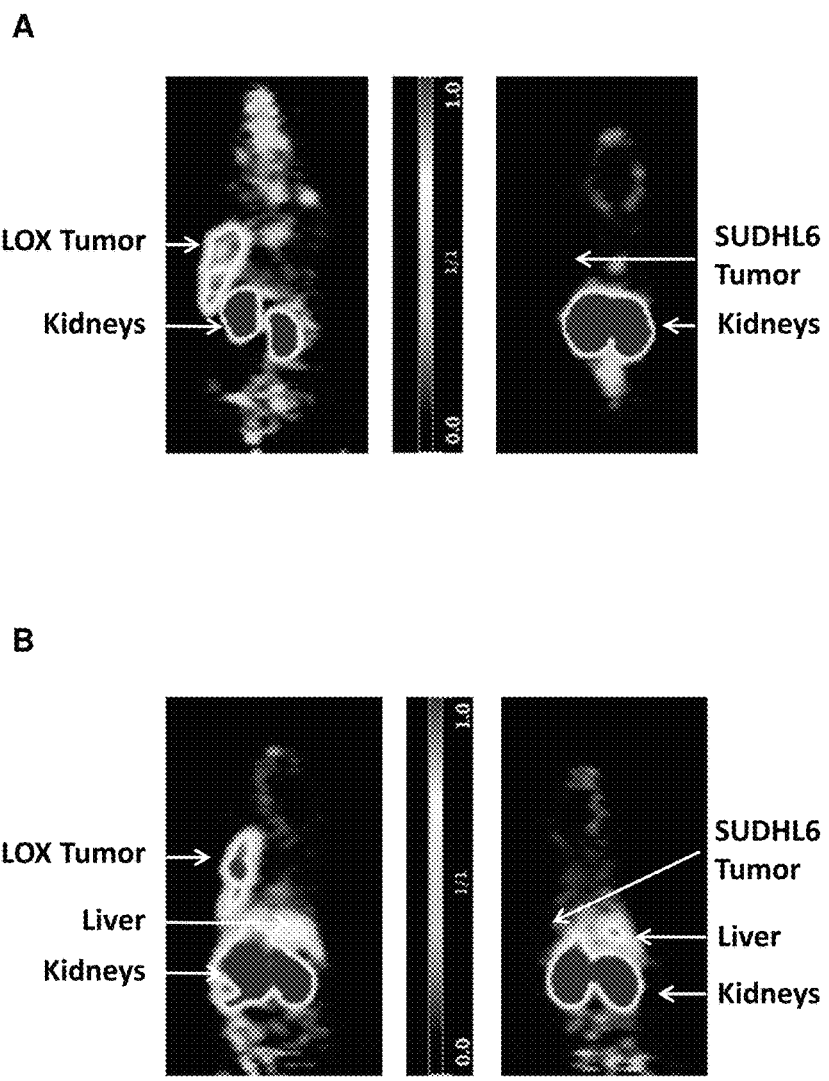
Figure 6A-B

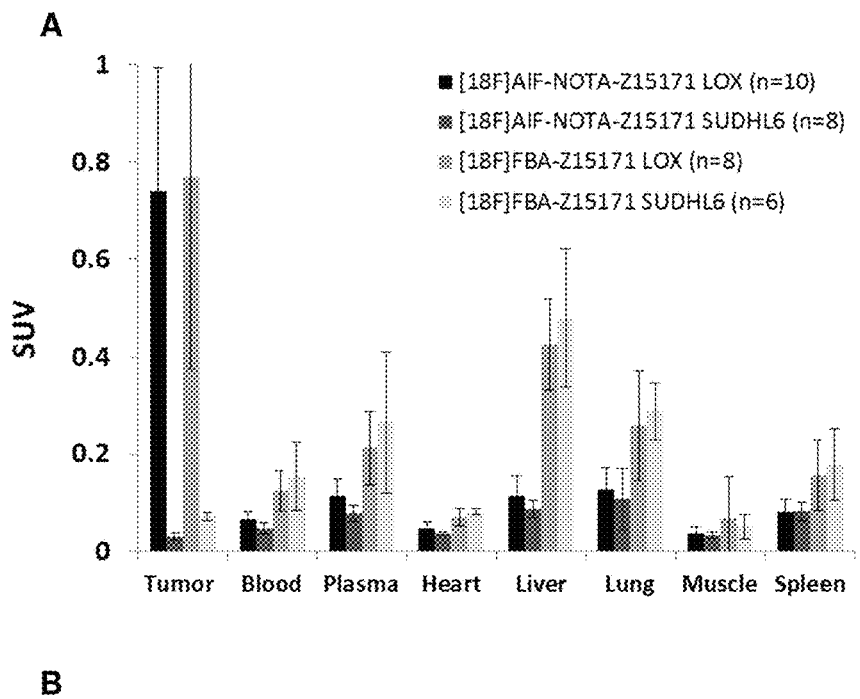
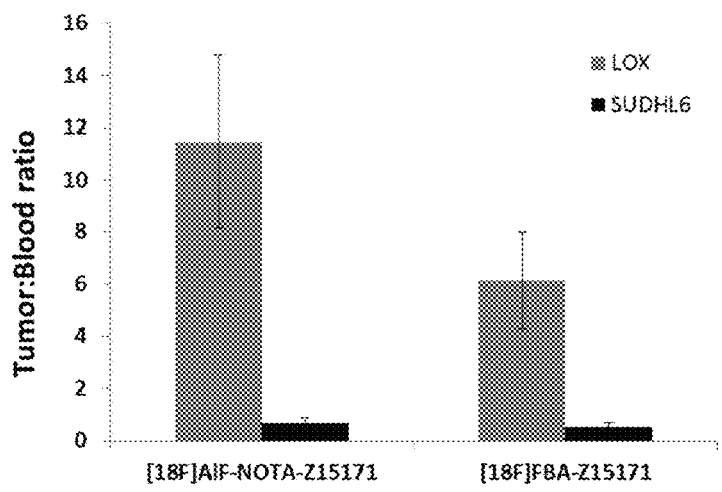
Figure 7A-B

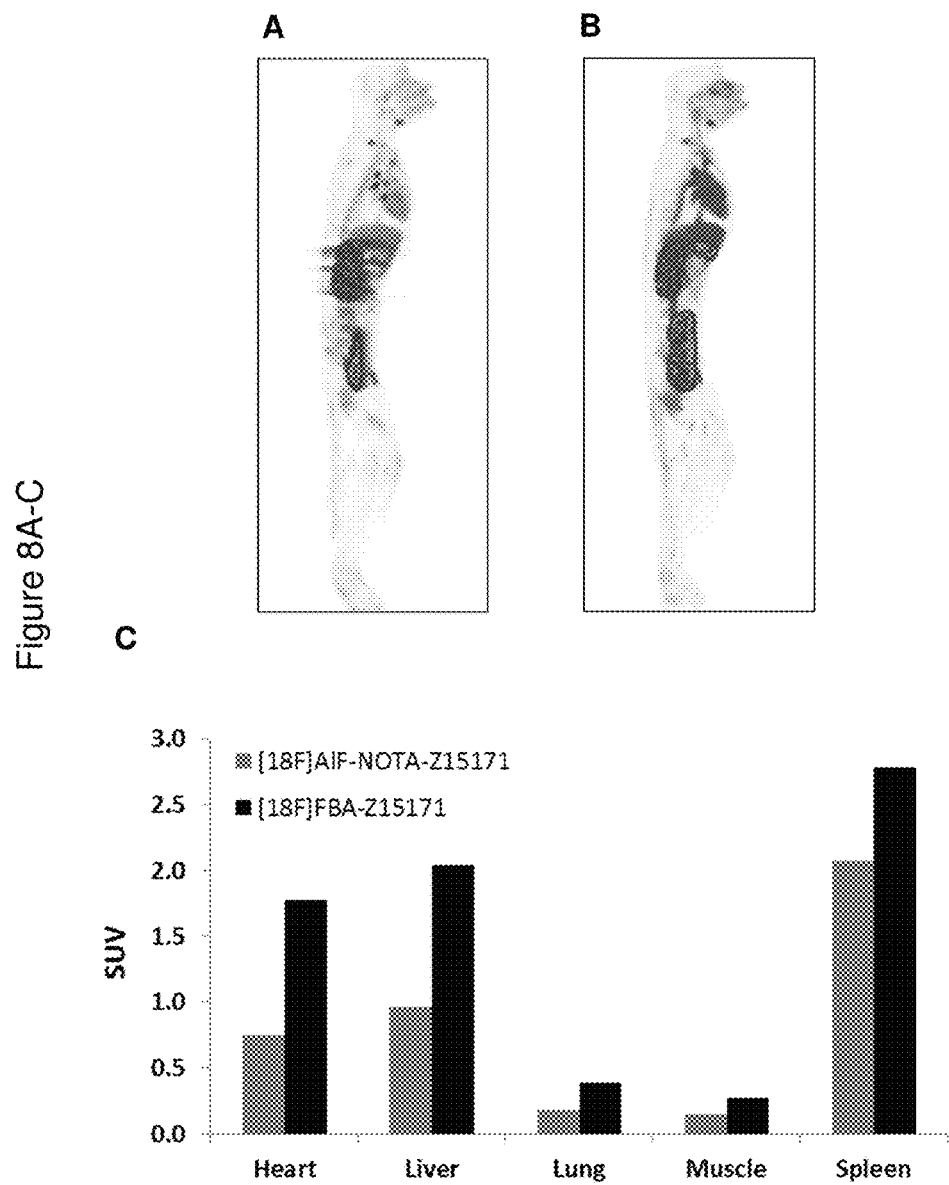
Figure 8A-C

SEQUENCE LISTING

<160> NUMBER OF SEQ ID NOS: 81

<210> SEQ ID NO 1
<211> LENGTH: 58
<212> TYPE: PRT
<213> ORGANISM: Artificial Sequence

```
<220> FEATURE:
<223> OTHER INFORMATION: Engineered PD-L1 binding polypeptide

<400> SEQUENCE: 1

Val Asp Ala Lys Tyr Ala Lys Glu Arg Thr Val Ala Val Trp Glu Ile
1               5                   10                  15

Val Gln Leu Pro Asn Leu Thr Ala Trp Gln Lys Gly Ala Phe Ile Asn
            20                  25                  30

Lys Leu His Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 2
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 2

Val Asp Ala Lys Tyr Ala Lys Glu Arg Thr Trp Ala Val Trp Glu Ile
1               5                   10                  15

Met Asp Leu Pro Asn Leu Thr Ala Gly Gln Arg Gly Ala Phe Ile Asn
            20                  25                  30

Lys Leu His Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 3
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 3

Val Asp Ala Lys Tyr Ala Lys Glu Arg Thr Ile Ala Val Trp Glu Ile
1               5                   10                  15

Met Asp Leu Pro Asn Leu Thr Ser Trp Gln Arg Gly Ala Phe Ile Asp
            20                  25                  30

Lys Leu His Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 4
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 4

Val Asp Ala Lys Tyr Ala Lys Glu Arg Thr Met Ala Thr Trp Glu Ile
1               5                   10                  15

Val Gln Leu Pro Asn Leu Thr Ala Arg Gln Lys Gly Ala Phe Ile Trp
            20                  25                  30

Lys Leu His Asp Asp Pro Ser Gln Ser Ser Glu Leu Leu Ser Glu Ala
        35                  40                  45
```

```
Lys Lys Leu Asn Asp Ser Gln Ala Pro Lys
    50                  55
```

<210> SEQ ID NO 5
<211> LENGTH: 61
<212> TYPE: PRT
<213> ORGANISM: Artificial Sequence
<220> FEATURE:
<223> OTHER INFORMATION: Engineered PD-L1 binding polypeptide

<400> SEQUENCE: 5

```
Ala Glu Ala Lys Tyr Ala Lys Glu Arg Thr Val Ala Val Trp Glu Ile
1               5                   10                  15

Val Gln Leu Pro Asn Leu Thr Ala Trp Gln Lys Gly Ala Phe Ile Asn
            20                  25                  30

Lys Leu His Asp Asp Pro Ser Gln Ser Ser Glu Leu Leu Ser Glu Ala
        35                  40                  45

Lys Lys Leu Asn Asp Ser Gln Ala Pro Lys Val Asp Cys
    50                  55                  60
```

<210> SEQ ID NO 6
<211> LENGTH: 16
<212> TYPE: PRT
<213> ORGANISM: Artificial Sequence
<220> FEATURE:
<223> OTHER INFORMATION: Linker

<400> SEQUENCE: 6

```
Gly Gly Gly Gly Ser Leu Val Pro Arg Gly Ser Gly Gly Gly Gly Ser
1               5                   10                  15
```

<210> SEQ ID NO 7
<211> LENGTH: 6
<212> TYPE: PRT
<213> ORGANISM: Artificial Sequence
<220> FEATURE:
<223> OTHER INFORMATION: Linker

<400> SEQUENCE: 7

```
Gly Ser Gly Ser Gly Ser
1               5
```

<210> SEQ ID NO 8
<211> LENGTH: 8
<212> TYPE: PRT
<213> ORGANISM: Artificial Sequence
<220> FEATURE:
<223> OTHER INFORMATION: Linker

<400> SEQUENCE: 8

```
Gly Ser Gly Ser Gly Ser Gly Ser
1               5
```

<210> SEQ ID NO 9
<211> LENGTH: 16
<212> TYPE: PRT
<213> ORGANISM: Artificial Sequence
<220> FEATURE:
<223> OTHER INFORMATION: Linker

<400> SEQUENCE: 9

```
Gly Ser Gly Ser Gly Ser Gly Ser Gly Ser Gly Ser Gly Ser Gly Ser
1               5                   10                  15
```

```
<210> SEQ ID NO 10
<211> LENGTH: 11
<212> TYPE: PRT
<213> ORGANISM: Artificial Sequence
<220> FEATURE:
<223> OTHER INFORMATION: Linker

<400> SEQUENCE: 10

Gly Gly Ser Gly Gly His Met Gly Ser Gly Gly
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Linker

<400> SEQUENCE: 11

Gly Gly Ser Gly Gly Ser Gly Gly Ser Gly Gly
1               5                   10

<210> SEQ ID NO 12
<211> LENGTH: 5
<212> TYPE: PRT
<213> ORGANISM: Artificial Sequence
<220> FEATURE:
<223> OTHER INFORMATION: Linker

<400> SEQUENCE: 12

Gly Gly Ser Gly Gly
1               5

<210> SEQ ID NO 13
<211> LENGTH: 8
<212> TYPE: PRT
<213> ORGANISM: Artificial Sequence
<220> FEATURE:
<223> OTHER INFORMATION: Linker

<400> SEQUENCE: 13

Gly Gly Ser Gly Gly Gly Gly Gly
1               5

<210> SEQ ID NO 14
<211> LENGTH: 18
<212> TYPE: PRT
<213> ORGANISM: Artificial Sequence
<220> FEATURE:
<223> OTHER INFORMATION: Linker

<400> SEQUENCE: 14

Gly Gly Gly Ser Glu Gly Gly Gly Ser Glu Gly Gly Gly Ser Glu Gly
1               5                   10                  15

Gly Gly

<210> SEQ ID NO 15
<211> LENGTH: 8
<212> TYPE: PRT
<213> ORGANISM: Artificial Sequence
<220> FEATURE:
<223> OTHER INFORMATION: Linker

<400> SEQUENCE: 15

Ala Ala Gly Ala Ala Thr Ala Ala
1               5
```

```
<210> SEQ ID NO 16
<211> LENGTH: 5
<212> TYPE: PRT
<213> ORGANISM: Artificial Sequence
<220> FEATURE:
<223> OTHER INFORMATION: Linker

<400> SEQUENCE: 16

Gly Gly Gly Gly Gly
1               5

<210> SEQ ID NO 17
<211> LENGTH: 5
<212> TYPE: PRT
<213> ORGANISM: Artificial Sequence
<220> FEATURE:
<223> OTHER INFORMATION: Linker

<400> SEQUENCE: 17

Gly Gly Ser Ser Gly
1               5

<210> SEQ ID NO 18
<211> LENGTH: 11
<212> TYPE: PRT
<213> ORGANISM: Artificial Sequence
<220> FEATURE:
<223> OTHER INFORMATION: Linker

<400> SEQUENCE: 18

Gly Ser Gly Gly Gly Thr Gly Gly Gly Ser Gly
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Linker

<400> SEQUENCE: 19

Gly Ser Gly Gly Gly Thr Gly Gly Gly Ser Gly
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Linker

<400> SEQUENCE: 20

Gly Ser Gly Ser Gly Ser Gly Ser Gly Gly Ser Gly
1               5                   10

<210> SEQ ID NO 21
<211> LENGTH: 14
<212> TYPE: PRT
<213> ORGANISM: Artificial Sequence
<220> FEATURE:
<223> OTHER INFORMATION: Linker

<400> SEQUENCE: 21

Gly Ser Gly Gly Ser Gly Gly Ser Gly Gly Ser Gly Gly Ser
1               5                   10
```

-continued

<210> SEQ ID NO 22
<211> LENGTH: 14
<212> TYPE: PRT
<213> ORGANISM: Artificial Sequence
<220> FEATURE:
<223> OTHER INFORMATION: Linker

<400> SEQUENCE: 22

Gly Ser Gly Gly Ser Gly Ser Gly Gly Ser Gly Gly Ser Gly
1               5                   10

<210> SEQ ID NO 23
<211> LENGTH: 29
<212> TYPE: PRT
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
<222> LOCATION: (4)..(4)
<223> OTHER INFORMATION: Xaa is selected from I, M, V and W
<220> FEATURE:
<221> NAME/KEY: misc_feature
<222> LOCATION: (6)..(6)
<223> OTHER INFORMATION: Xaa is selected from T and V
<220> FEATURE:
<221> NAME/KEY: misc_feature
<222> LOCATION: (10)..(10)
<223> OTHER INFORMATION: X10 is selected from M and V
<220> FEATURE:
<221> NAME/KEY: misc_feature
<222> LOCATION: (11)..(11)
<223> OTHER INFORMATION: X11 is selected from D and Q
<220> FEATURE:
<221> NAME/KEY: misc_feature
<222> LOCATION: (16)..(16)
<223> OTHER INFORMATION: X16 is selected from N and T
<220> FEATURE:
<221> NAME/KEY: misc_feature
<222> LOCATION: (16)..(16)
<223> OTHER INFORMATION: X16 is selected from N and T
<220> FEATURE:
<221> NAME/KEY: misc_feature
<222> LOCATION: (17)..(17)
<223> OTHER INFORMATION: X17 is selected from A and S
<220> FEATURE:
<221> NAME/KEY: misc_feature
<222> LOCATION: (18)..(18)
<223> OTHER INFORMATION: Xaa is selected from G, R and W
<220> FEATURE:
<221> NAME/KEY: misc_feature
<222> LOCATION: (20)..(20)
<223> OTHER INFORMATION: X20 is selected from K and R
<220> FEATURE:
<221> NAME/KEY: misc_feature
<222> LOCATION: (25)..(25)
<223> OTHER INFORMATION: X25 is selected from D, N and W
<220> FEATURE:
<221> NAME/KEY: misc_feature
<222> LOCATION: (26)..(26)
<223> OTHER INFORMATION: X26 is selected from K and S

<400> SEQUENCE: 23

Glu Arg Thr Xaa Ala Xaa Trp Glu Ile Xaa Xaa Leu Pro Asn Leu Xaa
1               5                   10                  15

Xaa Xaa Gln Xaa Gly Ala Phe Ile Xaa Xaa Leu His Asp
            20                  25

<210> SEQ ID NO 24
<211> LENGTH: 49
<212> TYPE: PRT
<213> ORGANISM: ARTIFICIAL SEQUENCE
<220> FEATURE:
<223> OTHER INFORMATION: Engineered PDL1 binding polypeptide

```
<220> FEATURE:
<221> NAME/KEY: misc_feature
<222> LOCATION: (5)..(5)
<223> OTHER INFORMATION: Xaa is selected from I, M, V and W
<220> FEATURE:
<221> NAME/KEY: misc_feature
<222> LOCATION: (7)..(7)
<223> OTHER INFORMATION: Xaa is selected from T and V
<220> FEATURE:
<221> NAME/KEY: misc_feature
<222> LOCATION: (11)..(11)
<223> OTHER INFORMATION: Xaa is selected from M and V
<220> FEATURE:
<221> NAME/KEY: misc_feature
<222> LOCATION: (12)..(12)
<223> OTHER INFORMATION: Xaa is selected from D and Q
<220> FEATURE:
<221> NAME/KEY: misc_feature
<222> LOCATION: (17)..(17)
<223> OTHER INFORMATION: Xaa is selected from N and T
<220> FEATURE:
<221> NAME/KEY: misc_feature
<222> LOCATION: (18)..(18)
<223> OTHER INFORMATION: Xaa is selected from A and S
<220> FEATURE:
<221> NAME/KEY: misc_feature
<222> LOCATION: (19)..(19)
<223> OTHER INFORMATION: Xaa is selected from G, R and W
<220> FEATURE:
<221> NAME/KEY: misc_feature
<222> LOCATION: (21)..(21)
<223> OTHER INFORMATION: Xaa is selected from K and R
<220> FEATURE:
<221> NAME/KEY: misc_feature
<222> LOCATION: (26)..(26)
<223> OTHER INFORMATION: Xaa is selected from D, N and W
<220> FEATURE:
<221> NAME/KEY: misc_feature
<222> LOCATION: (27)..(27)
<223> OTHER INFORMATION: Xaa is selected from K and S
<220> FEATURE:
<221> NAME/KEY: misc_feature
<222> LOCATION: (36)..(36)
<223> OTHER INFORMATION: Xaa is selected from A and S
<220> FEATURE:
<221> NAME/KEY: misc_feature
<222> LOCATION: (37)..(37)
<223> OTHER INFORMATION: Xaa is selected from N and E
<220> FEATURE:
<221> NAME/KEY: misc_feature
<222> LOCATION: (40)..(40)
<223> OTHER INFORMATION: Xaa is selected from A, S and C
<220> FEATURE:
<221> NAME/KEY: misc_feature
<222> LOCATION: (46)..(46)
<223> OTHER INFORMATION: Xaa is selected from E, N and S
<220> FEATURE:
<221> NAME/KEY: misc_feature
<222> LOCATION: (47)..(47)
<223> OTHER INFORMATION: Xaa is selected from D, E and S
<220> FEATURE:
<221> NAME/KEY: misc_feature
<222> LOCATION: (48)..(48)
<223> OTHER INFORMATION: Xaa is selected from A and S

<400> SEQUENCE: 24

Lys Glu Arg Thr Xaa Ala Xaa Trp Glu Ile Xaa Xaa Leu Pro Asn Leu
1               5                   10                  15

Xaa Xaa Xaa Gln Xaa Gly Ala Phe Ile Xaa Xaa Leu His Asp Asp Pro
            20                  25                  30

Ser Gln Ser Xaa Xaa Leu Leu Xaa Glu Ala Lys Lys Leu Xaa Xaa Xaa
        35                  40                  45

Gln
```

-continued

```
<210> SEQ ID NO 25
<211> LENGTH: 53
<212> TYPE: PRT
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
<222> LOCATION: (7)..(7)
<223> OTHER INFORMATION: Xaa is selected from I, M, V and W
<220> FEATURE:
<221> NAME/KEY: misc_feature
<222> LOCATION: (9)..(9)
<223> OTHER INFORMATION: Xaa is selected from T and V
<220> FEATURE:
<221> NAME/KEY: misc_feature
<222> LOCATION: (13)..(13)
<223> OTHER INFORMATION: Xaa is selected from M and V
<220> FEATURE:
<221> NAME/KEY: misc_feature
<222> LOCATION: (14)..(14)
<223> OTHER INFORMATION: Xaa is selected from D and Q
<220> FEATURE:
<221> NAME/KEY: misc_feature
<222> LOCATION: (19)..(19)
<223> OTHER INFORMATION: Xaa is selected from N and T
<220> FEATURE:
<221> NAME/KEY: misc_feature
<222> LOCATION: (20)..(20)
<223> OTHER INFORMATION: Xaa is selected from A and S
<220> FEATURE:
<221> NAME/KEY: misc_feature
<222> LOCATION: (21)..(21)
<223> OTHER INFORMATION: Xaa is selected from G, R and W
<220> FEATURE:
<221> NAME/KEY: misc_feature
<222> LOCATION: (23)..(23)
<223> OTHER INFORMATION: Xaa is selected from K and R
<220> FEATURE:
<221> NAME/KEY: misc_feature
<222> LOCATION: (28)..(28)
<223> OTHER INFORMATION: Xaa is selected from D, N and W
<220> FEATURE:
<221> NAME/KEY: misc_feature
<222> LOCATION: (29)..(29)
<223> OTHER INFORMATION: Xaa is selected from K and S
<220> FEATURE:
<221> NAME/KEY: misc_feature
<222> LOCATION: (38)..(38)
<223> OTHER INFORMATION: Xaa is selected from A and S
<220> FEATURE:
<221> NAME/KEY: misc_feature
<222> LOCATION: (39)..(39)
<223> OTHER INFORMATION: Xaa is selected from N and E
<220> FEATURE:
<221> NAME/KEY: misc_feature
<222> LOCATION: (42)..(42)
<223> OTHER INFORMATION: Xaa is selected from A, S and C
<220> FEATURE:
<221> NAME/KEY: misc_feature
<222> LOCATION: (48)..(48)
<223> OTHER INFORMATION: Xaa is selected from E, N and S
<220> FEATURE:
<221> NAME/KEY: misc_feature
<222> LOCATION: (49)..(49)
<223> OTHER INFORMATION: Xaa is selected from D, E and S
<220> FEATURE:
<221> NAME/KEY: misc_feature
<222> LOCATION: (50)..(50)
<223> OTHER INFORMATION: Xaa is selected from A and S

<400> SEQUENCE: 25

Tyr Ala Lys Glu Arg Thr Xaa Ala Xaa Trp Glu Ile Xaa Xaa Leu Pro
1               5                   10                  15

Asn Leu Xaa Xaa Xaa Gln Xaa Gly Ala Phe Ile Xaa Xaa Leu His Asp
            20                  25                  30
```

```
Asp Pro Ser Gln Ser Xaa Xaa Leu Leu Xaa Glu Ala Lys Lys Leu Xaa
                35                  40                  45

Xaa Xaa Gln Ala Pro
    50
```

```
<210> SEQ ID NO 26
<211> LENGTH: 53
<212> TYPE: PRT
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
<222> LOCATION: (7)..(7)
<223> OTHER INFORMATION: Xaa is selected from I, M, V and W
<220> FEATURE:
<221> NAME/KEY: misc_feature
<222> LOCATION: (9)..(9)
<223> OTHER INFORMATION: Xaa is selected from T and V
<220> FEATURE:
<221> NAME/KEY: misc_feature
<222> LOCATION: (13)..(13)
<223> OTHER INFORMATION: Xaa is selected from M and V
<220> FEATURE:
<221> NAME/KEY: misc_feature
<222> LOCATION: (14)..(14)
<223> OTHER INFORMATION: Xaa is selected from D and Q
<220> FEATURE:
<221> NAME/KEY: misc_feature
<222> LOCATION: (19)..(19)
<223> OTHER INFORMATION: Xaa is selected from N and T
<220> FEATURE:
<221> NAME/KEY: misc_feature
<222> LOCATION: (20)..(20)
<223> OTHER INFORMATION: Xaa is selected from A and S
<220> FEATURE:
<221> NAME/KEY: misc_feature
<222> LOCATION: (21)..(21)
<223> OTHER INFORMATION: Xaa is selected from G, R and W
<220> FEATURE:
<221> NAME/KEY: misc_feature
<222> LOCATION: (23)..(23)
<223> OTHER INFORMATION: Xaa is selected from K and R
<220> FEATURE:
<221> NAME/KEY: misc_feature
<222> LOCATION: (28)..(28)
<223> OTHER INFORMATION: Xaa is selected from D, N and W
<220> FEATURE:
<221> NAME/KEY: misc_feature
<222> LOCATION: (29)..(29)
<223> OTHER INFORMATION: Xaa is selected from K and S
<220> FEATURE:
<221> NAME/KEY: misc_feature
<222> LOCATION: (38)..(38)
<223> OTHER INFORMATION: Xaa is selected from A and S
<220> FEATURE:
<221> NAME/KEY: misc_feature
<222> LOCATION: (39)..(39)
<223> OTHER INFORMATION: Xaa is selected from N and E
<220> FEATURE:
<221> NAME/KEY: misc_feature
<222> LOCATION: (42)..(42)
<223> OTHER INFORMATION: Xaa is selected from A, S and C
<220> FEATURE:
<221> NAME/KEY: misc_feature
<222> LOCATION: (48)..(50)
<223> OTHER INFORMATION: X48 is selected from E, N and S; X49 is
      selected from D, E and S; and X50 is selected from A and S;

<400> SEQUENCE: 26

Phe Asn Lys Glu Arg Thr Xaa Ala Xaa Trp Glu Ile Xaa Xaa Leu Pro
1               5                   10                  15

Asn Leu Xaa Xaa Xaa Gln Xaa Gly Ala Phe Ile Xaa Xaa Leu His Asp
            20                  25                  30
```

```
Asp Pro Ser Gln Ser Xaa Xaa Leu Leu Xaa Glu Ala Lys Lys Leu Xaa
        35                  40                  45

Xaa Xaa Gln Ala Pro
    50
```

<210> SEQ ID NO 27
<211> LENGTH: 53
<212> TYPE: PRT
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
<222> LOCATION: (7)..(7)
<223> OTHER INFORMATION: Xaa is selected from I, M, V and W
<220> FEATURE:
<221> NAME/KEY: misc_feature
<222> LOCATION: (9)..(9)
<223> OTHER INFORMATION: Xaa is selected from T and V
<220> FEATURE:
<221> NAME/KEY: misc_feature
<222> LOCATION: (13)..(14)
<223> OTHER INFORMATION: X13 is selected from M and V; X14 is selected
      from D and Q;
<220> FEATURE:
<221> NAME/KEY: misc_feature
<222> LOCATION: (19)..(21)
<223> OTHER INFORMATION: X19 is selected from N and T; X20 is selected
      from A and S; X21 is selected from G, R and W;
<220> FEATURE:
<221> NAME/KEY: misc_feature
<222> LOCATION: (23)..(23)
<223> OTHER INFORMATION: Xaa is selected from K and R
<220> FEATURE:
<221> NAME/KEY: misc_feature
<222> LOCATION: (28)..(29)
<223> OTHER INFORMATION: X28 is selected from D, N and W; and X29 is
      selected from K and S;
<220> FEATURE:
<221> NAME/KEY: misc_feature
<222> LOCATION: (42)..(42)
<223> OTHER INFORMATION: Xaa is selected from A and C

<400> SEQUENCE: 27

```
Phe Asn Lys Glu Arg Thr Xaa Ala Xaa Trp Glu Ile Xaa Xaa Leu Pro
1               5                   10                  15

Asn Leu Xaa Xaa Xaa Gln Xaa Gly Ala Phe Ile Xaa Xaa Leu His Asp
            20                  25                  30

Asp Pro Ser Gln Ser Ala Asn Leu Leu Xaa Glu Ala Lys Lys Leu Asn
        35                  40                  45

Asp Ala Gln Ala Pro
    50
```

<210> SEQ ID NO 28
<211> LENGTH: 53
<212> TYPE: PRT
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
<222> LOCATION: (7)..(7)
<223> OTHER INFORMATION: Xaa is selected from I, M, V and W
<220> FEATURE:
<221> NAME/KEY: misc_feature
<222> LOCATION: (9)..(9)
<223> OTHER INFORMATION: Xaa is selected from T and V
<220> FEATURE:
<221> NAME/KEY: misc_feature
<222> LOCATION: (13)..(14)
<223> OTHER INFORMATION: X13 is selected from M and V; X14 is selected
      from D and Q;

```
<220> FEATURE:
<221> NAME/KEY: misc_feature
<222> LOCATION: (19)..(21)
<223> OTHER INFORMATION: X19 is selected from N and T; X20 is selected
      from A and S; X21 is selected from G, R and W;
<220> FEATURE:
<221> NAME/KEY: misc_feature
<222> LOCATION: (23)..(23)
<223> OTHER INFORMATION: Xaa is selected from K and R;
<220> FEATURE:
<221> NAME/KEY: misc_feature
<222> LOCATION: (28)..(29)
<223> OTHER INFORMATION: X28 is selected from D, N and W; and X29 is
      selected from K and S;
<220> FEATURE:
<221> NAME/KEY: misc_feature
<222> LOCATION: (42)..(42)
<223> OTHER INFORMATION: Xaa is selected from A, S and C

<400> SEQUENCE: 28

Phe Ala Lys Glu Arg Thr Xaa Ala Xaa Trp Glu Ile Xaa Xaa Leu Pro
1               5                   10                  15

Asn Leu Xaa Xaa Xaa Gln Xaa Gly Ala Phe Ile Xaa Xaa Leu His Asp
            20                  25                  30

Asp Pro Ser Gln Ser Ser Glu Leu Leu Xaa Glu Ala Lys Lys Leu Ser
        35                  40                  45

Glu Ser Gln Ala Pro
    50

<210> SEQ ID NO 29
<211> LENGTH: 53
<212> TYPE: PRT
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
<222> LOCATION: (7)..(7)
<223> OTHER INFORMATION: Xaa is selected from I, M, V and W
<220> FEATURE:
<221> NAME/KEY: misc_feature
<222> LOCATION: (9)..(9)
<223> OTHER INFORMATION: Xaa is selected from T and V
<220> FEATURE:
<221> NAME/KEY: misc_feature
<222> LOCATION: (13)..(14)
<223> OTHER INFORMATION: X13 is selected from M and V; X14 is selected
      from D and Q;
<220> FEATURE:
<221> NAME/KEY: misc_feature
<222> LOCATION: (19)..(21)
<223> OTHER INFORMATION: X19 is selected from N and T; X20 is selected
      from A and S; X21 is selected from G, R and W;
<220> FEATURE:
<221> NAME/KEY: misc_feature
<222> LOCATION: (23)..(23)
<223> OTHER INFORMATION: Xaa is selected from K and R;
<220> FEATURE:
<221> NAME/KEY: misc_feature
<222> LOCATION: (28)..(29)
<223> OTHER INFORMATION: X28 is selected from D, N and W; and X29 is
      selected from K and S;
<220> FEATURE:
<221> NAME/KEY: misc_feature
<222> LOCATION: (42)..(42)
<223> OTHER INFORMATION: Xaa is selected from A, S and C

<400> SEQUENCE: 29

Phe Ala Lys Glu Arg Thr Xaa Ala Xaa Trp Glu Ile Xaa Xaa Leu Pro
1               5                   10                  15

Asn Leu Xaa Xaa Xaa Gln Xaa Gly Ala Phe Ile Xaa Xaa Leu His Asp
            20                  25                  30
```

Asp Pro Ser Gln Ser Ser Glu Leu Leu Xaa Glu Ala Lys Lys Leu Asn
        35                  40                  45

Asp Ser Gln Ala Pro
    50

<210> SEQ ID NO 30
<211> LENGTH: 53
<212> TYPE: PRT
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
<222> LOCATION: (7)..(7)
<223> OTHER INFORMATION: Xaa is selected from I, M, V and W
<220> FEATURE:
<221> NAME/KEY: misc_feature
<222> LOCATION: (9)..(9)
<223> OTHER INFORMATION: Xaa is selected from T and V
<220> FEATURE:
<221> NAME/KEY: misc_feature
<222> LOCATION: (13)..(14)
<223> OTHER INFORMATION: X13 is selected from M and V; X14 is selected
      from D and Q;
<220> FEATURE:
<221> NAME/KEY: misc_feature
<222> LOCATION: (19)..(21)
<223> OTHER INFORMATION: X19 is selected from N and T; X20 is selected
      from A and S; X21 is selected from G, R and W;
<220> FEATURE:
<221> NAME/KEY: misc_feature
<222> LOCATION: (23)..(23)
<223> OTHER INFORMATION: Xaa is selected from K and R;
<220> FEATURE:
<221> NAME/KEY: misc_feature
<222> LOCATION: (28)..(29)
<223> OTHER INFORMATION: X28 is selected from D, N and W; and X29 is
      selected from K and S;
<220> FEATURE:
<221> NAME/KEY: misc_feature
<222> LOCATION: (42)..(42)
<223> OTHER INFORMATION: Xaa can be any naturally occurring amino acid

<400> SEQUENCE: 30

Tyr Ala Lys Glu Arg Thr Xaa Ala Xaa Trp Glu Ile Xaa Xaa Leu Pro
1               5                   10                  15

Asn Leu Xaa Xaa Xaa Gln Xaa Gly Ala Phe Ile Xaa Xaa Leu His Asp
                20                  25                  30

Asp Pro Ser Gln Ser Ser Glu Leu Leu Xaa Glu Ala Lys Lys Leu Asn
        35                  40                  45

Asp Ser Gln Ala Pro
    50

<210> SEQ ID NO 31
<211> LENGTH: 58
<212> TYPE: PRT
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
<222> LOCATION: (11)..(11)
<223> OTHER INFORMATION: Xaa is selected from I, M, V and W
<220> FEATURE:
<221> NAME/KEY: misc_feature
<222> LOCATION: (13)..(13)
<223> OTHER INFORMATION: Xaa is selected from T and V
<220> FEATURE:
<221> NAME/KEY: misc_feature
<222> LOCATION: (17)..(18)
<223> OTHER INFORMATION: X17 is selected from M and V; X18 is selected

```
              from D and Q;
<220> FEATURE:
<221> NAME/KEY: misc_feature
<222> LOCATION: (23)..(25)
<223> OTHER INFORMATION: X23 is selected from N and T; X24 is selected
      from A and S; X25 is selected from G, R and W
<220> FEATURE:
<221> NAME/KEY: misc_feature
<222> LOCATION: (27)..(27)
<223> OTHER INFORMATION: Xaa is selected from K and R
<220> FEATURE:
<221> NAME/KEY: misc_feature
<222> LOCATION: (32)..(33)
<223> OTHER INFORMATION: X32 is selected from D, N and W; and X33 is
      selected from K and S

<400> SEQUENCE: 31

Ala Asp Asn Asn Phe Asn Lys Glu Arg Thr Xaa Ala Xaa Trp Glu Ile
1               5                  10                  15

Xaa Xaa Leu Pro Asn Leu Xaa Xaa Xaa Gln Xaa Gly Ala Phe Ile Xaa
            20                  25                  30

Xaa Leu His Asp Asp Pro Ser Gln Ser Ala Asn Leu Leu Ser Glu Ala
            35                  40                  45

Lys Lys Leu Asn Glu Ser Gln Ala Pro Lys
    50                  55

<210> SEQ ID NO 32
<211> LENGTH: 58
<212> TYPE: PRT
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
<222> LOCATION: (11)..(11)
<223> OTHER INFORMATION: Xaa is selected from I, M, V and W
<220> FEATURE:
<221> NAME/KEY: misc_feature
<222> LOCATION: (13)..(13)
<223> OTHER INFORMATION: Xaa is selected from T and V
<220> FEATURE:
<221> NAME/KEY: misc_feature
<222> LOCATION: (17)..(18)
<223> OTHER INFORMATION: X17 is selected from M and V; X18 is selected
      from D and Q;
<220> FEATURE:
<221> NAME/KEY: misc_feature
<222> LOCATION: (23)..(25)
<223> OTHER INFORMATION: X23 is selected from N and T; X24 is selected
      from A and S; X25 is selected from G, R and W
<220> FEATURE:
<221> NAME/KEY: misc_feature
<222> LOCATION: (27)..(27)
<223> OTHER INFORMATION: Xaa is selected from K and R
<220> FEATURE:
<221> NAME/KEY: misc_feature
<222> LOCATION: (32)..(33)
<223> OTHER INFORMATION: X32 is selected from D, N and W; and X33 is
      selected from K and S

<400> SEQUENCE: 32

Ala Asp Asn Lys Phe Asn Lys Glu Arg Thr Xaa Ala Xaa Trp Glu Ile
1               5                  10                  15

Xaa Xaa Leu Pro Asn Leu Xaa Xaa Xaa Gln Xaa Gly Ala Phe Ile Xaa
            20                  25                  30

Xaa Leu His Asp Asp Pro Ser Gln Ser Ala Asn Leu Leu Ala Glu Ala
            35                  40                  45

Lys Lys Leu Asn Asp

-continued

```
<210> SEQ ID NO 33
<211> LENGTH: 58
<212> TYPE: PRT
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
<222> LOCATION: (11)..(11)
<223> OTHER INFORMATION: Xaa is selected from I, M, V and W
<220> FEATURE:
<221> NAME/KEY: misc_feature
<222> LOCATION: (13)..(13)
<223> OTHER INFORMATION: Xaa is selected from T and V;
<220> FEATURE:
<221> NAME/KEY: misc_feature
<222> LOCATION: (17)..(18)
<223> OTHER INFORMATION: X17 is selected from M and V; X18 is selected
      from D and Q;
<220> FEATURE:
<221> NAME/KEY: misc_feature
<222> LOCATION: (23)..(25)
<223> OTHER INFORMATION: X23 is selected from N and T; X24 is selected
      from A and S; X25 is selected from G, R and W
<220> FEATURE:
<221> NAME/KEY: misc_feature
<222> LOCATION: (27)..(27)
<223> OTHER INFORMATION: Xaa is selected from K and R
<220> FEATURE:
<221> NAME/KEY: misc_feature
<222> LOCATION: (32)..(33)
<223> OTHER INFORMATION: X32 is selected from D, N and W; and X33 is
      selected from K and S

<400> SEQUENCE: 33

Ala Asp Asn Lys Phe Asn Lys Glu Arg Thr Xaa Ala Xaa Trp Glu Ile
1               5                   10                  15

Xaa Xaa Leu Pro Asn Leu Xaa Xaa Xaa Gln Xaa Gly Ala Phe Ile Xaa
            20                  25                  30

Xaa Leu His Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 34
<211> LENGTH: 61
<212> TYPE: PRT
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
<222> LOCATION: (14)..(14)
<223> OTHER INFORMATION: Xaa is selected from I, M, V and W
<220> FEATURE:
<221> NAME/KEY: misc_feature
<222> LOCATION: (16)..(16)
<223> OTHER INFORMATION: Xaa is selected from T and V
<220> FEATURE:
<221> NAME/KEY: misc_feature
<222> LOCATION: (20)..(21)
<223> OTHER INFORMATION: X20 is selected from M and V; X21 is selected
      from D and Q;
<220> FEATURE:
<221> NAME/KEY: misc_feature
<222> LOCATION: (26)..(28)
<223> OTHER INFORMATION: X26 is selected from N and T; X27 is selected
      from A and S; X28 is selected from G, R and W
<220> FEATURE:
<221> NAME/KEY: misc_feature
<222> LOCATION: (30)..(30)
<223> OTHER INFORMATION: Xaa is selected from K and R
<220> FEATURE:
```

```
<221> NAME/KEY: misc_feature
<222> LOCATION: (35)..(36)
<223> OTHER INFORMATION: X35 is selected from D, N and W; and X36 is
      selected from K and S

<400> SEQUENCE: 34

Ala Asp Ala Gln Gln Asn Asn Phe Asn Lys Glu Arg Thr Xaa Ala Xaa
1               5                   10                  15

Trp Glu Ile Xaa Xaa Leu Pro Asn Leu Xaa Xaa Xaa Gln Xaa Gly Ala
            20                  25                  30

Phe Ile Xaa Xaa Leu His Asp Asp Pro Ser Gln Ser Thr Asn Val Leu
        35                  40                  45

Gly Glu Ala Lys Lys Leu Asn Glu Ser Gln Ala Pro Lys
50                  55                  60

<210> SEQ ID NO 35
<211> LENGTH: 56
<212> TYPE: PRT
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
<222> LOCATION: (9)..(9)
<223> OTHER INFORMATION: Xaa is selected from I, M, V and W
<220> FEATURE:
<221> NAME/KEY: misc_feature
<222> LOCATION: (11)..(11)
<223> OTHER INFORMATION: Xaa is selected from T and V
<220> FEATURE:
<221> NAME/KEY: misc_feature
<222> LOCATION: (15)..(16)
<223> OTHER INFORMATION: X15 is selected from M and V; X16 is selected
      from D and Q
<220> FEATURE:
<221> NAME/KEY: misc_feature
<222> LOCATION: (21)..(23)
<223> OTHER INFORMATION: X21 is selected from N and T; X22 is selected
      from A and S; X23 is selected from G, R and W
<220> FEATURE:
<221> NAME/KEY: misc_feature
<222> LOCATION: (25)..(25)
<223> OTHER INFORMATION: Xaa is selected from K and R
<220> FEATURE:
<221> NAME/KEY: misc_feature
<222> LOCATION: (30)..(31)
<223> OTHER INFORMATION: X30 is selected from D, N and W; and X31 is
      selected from K and S

<400> SEQUENCE: 35

Ala Gln His Asp Glu Glu Arg Thr Xaa Ala Xaa Trp Glu Ile Xaa Xaa
1               5                   10                  15

Leu Pro Asn Leu Xaa Xaa Xaa Gln Xaa Gly Ala Phe Ile Xaa Xaa Leu
            20                  25                  30

His Asp Asp Pro Ser Gln Ser Ala Asn Val Leu Gly Glu Ala Gln Lys
        35                  40                  45

Leu Asn Asp Ser Gln Ala Pro Lys
    50                  55

<210> SEQ ID NO 36
<211> LENGTH: 58
<212> TYPE: PRT
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
<222> LOCATION: (11)..(11)
<223> OTHER INFORMATION: Xaa is selected from I, M, V and W
```

-continued

```
<220> FEATURE:
<221> NAME/KEY: misc_feature
<222> LOCATION: (13)..(13)
<223> OTHER INFORMATION: Xaa is selected from T and V;
<220> FEATURE:
<221> NAME/KEY: misc_feature
<222> LOCATION: (17)..(18)
<223> OTHER INFORMATION: X17 is selected from M and V; X18 is selected
      from D and Q;
<220> FEATURE:
<221> NAME/KEY: misc_feature
<222> LOCATION: (23)..(25)
<223> OTHER INFORMATION: X23 is selected from N and T; X24 is selected
      from A and S; X25 is selected from G, R and W
<220> FEATURE:
<221> NAME/KEY: misc_feature
<222> LOCATION: (27)..(27)
<223> OTHER INFORMATION: Xaa is selected from K and R
<220> FEATURE:
<221> NAME/KEY: misc_feature
<222> LOCATION: (32)..(33)
<223> OTHER INFORMATION: X32 is selected from D, N and W; and X33 is
      selected from K and S

<400> SEQUENCE: 36

Val Asp Asn Lys Phe Asn Lys Glu Arg Thr Xaa Ala Xaa Trp Glu Ile
1               5                   10                  15

Xaa Xaa Leu Pro Asn Leu Xaa Xaa Xaa Gln Xaa Gly Ala Phe Ile Xaa
            20                  25                  30

Xaa Leu His Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 37
<211> LENGTH: 58
<212> TYPE: PRT
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
<222> LOCATION: (11)..(11)
<223> OTHER INFORMATION: Xaa is selected from I, M, V and W
<220> FEATURE:
<221> NAME/KEY: misc_feature
<222> LOCATION: (13)..(13)
<223> OTHER INFORMATION: Xaa is selected from T and V;
<220> FEATURE:
<221> NAME/KEY: misc_feature
<222> LOCATION: (17)..(18)
<223> OTHER INFORMATION: X17 is selected from M and V; X18 is selected
      from D and Q;
<220> FEATURE:
<221> NAME/KEY: misc_feature
<222> LOCATION: (23)..(25)
<223> OTHER INFORMATION: X23 is selected from N and T; X24 is selected
      from A and S; X25 is selected from G, R and W
<220> FEATURE:
<221> NAME/KEY: misc_feature
<222> LOCATION: (27)..(27)
<223> OTHER INFORMATION: Xaa is selected from K and R
<220> FEATURE:
<221> NAME/KEY: misc_feature
<222> LOCATION: (32)..(33)
<223> OTHER INFORMATION: X32 is selected from D, N and W; and X33 is
      selected from K and S

<400> SEQUENCE: 37

Ala Glu Ala Lys Tyr Ala Lys Glu Arg Thr Xaa Ala Xaa Trp Glu Ile
1               5                   10                  15

Xaa Xaa Leu Pro Asn Leu Xaa Xaa Xaa Gln Xaa Gly Ala Phe Ile Xaa
```

```
                    20                  25                  30

Xaa Leu His Asp Asp Pro Ser Glu Ser Ser Glu Leu Leu Ser Glu Ala
        35                  40                  45

Lys Lys Leu Asn Lys Ser Gln Ala Pro Lys
        50                  55
```

<210> SEQ ID NO 38
<211> LENGTH: 58
<212> TYPE: PRT
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
<222> LOCATION: (11)..(11)
<223> OTHER INFORMATION: Xaa is selected from I, M, V and W
<220> FEATURE:
<221> NAME/KEY: misc_feature
<222> LOCATION: (13)..(13)
<223> OTHER INFORMATION: Xaa is selected from T and V;
<220> FEATURE:
<221> NAME/KEY: misc_feature
<222> LOCATION: (17)..(18)
<223> OTHER INFORMATION: X17 is selected from M and V; X18 is selected
      from D and Q;
<220> FEATURE:
<221> NAME/KEY: misc_feature
<222> LOCATION: (23)..(25)
<223> OTHER INFORMATION: X23 is selected from N and T; X24 is selected
      from A and S; X25 is selected from G, R and W
<220> FEATURE:
<221> NAME/KEY: misc_feature
<222> LOCATION: (27)..(27)
<223> OTHER INFORMATION: Xaa is selected from K and R
<220> FEATURE:
<221> NAME/KEY: misc_feature
<222> LOCATION: (32)..(33)
<223> OTHER INFORMATION: X32 is selected from D, N and W; and X33 is
      selected from K and S

<400> SEQUENCE: 38

```
Val Asp Ala Lys Tyr Ala Lys Glu Arg Thr Xaa Ala Xaa Trp Glu Ile
1               5                   10                  15

Xaa Xaa Leu Pro Asn Leu Xaa Xaa Xaa Gln Xaa Gly Ala Phe Ile Xaa
                20                  25                  30

Xaa Leu His Asp Asp Pro Ser Gln Ser Ser Glu Leu Leu Ala Glu Ala
        35                  40                  45

Lys Lys Leu Asn Asp Ala Gln Ala Pro Lys
        50                  55
```

<210> SEQ ID NO 39
<211> LENGTH: 58
<212> TYPE: PRT
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
<222> LOCATION: (11)..(11)
<223> OTHER INFORMATION: Xaa is selected from I, M, V and W
<220> FEATURE:
<221> NAME/KEY: misc_feature
<222> LOCATION: (13)..(13)
<223> OTHER INFORMATION: Xaa is selected from T and V;
<220> FEATURE:
<221> NAME/KEY: misc_feature
<222> LOCATION: (17)..(18)
<223> OTHER INFORMATION: X17 is selected from M and V; X18 is selected
      from D and Q;
<220> FEATURE:
<221> NAME/KEY: misc_feature

```
<222> LOCATION: (23)..(25)
<223> OTHER INFORMATION: X23 is selected from N and T; X24 is selected
      from A and S; X25 is selected from G, R and W
<220> FEATURE:
<221> NAME/KEY: misc_feature
<222> LOCATION: (27)..(27)
<223> OTHER INFORMATION: Xaa is selected from K and R
<220> FEATURE:
<221> NAME/KEY: misc_feature
<222> LOCATION: (32)..(33)
<223> OTHER INFORMATION: X32 is selected from D, N and W; and X33 is
      selected from K and S

<400> SEQUENCE: 39

Val Asp Ala Lys Tyr Ala Lys Glu Arg Thr Xaa Ala Xaa Trp Glu Ile
1               5                   10                  15

Xaa Xaa Leu Pro Asn Leu Xaa Xaa Xaa Gln Xaa Gly Ala Phe Ile Xaa
            20                  25                  30

Xaa Leu His Asp Asp Pro Ser Gln Ser Ser Glu Leu Leu Ala Glu Ala
        35                  40                  45

Lys Lys Leu Asn Asp Ser Gln Ala Pro Lys
    50                  55

<210> SEQ ID NO 40
<211> LENGTH: 58
<212> TYPE: PRT
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
<222> LOCATION: (11)..(11)
<223> OTHER INFORMATION: Xaa is selected from I, M, V and W
<220> FEATURE:
<221> NAME/KEY: misc_feature
<222> LOCATION: (13)..(13)
<223> OTHER INFORMATION: Xaa is selected from T and V;
<220> FEATURE:
<221> NAME/KEY: misc_feature
<222> LOCATION: (17)..(18)
<223> OTHER INFORMATION: X17 is selected from M and V; X18 is selected
      from D and Q;
<220> FEATURE:
<221> NAME/KEY: misc_feature
<222> LOCATION: (23)..(25)
<223> OTHER INFORMATION: X23 is selected from N and T; X24 is selected
      from A and S; X25 is selected from G, R and W
<220> FEATURE:
<221> NAME/KEY: misc_feature
<222> LOCATION: (27)..(27)
<223> OTHER INFORMATION: Xaa is selected from K and R
<220> FEATURE:
<221> NAME/KEY: misc_feature
<222> LOCATION: (32)..(33)
<223> OTHER INFORMATION: X32 is selected from D, N and W; and X33 is
      selected from K and S

<400> SEQUENCE: 40

Ala Glu Ala Lys Tyr Ala Lys Glu Arg Thr Xaa Ala Xaa Trp Glu Ile
1               5                   10                  15

Xaa Xaa Leu Pro Asn Leu Xaa Xaa Xaa Gln Xaa Gly Ala Phe Ile Xaa
            20                  25                  30

Xaa Leu His Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 41
<211> LENGTH: 57
```

```
<212> TYPE: PRT
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
<222> LOCATION: (11)..(11)
<223> OTHER INFORMATION: Xaa is selected from I, M, V and W
<220> FEATURE:
<221> NAME/KEY: misc_feature
<222> LOCATION: (13)..(13)
<223> OTHER INFORMATION: Xaa is selected from T and V;
<220> FEATURE:
<221> NAME/KEY: misc_feature
<222> LOCATION: (17)..(18)
<223> OTHER INFORMATION: X17 is selected from M and V; X18 is selected
      from D and Q;
<220> FEATURE:
<221> NAME/KEY: misc_feature
<222> LOCATION: (23)..(25)
<223> OTHER INFORMATION: X23 is selected from N and T; X24 is selected
      from A and S; X25 is selected from G, R and W
<220> FEATURE:
<221> NAME/KEY: misc_feature
<222> LOCATION: (27)..(27)
<223> OTHER INFORMATION: Xaa is selected from K and R
<220> FEATURE:
<221> NAME/KEY: misc_feature
<222> LOCATION: (32)..(33)
<223> OTHER INFORMATION: X32 is selected from D, N and W; and X33 is
      selected from K and S

<400> SEQUENCE: 41

Ala Glu Ala Lys Tyr Ala Lys Glu Arg Thr Xaa Ala Xaa Trp Glu Ile
1               5                   10                  15

Xaa Xaa Leu Pro Asn Leu Xaa Xaa Xaa Gln Xaa Gly Ala Phe Ile Xaa
            20                  25                  30

Xaa Leu His Asp Asp Pro Ser Gln Ser Ser Glu Leu Leu Ser Glu Ala
        35                  40                  45

Lys Lys Leu Asn Asp Ser Gln Ala Pro
    50                  55

<210> SEQ ID NO 42
<211> LENGTH: 58
<212> TYPE: PRT
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
<222> LOCATION: (11)..(11)
<223> OTHER INFORMATION: Xaa is selected from I, M, V and W
<220> FEATURE:
<221> NAME/KEY: misc_feature
<222> LOCATION: (13)..(13)
<223> OTHER INFORMATION: Xaa is selected from T and V;
<220> FEATURE:
<221> NAME/KEY: misc_feature
<222> LOCATION: (17)..(18)
<223> OTHER INFORMATION: X17 is selected from M and V; X18 is selected
      from D and Q;
<220> FEATURE:
<221> NAME/KEY: misc_feature
<222> LOCATION: (23)..(25)
<223> OTHER INFORMATION: X23 is selected from N and T; X24 is selected
      from A and S; X25 is selected from G, R and W
<220> FEATURE:
<221> NAME/KEY: misc_feature
<222> LOCATION: (27)..(27)
<223> OTHER INFORMATION: Xaa is selected from K and R
<220> FEATURE:
<221> NAME/KEY: misc_feature
<222> LOCATION: (32)..(33)
<223> OTHER INFORMATION: X32 is selected from D, N and W; and X33 is
``` selected from K and S

<400> SEQUENCE: 42

Ala Glu Ala Lys Phe Ala Lys Glu Arg Thr Xaa Ala Xaa Trp Glu Ile
1               5                   10                  15

Xaa Xaa Leu Pro Asn Leu Xaa Xaa Xaa Gln Xaa Gly Ala Phe Ile Xaa
            20                  25                  30

Xaa Leu His Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 43
<211> LENGTH: 57
<212> TYPE: PRT
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
<222> LOCATION: (11)..(11)
<223> OTHER INFORMATION: Xaa is selected from I, M, V and W
<220> FEATURE:
<221> NAME/KEY: misc_feature
<222> LOCATION: (13)..(13)
<223> OTHER INFORMATION: Xaa is selected from T and V;
<220> FEATURE:
<221> NAME/KEY: misc_feature
<222> LOCATION: (17)..(18)
<223> OTHER INFORMATION: X17 is selected from M and V; X18 is selected
      from D and Q;
<220> FEATURE:
<221> NAME/KEY: misc_feature
<222> LOCATION: (23)..(25)
<223> OTHER INFORMATION: X23 is selected from N and T; X24 is selected
      from A and S; X25 is selected from G, R and W
<220> FEATURE:
<221> NAME/KEY: misc_feature
<222> LOCATION: (27)..(27)
<223> OTHER INFORMATION: Xaa is selected from K and R
<220> FEATURE:
<221> NAME/KEY: misc_feature
<222> LOCATION: (32)..(33)
<223> OTHER INFORMATION: X32 is selected from D, N and W; and X33 is
      selected from K and S

<400> SEQUENCE: 43

Ala Glu Ala Lys Phe Ala Lys Glu Arg Thr Xaa Ala Xaa Trp Glu Ile
1               5                   10                  15

Xaa Xaa Leu Pro Asn Leu Xaa Xaa Xaa Gln Xaa Gly Ala Phe Ile Xaa
            20                  25                  30

Xaa Leu His Asp Asp Pro Ser Gln Ser Ser Glu Leu Leu Ser Glu Ala
        35                  40                  45

Lys Lys Leu Asn Asp Ser Gln Ala Pro
    50                  55

<210> SEQ ID NO 44
<211> LENGTH: 58
<212> TYPE: PRT
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
<222> LOCATION: (11)..(11)
<223> OTHER INFORMATION: Xaa is selected from I, M, V and W
<220> FEATURE:
<221> NAME/KEY: misc_feature
<222> LOCATION: (13)..(13)

```
<223> OTHER INFORMATION: Xaa is selected from T and V;
<220> FEATURE:
<221> NAME/KEY: misc_feature
<222> LOCATION: (17)..(18)
<223> OTHER INFORMATION: X17 is selected from M and V; X18 is selected
      from D and Q;
<220> FEATURE:
<221> NAME/KEY: misc_feature
<222> LOCATION: (23)..(25)
<223> OTHER INFORMATION: X23 is selected from N and T; X24 is selected
      from A and S; X25 is selected from G, R and W
<220> FEATURE:
<221> NAME/KEY: misc_feature
<222> LOCATION: (27)..(27)
<223> OTHER INFORMATION: Xaa is selected from K and R
<220> FEATURE:
<221> NAME/KEY: misc_feature
<222> LOCATION: (32)..(33)
<223> OTHER INFORMATION: X32 is selected from D, N and W; and X33 is
      selected from K and S

<400> SEQUENCE: 44

Ala Glu Ala Lys Tyr Ala Lys Glu Arg Thr Xaa Ala Xaa Trp Glu Ile
1               5                   10                  15

Xaa Xaa Leu Pro Asn Leu Xaa Xaa Xaa Gln Xaa Gly Ala Phe Ile Xaa
            20                  25                  30

Xaa Leu His Asp Asp Pro Ser Gln Ser Ser Glu Leu Leu Ala Glu Ala
        35                  40                  45

Lys Lys Leu Asn Asp Ala Gln Ala Pro Lys
        50                  55

<210> SEQ ID NO 45
<211> LENGTH: 58
<212> TYPE: PRT
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
<222> LOCATION: (11)..(11)
<223> OTHER INFORMATION: Xaa is selected from I, M, V and

```
                  35                  40                  45

Lys Lys Leu Ser Glu Ser Gln Ala Pro Lys
    50                  55

<210> SEQ ID NO 46
<211> LENGTH: 57
<212> TYPE: PRT
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
<222> LOCATION: (11)..(11)
<223> OTHER INFORMATION: Xaa is selected from I, M, V and W
<220> FEATURE:
<221> NAME/KEY: misc_feature
<222> LOCATION: (13)..(13)
<223> OTHER INFORMATION: Xaa is selected from T and V;
<220> FEATURE:
<221> NAME/KEY: misc_feature
<222> LOCATION: (17)..(18)
<223> OTHER INFORMATION: X17 is selected from M and V; X18 is selected
      from D and Q;
<220> FEATURE:
<221> NAME/KEY: misc_feature
<222> LOCATION: (23)..(25)
<223> OTHER INFORMATION: X23 is selected from N and T; X24 is selected
      from A and S; X25 is selected from G, R and W
<220> FEATURE:
<221> NAME/KEY: misc_feature
<222> LOCATION: (27)..(27)
<223> OTHER INFORMATION: Xaa is selected from K and R
<220> FEATURE:
<221> NAME/KEY: misc_feature
<222> LOCATION: (32)..(33)
<223> OTHER INFORMATION: X32 is selected from D, N and W; and X33 is
      selected from K and S

<400> SEQUENCE: 46

Ala Glu Ala Lys Tyr Ala Lys Glu Arg Thr Xaa Ala Xaa Trp Glu Ile
1               5                  10                  15

Xaa Xaa Leu Pro Asn Leu Xaa Xaa Xaa Gln Xaa Gly Ala Phe Ile Xaa
            20                  25                  30

Xaa Leu His Asp Asp Pro Ser Gln Ser Ser Glu Leu Leu Ser Glu Ala
        35                  40                  45

Lys Lys Leu Ser Glu Ser Gln Ala Pro
    50                  55

<210> SEQ ID NO 47
<211> LENGTH: 58
<212> TYPE: PRT
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
<222> LOCATION: (11)..(11)
<223> OTHER INFORMATION: Xaa is selected from I, M, V and W
<220> FEATURE:
<221> NAME/KEY: misc_feature
<222> LOCATION: (13)..(13)
<223> OTHER INFORMATION: Xaa is selected from T and V;
<220> FEATURE:
<221> NAME/KEY: misc_feature
<222> LOCATION: (17)..(18)
<223> OTHER INFORMATION: X17 is selected from M and V; X18 is selected
      from D and Q;
<220> FEATURE:
<221> NAME/KEY: misc_feature
<222> LOCATION: (23)..(25)
<223> OTHER INFORMATION: X23 is selected from N and T; X24 is selected
      from A and S; X25 is selected from G, R and W
```

```
<220> FEATURE:
<221> NAME/KEY: misc_feature
<222> LOCATION: (27)..(27)
<223> OTHER INFORMATION: Xaa is selected from K and R
<220> FEATURE:
<221> NAME/KEY: misc_feature
<222> LOCATION: (32)..(33)
<223> OTHER INFORMATION: X32 is selected from D, N and W; and X33 is
      selected from K and S

<400> SEQUENCE: 47

Ala Glu Ala Lys Phe Ala Lys Glu Arg Thr Xaa Ala Xaa Trp Glu Ile
1               5                   10                  15

Xaa Xaa Leu Pro Asn Leu Xaa Xaa Xaa Gln Xaa Gly Ala Phe Ile Xaa
            20                  25                  30

Xaa Leu His Asp Asp Pro Ser Gln Ser Ser Glu Leu Leu Ser Glu Ala
        35                  40                  45

Lys Lys Leu Ser Glu Ser Gln Ala Pro Lys
    50                  55

<210> SEQ ID NO 48
<211> LENGTH: 57
<212> TYPE: PRT
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
<222> LOCATION: (11)..(11)
<223> OTHER INFORMATION: Xaa is selected from I, M, V and W
<220> FEATURE:
<221> NAME/KEY: misc_feature
<222> LOCATION: (13)..(13)
<223> OTHER INFORMATION: Xaa is selected from T and V;
<220> FEATURE:
<221> NAME/KEY: misc_feature
<222> LOCATION: (17)..(18)
<223> OTHER INFORMATION: X17 is selected from M and V; X18 is selected
      from D and Q;
<220> FEATURE:
<221> NAME/KEY: misc_feature
<222> LOCATION: (23)..(25)
<223> OTHER INFORMATION: X23 is selected from N and T; X24 is selected
      from A and S; X25 is selected from G, R and W
<220> FEATURE:
<221> NAME/KEY: misc_feature
<222> LOCATION: (27)..(27)
<223> OTHER INFORMATION: Xaa is selected from K and R
<220> FEATURE:
<221> NAME/KEY: misc_feature
<222> LOCATION: (32)..(33)
<223> OTHER INFORMATION: X32 is selected from D, N and W; and X33 is
      selected from K and S

<400> SEQUENCE: 48

Ala Glu Ala Lys Phe Ala Lys Glu Arg Thr Xaa Ala Xaa Trp Glu Ile
1               5                   10                  15

Xaa Xaa Leu Pro Asn Leu Xaa Xaa Xaa Gln Xaa Gly Ala Phe Ile Xaa
            20                  25                  30

Xaa Leu His Asp Asp Pro Ser Gln Ser Ser Glu Leu Leu Ser Glu Ala
        35                  40                  45

Lys Lys Leu Ser Glu Ser Gln Ala Pro
    50                  55

<210> SEQ ID NO 49
<211> LENGTH: 58
<212> TYPE: PRT
<213> ORGANISM: ARTIFICIAL SEQUENCE
<220> FEATURE:
```

<223> OTHER INFORMATION: Engineered PDL1 binding polypeptide
<220> FEATURE:
<221> NAME/KEY: misc_feature
<222> LOCATION: (11)..(11)
<223> OTHER INFORMATION: Xaa is selected from I, M, V and W
<220> FEATURE:
<221> NAME/KEY: misc_feature
<222> LOCATION: (13)..(13)
<223> OTHER INFORMATION: Xaa is selected from T and V;
<220> FEATURE:
<221> NAME/KEY: misc_feature
<222> LOCATION: (17)..(18)
<223> OTHER INFORMATION: X17 is selected from M and V; X18 is selected
      from D and Q;
<220> FEATURE:
<221> NAME/KEY: misc_feature
<222> LOCATION: (23)..(25)
<223> OTHER INFORMATION: X23 is selected from N and T; X24 is selected
      from A and S; X25 is selected from G, R and W
<220> FEATURE:
<221> NAME/KEY: misc_feature
<222> LOCATION: (27)..(27)
<223> OTHER INFORMATION: Xaa is selected from K and R
<220> FEATURE:
<221> NAME/KEY: misc_feature
<222> LOCATION: (32)..(33)
<223> OTHER INFORMATION: X32 is selected from D, N and W; and X33 is
      selected from K and S

<400> SEQUENCE: 49

Ala Glu Ala Lys Tyr Ala Lys Glu Arg Thr Xaa Ala Xaa Trp Glu Ile
1               5                   10                  15

Xaa Xaa Leu Pro Asn Leu Xaa Xaa Xaa Gln Xaa Gly Ala Phe Ile Xaa
            20                  25                  30

Xaa Leu His Asp Asp Pro Ser Gln Ser Ser Glu Leu Leu Ala Glu Ala
        35                  40                  45

Lys Lys Leu Ser Glu Ala Gln Ala Pro Lys
    50                  55

<210> SEQ ID NO 50
<211> LENGTH: 58
<212> TYPE: PRT
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
<222> LOCATION: (11)..(11)
<223> OTHER INFORMATION: Xaa is selected from I, M, V and W
<220> FEATURE:
<221> NAME/KEY: misc_feature
<222> LOCATION: (13)..(13)
<223> OTHER INFORMATION: Xaa is selected from T and V;
<220> FEATURE:
<221> NAME/KEY: misc_feature
<222> LOCATION: (17)..(18)
<223> OTHER INFORMATION: X17 is selected from M and V; X18 is selected
      from D and Q;
<220> FEATURE:
<221> NAME/KEY: misc_feature
<222> LOCATION: (23)..(25)
<223> OTHER INFORMATION: X23 is selected from N and T; X24 is selected
      from A and S; X25 is selected from G, R and W
<220> FEATURE:
<221> NAME/KEY: misc_feature
<222> LOCATION: (27)..(27)
<223> OTHER INFORMATION: Xaa is selected from K and R
<220> FEATURE:
<221> NAME/KEY: misc_feature
<222> LOCATION: (32)..(33)
<223> OTHER INFORMATION: X32 is selected from D, N and W; and X33 is
      selected from K and S

<400> SEQUENCE: 50

Ala Glu Ala Lys Tyr Ala Lys Glu Arg Thr Xaa Ala Xaa Trp Glu Ile
1               5                   10                  15

Xaa Xaa Leu Pro Asn Leu Xaa Xaa Xaa Gln Xaa Gly Ala Phe Ile Xaa
            20                  25                  30

Xaa Leu His Asp Gln Pro Glu Gln Ser Ser Glu Leu Leu Ser Glu Ala
        35                  40                  45

Lys Lys Leu Ser Glu Ser Gln Ala Pro Lys
    50                  55

<210> SEQ ID NO 51
<211> LENGTH: 58
<212> TYPE: PRT
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
<222> LOCATION: (11)..(11)
<223> OTHER INFORMATION: Xaa is selected from I, M, V and W
<220> FEATURE:
<221> NAME/KEY: misc_feature
<222> LOCATION: (13)..(13)
<223> OTHER INFORMATION: Xaa is selected from T and V;
<220> FEATURE:
<221> NAME/KEY: misc_feature
<222> LOCATION: (17)..(18)
<223> OTHER INFORMATION: X17 is selected from M and V; X18 is selected
      from D and Q;
<220> FEATURE:
<221> NAME/KEY: misc_feature
<222> LOCATION: (23)..(25)
<223> OTHER INFORMATION: X23 is selected from N and T; X24 is selected
      from A and S; X25 is selected from G, R and W
<220> FEATURE:
<221> NAME/KEY: misc_feature
<222> LOCATION: (27)..(27)
<223> OTHER INFORMATION: Xaa is selected from K and R
<220> FEATURE:
<221> NAME/KEY: misc_feature
<222> LOCATION: (32)..(33)
<223> OTHER INFORMATION: X32 is selected from D, N and W; and X33 is
      selected from K and S

<400> SEQUENCE: 51

Ala Glu Ala Lys Tyr Ala Lys Glu Arg Thr Xaa Ala Xaa Trp Glu Ile
1               5                   10                  15

Xaa Xaa Leu Pro Asn Leu Xaa Xaa Xaa Gln Xaa Gly Ala Phe Ile Xaa
            20                  25                  30

Xaa Leu His Asp Asp Pro Ser Gln Ser Ser Glu Leu Leu Ser Glu Ala
        35                  40                  45

Lys Lys Leu Glu Ser Ser Gln Ala Pro Lys
    50                  55

<210> SEQ ID NO 52
<211> LENGTH: 57
<212> TYPE: PRT
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
<222> LOCATION: (11)..(11)
<223> OTHER INFORMATION: Xaa is selected from I, M, V and W
<220> FEATURE:
<221> NAME/KEY: misc_feature
<222> LOCATION: (13)..(13)
<223> OTHER INFORMATION: Xaa is selected from T and V;
<220> FEATURE:
<221> NAME/KEY: misc_feature
<222> LOCATION: (17)..(18)
<223> OTHER INFORMATION: X17 is selected from M and V; X18 is selected
      from D and Q;
<220> FEATURE:
<221> NAME/KEY: misc_feature
<222> LOCATION: (23)..(25)
<223> OTHER INFORMATION: X23 is selected from N and T; X24 is selected
      from A and S; X25 is selected from G, R and W
<220> FEATURE:
<221> NAME/KEY: misc_feature
<222> LOCATION: (27)..(27)
<223> OTHER INFORMATION: Xaa is selected from K and R
<220> FEATURE:
<221> NAME/KEY: misc_feature
<222> LOCATION: (32)..(33)
<223> OTHER INFORMATION: X32 is selected from D, N and W; and X33 is
      selected from K and S

<400> SEQUENCE: 52

Ala Glu Ala Lys Tyr Ala Lys Glu Arg Thr Xaa Ala Xaa Trp Glu Ile
1               5                   10                  15

Xaa Xaa Leu Pro Asn Leu Xaa Xaa Xaa Gln Xaa Gly Ala Phe Ile Xaa
            20                  25                  30

Xaa Leu His Asp Asp Pro Ser Gln Ser Ser Glu Leu Leu Ser Glu Ala
        35                  40                  45

Lys Lys Leu Glu Ser Ser Gln Ala Pro
    50                  55

<210> SEQ ID NO 53
<211> LENGTH: 58
<212> TYPE: PRT
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
<222> LOCATION: (11)..(11)
<223> OTHER INFORMATION: Xaa is selected from I, M, V and W
<220> FEATURE:
<221> NAME/KEY: misc_feature
<222> LOCATION: (13)..(13)
<223> OTHER INFORMATION: Xaa is selected from T and V;
<220> FEATURE:
<221> NAME/KEY: misc_feature
<222> LOCATION: (17)..(18)
<223> OTHER INFORMATION: X17 is selected from M and V; X18 is selected
      from D and Q;
<220> FEATURE:
<221> NAME/KEY: misc_feature
<222> LOCATION: (23)..(25)
<223> OTHER INFORMATION: X23 is selected from N and T; X24 is selected
      from A and S; X25 is selected from G, R and W
<220> FEATURE:
<221> NAME/KEY: misc_feature
<222> LOCATION: (27)..(27)
<223> OTHER INFORMATION: Xaa is selected from K and R
<220> FEATURE:
<221> NAME/KEY: misc_feature
<222> LOCATION: (32)..(33)
<223> OTHER INFORMATION: X32 is selected from D, N and W; and X33 is
      selected from K and S

<400> SEQUENCE: 53

Ala Glu Ala Lys Tyr Ala Lys Glu Arg Thr Xaa Ala Xaa Trp Glu Ile
1               5                   10                  15

Xaa Xaa Leu Pro Asn Leu Xaa Xaa Xaa Gln Xaa Gly Ala Phe Ile Xaa
            20                  25                  30

Xaa Leu His Asp Asp Pro Ser Gln Ser Ser Glu Leu Leu Ala Glu Ala
        35                  40                  45

Lys Lys Leu Glu Ser Ala Gln Ala Pro Lys

```
                 50                  55

<210> SEQ ID NO 54
<211> LENGTH: 58
<212> TYPE: PRT
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
<222> LOCATION: (11)..(11)
<223> OTHER INFORMATION: Xaa is selected from I, M, V and W
<220> FEATURE:
<221> NAME/KEY: misc_feature
<222> LOCATION: (13)..(13)
<223> OTHER INFORMATION: Xaa is selected from T and V;
<220> FEATURE:
<221> NAME/KEY: misc_feature
<222> LOCATION: (17)..(18)
<223> OTHER INFORMATION: X17 is selected from M and V; X18 is selected
      from D and Q;
<220> FEATURE:
<221> NAME/KEY: misc_feature
<222> LOCATION: (23)..(25)
<223> OTHER INFORMATION: X23 is selected from N and T; X24 is selected
      from A and S; X25 is selected from G, R and W
<220> FEATURE:
<221> NAME/KEY: misc_feature
<222> LOCATION: (27)..(27)
<223> OTHER INFORMATION: Xaa is selected from K and R
<220> FEATURE:
<221> NAME/KEY: misc_feature
<222> LOCATION: (32)..(33)
<223> OTHER INFORMATION: X32 is selected from D, N and W; and X33 is
      selected from K and S

<400> SEQUENCE: 54

Ala Glu Ala Lys Tyr Ala Lys Glu Arg Thr Xaa Ala Xaa Trp Glu Ile
1               5                   10                  15

Xaa Xaa Leu Pro Asn Leu Xaa Xaa Xaa Gln Xaa Gly Ala Phe Ile Xaa
            20                  25                  30

Xaa Leu His Asp Gln Pro Glu Gln Ser Ser Glu Leu Leu Ser Glu Ala
        35                  40                  45

Lys Lys Leu Glu Ser Ser Gln Ala Pro Lys
    50                  55

<210> SEQ ID NO 55
<211> LENGTH: 58
<212> TYPE: PRT
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
<222> LOCATION: (11)..(11)
<223> OTHER INFORMATION: Xaa is selected from I, M, V and W
<220> FEATURE:
<221> NAME/KEY: misc_feature
<222> LOCATION: (13)..(13)
<223> OTHER INFORMATION: Xaa is selected from T and V;
<220> FEATURE:
<221> NAME/KEY: misc_feature
<222> LOCATION: (17)..(18)
<223> OTHER INFORMATION: X17 is selected from M and V; X18 is selected
      from D and Q;
<220> FEATURE:
<221> NAME/KEY: misc_feature
<222> LOCATION: (23)..(25)
<223> OTHER INFORMATION: X23 is selected from N and T; X24 is selected
      from A and S; X25 is selected from G, R and W
<220> FEATURE:
<221> NAME/KEY: misc_feature
<222> LOCATION: (27)..(27)
```

```
<223> OTHER INFORMATION: Xaa is selected from K and R
<220> FEATURE:
<221> NAME/KEY: misc_feature
<222> LOCATION: (32)..(33)
<223> OTHER INFORMATION: X32 is selected from D, N and W; and X33 is
      selected from K and S

<400> SEQUENCE: 55

Ala Glu Ala Lys Tyr Ala Lys Glu Arg Thr Xaa Ala Xaa Trp Glu Ile
1               5                   10                  15

Xaa Xaa Leu Pro Asn Leu Xaa Xaa Xaa Gln Xaa Gly Ala Phe Ile Xaa
            20                  25                  30

Xaa Leu His Asp Asp Pro Ser Gln Ser Ser Glu Leu Leu Ser Glu Ala
        35                  40                  45

Lys Lys Leu Ser Asp Ser Gln Ala Pro Lys
    50                  55

<210> SEQ ID NO 56
<211> LENGTH: 57
<212> TYPE: PRT
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
<222> LOCATION: (11)..(11)
<223> OTHER INFORMATION: Xaa is selected from I, M, V and W
<220> FEATURE:
<221> NAME/KEY: misc_feature
<222> LOCATION: (13)..(13)
<223> OTHER INFORMATION: Xaa is selected from T and V;
<220> FEATURE:
<221> NAME/KEY: misc_feature
<222> LOCATION: (17)..(18)
<223> OTHER INFORMATION: X17 is selected from M and V; X18 is selected
      from D and Q;
<220> FEATURE:
<221> NAME/KEY: misc_feature
<222> LOCATION: (23)..(25)
<223> OTHER INFORMATION: X23 is selected from N and T; X24 is selected
      from A and S; X25 is selected from G, R and W
<220> FEATURE:
<221> NAME/KEY: misc_feature
<222> LOCATION: (27)..(27)
<223> OTHER INFORMATION: Xaa is selected from K and R
<220> FEATURE:
<221> NAME/KEY: misc_feature
<222> LOCATION: (32)..(33)
<223> OTHER INFORMATION: X32 is selected from D, N and W; and X33 is
      selected from K and S

<400> SEQUENCE: 56

Ala Glu Ala Lys Tyr Ala Lys Glu Arg Thr Xaa Ala Xaa Trp Glu Ile
1               5                   10                  15

Xaa Xaa Leu Pro Asn Leu Xaa Xaa Xaa Gln Xaa Gly Ala Phe Ile Xaa
            20                  25                  30

Xaa Leu His Asp Asp Pro Ser Gln Ser Ser Glu Leu Leu Ser Glu Ala
        35                  40                  45

Lys Lys Leu Ser Asp Ser Gln Ala Pro
    50                  55

<210> SEQ ID NO 57
<211> LENGTH: 58
<212> TYPE: PRT
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
```

```
<222> LOCATION: (11)..(11)
<223> OTHER INFORMATION: Xaa is selected from I, M, V and W
<220> FEATURE:
<221> NAME/KEY: misc_feature
<222> LOCATION: (13)..(13)
<223> OTHER INFORMATION: Xaa is selected from T and V;
<220> FEATURE:
<221> NAME/KEY: misc_feature
<222> LOCATION: (17)..(18)
<223> OTHER INFORMATION: X17 is selected from M and V; X18 is selected
      from D and Q;
<220> FEATURE:
<221> NAME/KEY: misc_feature
<222> LOCATION: (23)..(25)
<223> OTHER INFORMATION: X23 is selected from N and T; X24 is selected
      from A and S; X25 is selected from G, R and W
<220> FEATURE:
<221> NAME/KEY: misc_feature
<222> LOCATION: (27)..(27)
<223> OTHER INFORMATION: Xaa is selected from K and R
<220> FEATURE:
<221> NAME/KEY: misc_feature
<222> LOCATION: (32)..(33)
<223> OTHER INFORMATION: X32 is selected from D, N and W; and X33 is
      selected from K and S

<400> SEQUENCE: 57

Ala Glu Ala Lys Tyr Ala Lys Glu Arg Thr Xaa Ala Xaa Trp Glu Ile
1               5                   10                  15

Xaa Xaa Leu Pro Asn Leu Xaa Xaa Xaa Gln Xaa Gly Ala Phe Ile Xaa
            20                  25                  30

Xaa Leu His Asp Asp Pro Ser Gln Ser Ser Glu Leu Leu Ala Glu Ala
        35                  40                  45

Lys Lys Leu Ser Asp Ser Gln Ala Pro Lys
    50                  55

<210> SEQ ID NO 58
<211> LENGTH: 58
<212> TYPE: PRT
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
<222> LOCATION: (11)..(11)
<223> OTHER INFORMATION: Xaa is selected from I, M, V and W
<220> FEATURE:
<221> NAME/KEY: misc_feature
<222> LOCATION: (13)..(13)
<223> OTHER INFORMATION: Xaa is selected from T and V;
<220> FEATURE:
<221> NAME/KEY: misc_feature
<222> LOCATION: (17)..(18)
<223> OTHER INFORMATION: X17 is selected from M and V; X18 is selected
      from D and Q;
<220> FEATURE:
<221> NAME/KEY: misc_feature
<222> LOCATION: (23)..(25)
<223> OTHER INFORMATION: X23 is selected from N and T; X24 is selected
      from A and S; X25 is selected from G, R and W
<220> FEATURE:
<221> NAME/KEY: misc_feature
<222> LOCATION: (27)..(27)
<223> OTHER INFORMATION: Xaa is selected from K and R
<220> FEATURE:
<221> NAME/KEY: misc_feature
<222> LOCATION: (32)..(33)
<223> OTHER INFORMATION: X32 is selected from D, N and W; and X33 is
      selected from K and S

<400> SEQUENCE: 58

Ala Glu Ala Lys Tyr Ala Lys Glu Arg Thr Xaa Ala Xaa Trp Glu Ile
1               5                   10                  15
```

```
Xaa Xaa Leu Pro Asn Leu Xaa Xaa Xaa Gln Xaa Gly Ala Phe Ile Xaa
            20                  25                  30

Xaa Leu His Asp Asp Pro Ser Gln Ser Ser Glu Leu Leu Ala Glu Ala
        35                  40                  45

Lys Lys Leu Ser Asp Ala Gln Ala Pro Lys
        50                  55

<210> SEQ ID NO 59
<211> LENGTH: 58
<212> TYPE: PRT
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
<222> LOCATION: (11)..(11)
<223> OTHER INFORMATION: Xaa is selected from I, M, V and W
<220> FEATURE:
<221> NAME/KEY: misc_feature
<222> LOCATION: (13)..(13)
<223> OTHER INFORMATION: Xaa is selected from T and V;
<220> FEATURE:
<221> NAME/KEY: misc_feature
<222> LOCATION: (17)..(18)
<223> OTHER INFORMATION: X17 is selected from M and V; X18 is selected
      from D and Q;
<220> FEATURE:
<221> NAME/KEY: misc_feature
<222> LOCATION: (23)..(25)
<223> OTHER INFORMATION: X23 is selected from N and T; X24 is selected
      from A and S; X25 is selected from G, R and W
<220> FEATURE:
<221> NAME/KEY: misc_feature
<222> LOCATION: (27)..(27)
<223> OTHER INFORMATION: Xaa is selected from K and R
<220> FEATURE:
<221> NAME/KEY: misc_feature
<222> LOCATION: (32)..(33)
<223> OTHER INFORMATION: X32 is selected from D, N and W; and X33 is
      selected from K and S

<400> SEQUENCE: 59

Ala Glu Ala Lys Tyr Ala Lys Glu Arg Thr Xaa Ala Xaa Trp Glu Ile
1               5                   10                  15

Xaa Xaa Leu Pro Asn Leu Xaa Xaa Xaa Gln Xaa Gly Ala Phe Ile Xaa
            20                  25                  30

Xaa Leu His Asp Gln Pro Glu Gln Ser Ser Glu Leu Leu Ser Glu Ala
        35                  40                  45

Lys Lys Leu Ser Asp Ser Gln Ala Pro Lys
        50                  55

<210> SEQ ID NO 60
<211> LENGTH: 58
<212> TYPE: PRT
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
<222> LOCATION: (11)..(11)
<223> OTHER INFORMATION: Xaa is selected from I, M, V and W
<220> FEATURE:
<221> NAME/KEY: misc_feature
<222> LOCATION: (13)..(13)
<223> OTHER INFORMATION: Xaa is selected from T and V;
<220> FEATURE:
<221> NAME/KEY: misc_feature
<222> LOCATION: (17)..(18)
<223> OTHER INFORMATION: X17 is selected from M and V; X18 is selected
      from D and Q;
```

```
<220> FEATURE:
<221> NAME/KEY: misc_feature
<222> LOCATION: (23)..(25)
<223> OTHER INFORMATION: X23 is selected from N and T; X24 is selected
      from A and S; X25 is selected from G, R and W
<220> FEATURE:
<221> NAME/KEY: misc_feature
<222> LOCATION: (27)..(27)
<223> OTHER INFORMATION: Xaa is selected from K and R
<220> FEATURE:
<221> NAME/KEY: misc_feature
<222> LOCATION: (32)..(33)
<223> OTHER INFORMATION: X32 is selected from D, N and W; and X33 is
      selected from K and S

<400> SEQUENCE: 60

Val Asp Ala Lys Tyr Ala Lys Glu Arg Thr Xaa Ala Xaa Trp Glu Ile
1               5                   10                  15

Xaa Xaa Leu Pro Asn Leu Xaa Xaa Xaa Gln Xaa Gly Ala Phe Ile Xaa
            20                  25                  30

Xaa Leu His Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 61
<211> LENGTH: 58
<212> TYPE: PRT
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
<222> LOCATION: (11)..(11)
<223> OTHER INFORMATION: Xaa is selected from I, M, V and W
<220> FEATURE:
<221> NAME/KEY: misc_feature
<222> LOCATION: (13)..(13)
<223> OTHER INFORMATION: Xaa is selected from T and V;
<220> FEATURE:
<221> NAME/KEY: misc_feature
<222> LOCATION: (17)..(18)
<223> OTHER INFORMATION: X17 is selected from M and V; X18 is selected
      from D and Q;
<220> FEATURE:
<221> NAME/KEY: misc_feature
<222> LOCATION: (23)..(25)
<223> OTHER INFORMATION: X23 is selected from N and T; X24 is selected
      from A and S; X25 is selected from G, R and W
<220> FEATURE:
<221> NAME/KEY: misc_feature
<222> LOCATION: (27)..(27)
<223> OTHER INFORMATION: Xaa is selected from K and R
<220> FEATURE:
<221> NAME/KEY: misc_feature
<222> LOCATION: (32)..(33)
<223> OTHER INFORMATION: X32 is selected from D, N and W; and X33 is
      selected from K and S

<400> SEQUENCE: 61

Val Asp Ala Lys Tyr Ala Lys Glu Arg Thr Xaa Ala Xaa Trp Glu Ile
1               5                   10                  15

Xaa Xaa Leu Pro Asn Leu Xaa Xaa Xaa Gln Xaa Gly Ala Phe Ile Xaa
            20                  25                  30

Xaa Leu His Asp Asp Pro Ser Gln Ser Ser Glu Leu Leu Ala Glu Ala
        35                  40                  45

Lys Lys Leu Asn Asp Ala Gln Ala Pro Lys
    50                  55
```

```
<210> SEQ ID NO 62
<211> LENGTH: 58
<212> TYPE: PRT
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
<222> LOCATION: (11)..(11)
<223> OTHER INFORMATION: Xaa is selected from I, M, V and W
<220> FEATURE:
<221> NAME/KEY: misc_feature
<222> LOCATION: (13)..(13)
<223> OTHER INFORMATION: Xaa is selected from T and V;
<220> FEATURE:
<221> NAME/KEY: misc_feature
<222> LOCATION: (17)..(18)
<223> OTHER INFORMATION: X17 is selected from M and V; X18 is selected
      from D and Q;
<220> FEATURE:
<221> NAME/KEY: misc_feature
<222> LOCATION: (23)..(25)
<223> OTHER INFORMATION: X23 is selected from N and T; X24 is selected
      from A and S; X25 is selected from G, R and W
<220> FEATURE:
<221> NAME/KEY: misc_feature
<222> LOCATION: (27)..(27)
<223> OTHER INFORMATION: Xaa is selected from K and R
<220> FEATURE:
<221> NAME/KEY: misc_feature
<222> LOCATION: (32)..(33)
<223> OTHER INFORMATION: X32 is selected from D, N and W; and X33 is
      selected from K and S

<400> SEQUENCE: 62

Val Asp Ala Lys Tyr Ala Lys Glu Arg Thr Xaa Ala Xaa Trp Glu Ile
1               5                   10                  15

Xaa Xaa Leu Pro Asn Leu Xaa Xaa Xaa Gln Xaa Gly Ala Phe Ile Xaa
            20                  25                  30

Xaa Leu His Asp Asp Pro Ser Gln Ser Ser Glu Leu Leu Ser Glu Ala
        35                  40                  45

Lys Lys Leu Ser Glu Ser Gln Ala Pro Lys
    50                  55

<210> SEQ ID NO 63
<211> LENGTH: 58
<212> TYPE: PRT
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
<222> LOCATION: (11)..(11)
<223> OTHER INFORMATION: Xaa is selected from I, M, V and W
<220> FEATURE:
<221> NAME/KEY: misc_feature
<222> LOCATION: (13)..(13)
<223> OTHER INFORMATION: Xaa is selected from T and V;
<220> FEATURE:
<221> NAME/KEY: misc_feature
<222> LOCATION: (17)..(18)
<223> OTHER INFORMATION: X17 is selected from M and V; X18 is selected
      from D and Q;
<220> FEATURE:
<221> NAME/KEY: misc_feature
<222> LOCATION: (23)..(25)
<223> OTHER INFORMATION: X23 is selected from N and T; X24 is selected
      from A and S; X25 is selected from G, R and W
<220> FEATURE:
<221> NAME/KEY: misc_feature
<222> LOCATION: (27)..(27)
<223> OTHER INFORMATION: Xaa is selected from K and R
<220> FEATURE:
<221> NAME/KEY: misc_feature
```

```
<222> LOCATION: (32)..(33)
<223> OTHER INFORMATION: X32 is selected from D, N and W; and X33 is
      selected from K and S

<400> SEQUENCE: 63

Val Asp Ala Lys Tyr Ala Lys Glu Arg Thr Xaa Ala Xaa Trp Glu Ile
1               5                   10                  15

Xaa Xaa Leu Pro Asn Leu Xaa Xaa Xaa Gln Xaa Gly Ala Phe Ile Xaa
            20                  25                  30

Xaa Leu His Asp Asp Pro Ser Gln Ser Ser Glu Leu Leu Ala Glu Ala
        35                  40                  45

Lys Lys Leu Ser Glu Ala Gln Ala Pro Lys
        50                  55

<210> SEQ ID NO 64
<211> LENGTH: 58
<212> TYPE: PRT
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
<222> LOCATION: (11)..(11)
<223> OTHER INFORMATION: Xaa is selected from I, M, V and W
<220> FEATURE:
<221> NAME/KEY: misc_feature
<222> LOCATION: (13)..(13)
<223> OTHER INFORMATION: Xaa is selected from T and V;
<220> FEATURE:
<221> NAME/KEY: misc_feature
<222> LOCATION: (17)..(18)
<223> OTHER INFORMATION: X17 is selected from M and V; X18 is selected
      from D and Q;
<220> FEATURE:
<221> NAME/KEY: misc_feature
<222> LOCATION: (23)..(25)
<223> OTHER INFORMATION: X23 is selected from N and T; X24 is selected
      from A and S; X25 is selected from G, R and W
<220> FEATURE:
<221> NAME/KEY: misc_feature
<222> LOCATION: (27)..(27)
<223> OTHER INFORMATION: Xaa is selected from K and R
<220> FEATURE:
<221> NAME/KEY: misc_feature
<222> LOCATION: (32)..(33)
<223> OTHER INFORMATION: X32 is selected from D, N and W; and X33 is
      selected from K and S

<400> SEQUENCE: 64

Val Asp Ala Lys Tyr Ala Lys Glu Arg Thr Xaa Ala Xaa Trp Glu Ile
1               5                   10                  15

Xaa Xaa Leu Pro Asn Leu Xaa Xaa Xaa Gln Xaa Gly Ala Phe Ile Xaa
            20                  25                  30

Xaa Leu His Asp Gln Pro Glu Gln Ser Ser Glu Leu Leu Ser Glu Ala
        35                  40                  45

Lys Lys Leu Ser Glu Ser Gln Ala Pro Lys
        50                  55

<210> SEQ ID NO 65
<211> LENGTH: 58
<212> TYPE: PRT
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
<222> LOCATION: (11)..(11)
<223> OTHER INFORMATION: Xaa is selected from I, M, V and W
<220> FEATURE:
```

```
<221> NAME/KEY: misc_feature
<222> LOCATION: (13)..(13)
<223> OTHER INFORMATION: Xaa is selected from T and V;
<220> FEATURE:
<221> NAME/KEY: misc_feature
<222> LOCATION: (17)..(18)
<223> OTHER INFORMATION: X17 is selected from M and V; X18 is selected
      from D and Q;
<220> FEATURE:
<221> NAME/KEY: misc_feature
<222> LOCATION: (23)..(25)
<223> OTHER INFORMATION: X23 is selected from N and T; X24 is selected
      from A and S; X25 is selected from G, R and W
<220> FEATURE:
<221> NAME/KEY: misc_feature
<222> LOCATION: (27)..(27)
<223> OTHER INFORMATION: Xaa is selected from K and R
<220> FEATURE:
<221> NAME/KEY: misc_feature
<222> LOCATION: (32)..(33)
<223> OTHER INFORMATION: X32 is selected from D, N and W; and X33 is
      selected from K and Sd

<400> SEQUENCE: 65

Val Asp Ala Lys Tyr Ala Lys Glu Arg Thr Xaa Ala Xaa Trp Glu Ile
1               5                   10                  15

Xaa Xaa Leu Pro Asn Leu Xaa Xaa Xaa Gln Xaa Gly Ala Phe Ile Xaa
            20                  25                  30

Xaa Leu His Asp Asp Pro Ser Gln Ser Ser Glu Leu Leu Ser Glu Ala
        35                  40                  45

Lys Lys Leu Glu Ser Ser Gln Ala Pro Lys
    50                  55

<210> SEQ ID NO 66
<211> LENGTH: 58
<212> TYPE: PRT
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
<222> LOCATION: (11)..(11)
<223> OTHER INFORMATION: Xaa is selected from I, M, V and W
<220> FEATURE:
<221> NAME/KEY: misc_feature
<222> LOCATION: (13)..(13)
<223> OTHER INFORMATION: Xaa is selected from T and V;
<220> FEATURE:
<221> NAME/KEY: misc_feature
<222> LOCATION: (17)..(18)
<223> OTHER INFORMATION: X17 is selected from M and V; X18 is selected
      from D and Q;
<220> FEATURE:
<221> NAME/KEY: misc_feature
<222> LOCATION: (23)..(25)
<223> OTHER INFORMATION: X23 is selected from N and T; X24 is selected
      from A and S; X25 is selected from G, R and W
<220> FEATURE:
<221> NAME/KEY: misc_feature
<222> LOCATION: (27)..(27)
<223> OTHER INFORMATION: Xaa is selected from K and R
<220> FEATURE:
<221> NAME/KEY: misc_feature
<222> LOCATION: (32)..(33)
<223> OTHER INFORMATION: X32 is selected from D, N and W; and X33 is
      selected from K and S

<400> SEQUENCE: 66

Val Asp Ala Lys Tyr Ala Lys Glu Arg Thr Xaa Ala Xaa Trp Glu Ile
1               5                   10                  15

Xaa Xaa Leu Pro Asn Leu Xaa Xaa Xaa Gln Xaa Gly Ala Phe Ile Xaa
            20                  25                  30
```

```
Xaa Leu His Asp Asp Pro Ser Gln Ser Ser Glu Leu Leu Ala Glu Ala
        35                  40                  45

Lys Lys Leu Glu Ser Ala Gln Ala Pro Lys
 50                  55

<210> SEQ ID NO 67
<211> LENGTH: 58
<212> TYPE: PRT
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
<222> LOCATION: (11)..(11)
<223> OTHER INFORMATION: Xaa is selected from I, M, V and W
<220> FEATURE:
<221> NAME/KEY: misc_feature
<222> LOCATION: (13)..(13)
<223> OTHER INFORMATION: Xaa is selected from T and V;
<220> FEATURE:
<221> NAME/KEY: misc_feature
<222> LOCATION: (17)..(18)
<223> OTHER INFORMATION: X17 is selected from M and V; X18 is selected
      from D and Q;
<220> FEATURE:
<221> NAME/KEY: misc_feature
<222> LOCATION: (23)..(25)
<223> OTHER INFORMATION: X23 is selected from N and T; X24 is selected
      from A and S; X25 is selected from G, R and W
<220> FEATURE:
<221> NAME/KEY: misc_feature
<222> LOCATION: (27)..(27)
<223> OTHER INFORMATION: Xaa is selected from K and R
<220> FEATURE:
<221> NAME/KEY: misc_feature
<222> LOCATION: (32)..(33)
<223> OTHER INFORMATION: X32 is selected from D, N and W; and X33 is
      selected from K and S

<400> SEQUENCE: 67

Val Asp Ala Lys Tyr Ala Lys Glu Arg Thr Xaa Ala Xaa Trp Glu Ile
 1               5                  10                  15

Xaa Xaa Leu Pro Asn Leu Xaa Xaa Xaa Gln Xaa Gly Ala Phe Ile Xaa
                20                  25                  30

Xaa Leu His Asp Gln Pro Glu Gln Ser Ser Glu Leu Leu Ser Glu Ala
        35                  40                  45

Lys Lys Leu Glu Ser Ser Gln Ala Pro Lys
 50                  55

<210> SEQ ID NO 68
<211> LENGTH: 58
<212> TYPE: PRT
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
<222> LOCATION: (11)..(11)
<223> OTHER INFORMATION: Xaa is selected from I, M, V and W
<220> FEATURE:
<221> NAME/KEY: misc_feature
<222> LOCATION: (13)..(13)
<223> OTHER INFORMATION: Xaa is selected from T and V;
<220> FEATURE:
<221> NAME/KEY: misc_feature
<222> LOCATION: (17)..(18)
<223> OTHER INFORMATION: X17 is selected from M and V; X18 is selected
      from D and Q;
<220> FEATURE:
<221> NAME/KEY: misc_feature
<222> LOCATION: (23)..(25)
```

<223> OTHER INFORMATION: X23 is selected from N and T; X24 is selected
      from A and S; X25 is selected from G, R and W
<220> FEATURE:
<221> NAME/KEY: misc_feature
<222> LOCATION: (27)..(27)
<223> OTHER INFORMATION: Xaa is selected from K and R
<220> FEATURE:
<221> NAME/KEY: misc_feature
<222> LOCATION: (32)..(33)
<223> OTHER INFORMATION: X32 is selected from D, N and W; and X33 is
      selected from K and S

<400> SEQUENCE: 68

Val Asp Ala Lys Tyr Ala Lys Glu Arg Thr Xaa Ala Xaa Trp Glu Ile
1               5                   10                  15

Xaa Xaa Leu Pro Asn Leu Xaa Xaa Xaa Gln Xaa Gly Ala Phe Ile Xaa
            20                  25                  30

Xaa Leu His Asp Asp Pro Ser Gln Ser Ser Glu Leu Leu Ser Glu Ala
        35                  40                  45

Lys Lys Leu Ser Asp Ser Gln Ala Pro Lys
        50                  55

<210> SEQ ID NO 69
<211> LENGTH: 58
<212> TYPE: PRT
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
<222> LOCATION: (11)..(11)
<223> OTHER INFORMATION: Xaa is selected from I, M, V and W
<220> FEATURE:
<221> NAME/KEY: misc_feature
<222> LOCATION: (13)..(13)
<223> OTHER INFORMATION: Xaa is selected from T and V;
<220> FEATURE:
<221> NAME/KEY: misc_feature
<222> LOCATION: (17)..(18)
<223> OTHER INFORMATION: X17 is selected from M and V; X18 is selected
      from D and Q;
<220> FEATURE:
<221> NAME/KEY: misc_feature
<222> LOCATION: (23)..(25)
<223> OTHER INFORMATION: X23 is selected from N and T; X24 is selected
      from A and S; X25 is selected from G, R and W
<220> FEATURE:
<221> NAME/KEY: misc_feature
<222> LOCATION: (27)..(27)
<223> OTHER INFORMATION: Xaa is selected from K and R
<220> FEATURE:
<221> NAME/KEY: misc_feature
<222> LOCATION: (32)..(33)
<223> OTHER INFORMATION: X32 is selected from D, N and W; and X33 is
      selected from K and S

<400> SEQUENCE: 69

Val Asp Ala Lys Tyr Ala Lys Glu Arg Thr Xaa Ala Xaa Trp Glu Ile
1               5                   10                  15

Xaa Xaa Leu Pro Asn Leu Xaa Xaa Xaa Gln Xaa Gly Ala Phe Ile Xaa
            20                  25                  30

Xaa Leu His Asp Asp Pro Ser Gln Ser Ser Glu Leu Leu Ala Glu Ala
        35                  40                  45

Lys Lys Leu Ser Asp Ser Gln Ala Pro Lys
        50                  55

<210> SEQ ID NO 70
<211> LENGTH: 58
<212> TYPE: PRT

```
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
<222> LOCATION: (11)..(11)
<223> OTHER INFORMATION: Xaa is selected from I, M, V and W
<220> FEATURE:
<221> NAME/KEY: misc_feature
<222> LOCATION: (13)..(13)
<223> OTHER INFORMATION: Xaa is selected from T and V;
<220> FEATURE:
<221> NAME/KEY: misc_feature
<222> LOCATION: (17)..(18)
<223> OTHER INFORMATION: X17 is selected from M and V; X18 is selected
      from D and Q;
<220> FEATURE:
<221> NAME/KEY: misc_feature
<222> LOCATION: (23)..(25)
<223> OTHER INFORMATION: X23 is selected from N and T; X24 is selected
      from A and S; X25 is selected from G, R and W
<220> FEATURE:
<221> NAME/KEY: misc_feature
<222> LOCATION: (27)..(27)
<223> OTHER INFORMATION: Xaa is selected from K and R
<220> FEATURE:
<221> NAME/KEY: misc_feature
<222> LOCATION: (32)..(33)
<223> OTHER INFORMATION: X32 is selected from D, N and W; and X33 is
      selected from K and S

<400> SEQUENCE: 70

Val Asp Ala Lys Tyr Ala Lys Glu Arg Thr Xaa Ala Xaa Trp Glu Ile
1               5                   10                  15

Xaa Xaa Leu Pro Asn Leu Xaa Xaa Xaa Gln Xaa Gly Ala Phe Ile Xaa
            20                  25                  30

Xaa Leu His Asp Asp Pro Ser Gln Ser Ser Glu Leu Leu Ala Glu Ala
        35                  40                  45

Lys Lys Leu Ser Asp Ala Gln Ala Pro Lys
    50                  55

<210> SEQ ID NO 71
<211> LENGTH: 58
<212> TYPE: PRT
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
<222> LOCATION: (11)..(11)
<223> OTHER INFORMATION: Xaa is selected from I, M, V and W
<220> FEATURE:
<221> NAME/KEY: misc_feature
<222> LOCATION: (13)..(13)
<223> OTHER INFORMATION: Xaa is selected from T and V;
<220> FEATURE:
<221> NAME/KEY: misc_feature
<222> LOCATION: (17)..(18)
<223> OTHER INFORMATION: X17 is selected from M and V; X18 is selected
      from D and Q;
<220> FEATURE:
<221> NAME/KEY: misc_feature
<222> LOCATION: (23)..(25)
<223> OTHER INFORMATION: X23 is selected from N and T; X24 is selected
      from A and S; X25 is selected from G, R and W
<220> FEATURE:
<221> NAME/KEY: misc_feature
<222> LOCATION: (27)..(27)
<223> OTHER INFORMATION: Xaa is selected from K and R
<220> FEATURE:
<221> NAME/KEY: misc_feature
<222> LOCATION: (32)..(33)
<223> OTHER INFORMATION: X32 is selected from D, N and W; and X33 is
      selected from K and S
```

-continued

<400> SEQUENCE: 71

Val Asp Ala Lys Tyr Ala Lys Glu Arg Thr Xaa Ala Xaa Trp Glu Ile
1               5                   10                  15

Xaa Xaa Leu Pro Asn Leu Xaa Xaa Xaa Gln Xaa Gly Ala Phe Ile Xaa
            20                  25                  30

Xaa Leu His Asp Gln Pro Glu Gln Ser Ser Glu Leu Leu Ser Glu Ala
        35                  40                  45

Lys Lys Leu Ser Asp Ser Gln Ala Pro Lys
    50                  55

<210> SEQ ID NO 72
<211> LENGTH: 58
<212> TYPE: PRT
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
<222> LOCATION: (11)..(11)
<223> OTHER INFORMATION: Xaa is selected from I, M, V and W
<220> FEATURE:
<221> NAME/KEY: misc_feature
<222> LOCATION: (13)..(13)
<223> OTHER INFORMATION: Xaa is selected from T and V;
<220> FEATURE:
<221> NAME/KEY: misc_feature
<222> LOCATION: (17)..(18)
<223> OTHER INFORMATION: X17 is selected from M and V; X18 is selected
      from D and Q;
<220> FEATURE:
<221> NAME/KEY: misc_feature
<222> LOCATION: (23)..(25)
<223> OTHER INFORMATION: X23 is selected from N and T; X24 is selected
      from A and S; X25 is selected from G, R and W
<220> FEATURE:
<221> NAME/KEY: misc_feature
<222> LOCATION: (27)..(27)
<223> OTHER INFORMATION: Xaa is selected from K and R
<220> FEATURE:
<221> NAME/KEY: misc_feature
<222> LOCATION: (32)..(33)
<223> OTHER INFORMATION: X32 is selected from D, N and W; and X33 is
      selected from K and S

<400> SEQUENCE: 72

Val Asp Ala Lys Tyr Ala Lys Glu Arg Thr Xaa Ala Xaa Trp Glu Ile
1               5                   10                  15

Xaa Xaa Leu Pro Asn Leu Xaa Xaa Xaa Gln Xaa Gly Ala Phe Ile Xaa
            20                  25                  30

Xaa Leu His Asp Asp Pro Ser Gln Ser Ser Glu Leu Leu Ala Glu Ala
        35                  40                  45

Lys Lys Leu Asn Lys Ala Gln Ala Pro Lys
    50                  55

<210> SEQ ID NO 73
<211> LENGTH: 58
<212> TYPE: PRT
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
<222> LOCATION: (11)..(11)
<223> OTHER INFORMATION: Xaa is selected from I, M, V and W
<220> FEATURE:
<221> NAME/KEY: misc_feature
<222> LOCATION: (13)..(13)
<223> OTHER INFORMATION: Xaa is selected from T and V;

```
<220> FEATURE:
<221> NAME/KEY: misc_feature
<222> LOCATION: (17)..(18)
<223> OTHER INFORMATION: X17 is selected from M and V; X18 is selected
      from D and Q;
<220> FEATURE:
<221> NAME/KEY: misc_feature
<222> LOCATION: (23)..(25)
<223> OTHER INFORMATION: X23 is selected from N and T; X24 is selected
      from A and S; X25 is selected from G, R and W
<220> FEATURE:
<221> NAME/KEY: misc_feature
<222> LOCATION: (27)..(27)
<223> OTHER INFORMATION: Xaa is selected from K and R
<220> FEATURE:
<221> NAME/KEY: misc_feature
<222> LOCATION: (32)..(33)
<223> OTHER INFORMATION: X32 is selected from D, N and W; and X33 is
      selected from K and S

<400> SEQUENCE: 73

Ala Glu Ala Lys Tyr Ala Lys Glu Arg Thr Xaa Ala Xaa Trp Glu Ile
1               5                   10                  15

Xaa Xaa Leu Pro Asn Leu Xaa Xaa Xaa Gln Xaa Gly Ala Phe Ile Xaa
            20                  25                  30

Xaa Leu His Asp Asp Pro Ser Gln Ser Ser Glu Leu Leu Ala Glu Ala
        35                  40                  45

Lys Lys Leu Asn Lys Ala Gln Ala Pro Lys
    50                  55

<210> SEQ ID NO 74
<211> LENGTH: 58
<212> TYPE: PRT
<213> ORGANISM: ARTIFICIAL SEQUENCE
<220> FEATURE:
<223> OTHER INFORMATION: Engineered PDL1 binding polypeptide
<220> FEATURE:
<221> NAME/KEY: misc_feature
<222> LOCATION: (11)..(11)
<223> OTHER INFORMATION: Xaa is selected from I, M, V and W
<220> FEATURE:
<221> NAME/KEY: misc_feature
<222> LOCATION: (13)..(13)
<223> OTHER INFORMATION: Xaa is selected from T and V;
<220> FEATURE:
<221> NAME/KEY: misc_feature
<222> LOCATION: (17)..(18)
<223> OTHER INFORMATION: X17 is selected from M and V; X18 is selected
      from D and Q;
<220> FEATURE:
<221> NAME/KEY: misc_feature
<222> LOCATION: (23)..(25)
<223> OTHER INFORMATION: X23 is selected from N and T; X24 is selected
      from A and S; X25 is selected from G, R and W
<220> FEATURE:
<221> NAME/KEY: misc_feature
<222> LOCATION: (27)..(27)
<223> OTHER INFORMATION: Xaa is selected from K and R
<220> FEATURE:
<221> NAME/KEY: misc_feature
<222> LOCATION: (32)..(33)
<223> OTHER INFORMATION: X32 is selected from D, N and W; and X33 is
      selected from K and S

<400> SEQUENCE: 74

Ala Asp Ala Lys Tyr Ala Lys Glu Arg Thr Xaa Ala Xaa Trp Glu Ile
1               5                   10                  15

Xaa Xaa Leu Pro Asn Leu Xaa Xaa Xaa Gln Xaa Gly Ala Phe Ile Xaa
            20                  25                  30

Xaa Leu His Asp Asp Pro Ser Gln Ser Ser Glu Leu Leu Ser Glu Ala
        35                  40                  45
```

Lys Lys Leu Asn Asp Ser Gln Ala Pro Lys
    50              55

<210> SEQ ID NO 75
<211> LENGTH: 5
<212> TYPE: PRT
<213> ORGANISM: artificial sequence
<220> FEATURE:
<223> OTHER INFORMATION: linker

<400> SEQUENCE: 75

Ser Ser Ser Ser Gly
1               5

<210> SEQ ID NO 76
<211> LENGTH: 15
<212> TYPE: PRT
<213> ORGANISM: artificial sequence
<220> FEATURE:
<223> OTHER INFORMATION: linker

<400> SEQUENCE: 76

Ser Ser Ser Ser Gly Ser Ser Ser Ser Gly Ser Ser Ser Ser Gly
1               5                   10                  15

<210> SEQ ID NO 77
<211> LENGTH: 20
<212> TYPE: PRT
<213> ORGANISM: artificial sequence
<220> FEATURE:
<223> OTHER INFORMATION: linker

<400> SEQUENCE: 77

Ser Ser Ser Ser Gly Ser Ser Ser Ser Gly Ser Ser Ser Ser Gly Ser
1               5                   10                  15

Ser Ser Ser Gly
            20

<210> SEQ ID NO 78
<211> LENGTH: 5
<212> TYPE: PRT
<213> ORGANISM: artificial sequence
<220> FEATURE:
<223> OTHER INFORMATION: linker

<400> SEQUENCE: 78

Gly Gly Gly Gly Ser
1               5

<210> SEQ ID NO 79
<211> LENGTH: 15
<212> TYPE: PRT
<213> ORGANISM: artificial sequence
<220> FEATURE:
<223> OTHER INFORMATION: linker

<400> SEQUENCE: 79

Gly Gly Gly Gly Ser Gly Gly Gly Gly Ser Gly Gly Gly Gly Ser
1               5                   10                  15

<210> SEQ ID NO 80
<211> LENGTH: 18
<212> TYPE: PRT
<213> ORGANISM: artificial sequence
<220> FEATURE:
<223> OTHER INFORMATION: Fusion of Z variant and ABD

```
<220> FEATURE:
<221> NAME/KEY: MISC_FEATURE
<222> LOCATION: (9)..(9)
<223> OTHER INFORMATION: X is a Z variant
<220> FEATURE:
<221> NAME/KEY: MISC_FEATURE
<222> LOCATION: (14)..(14)
<223> OTHER INFORMATION: X is an ABD

<400> SEQUENCE: 80

Ala Gln His Asp Glu Ala Leu Glu Xaa Val Asp Tyr Val Xaa Tyr Val
1               5                   10                  15

Pro Gly

<210> SEQ ID NO 81
<211> LENGTH: 15
<212> TYPE: PRT
<213> ORGANISM: artificial sequence
<220> FEATURE:
<223> OTHER INFORMATION: synthetic construct including Z variant
<220> FEATURE:
<221> NAME/KEY: MISC_FEATURE
<222> LOCATION: (13)..(13)
<223> OTHER INFORMATION: X is a Z variant

<400> SEQUENCE: 81

Met Gly Ser Ser His His His His His His Leu Gln Xaa Val Asp
1               5                   10                  15
```

POLYPEPTIDE

CROSS-REFERENCE TO RELATED APPLICATIONS

This application is the U.S. National Stage entry of International Application No. PCT/EP2016/076027 filed Oct. 28, 2016 which claims priority of European Patent Application No. 16157190.6 filed Feb. 24, 2016 and European Patent Application No. 15192367.9 filed Oct. 30, 2015. These application are incorporated by reference herein in their entireties.

FIELD OF THE INVENTION

The present disclosure relates to a class of engineered polypeptides having a binding affinity for programmed death-ligand 1 (in the following referred to as PD-L1). The present disclosure also relates to the use of such a PD-L1 binding polypeptide as a therapeutic, prognostic and/or diagnostic agent.

BACKGROUND

Under normal physiologic conditions, the immune checkpoints are crucial for maintaining self-tolerance (i.e. prevent autoimmunity) and for modulating the immune response to protect against tissue damage when the immune system is responding to pathogenic infections. At times, tumor cells can co-opt certain immune checkpoint pathways to escape from immunesurveillance mechanisms. Inhibition of immune checkpoints has therefore emerged as a promising approach in cancer immunotherapy. The two immune checkpoint receptors that have been most actively studied in this context are the cytotoxic T-lymphocyte-associated antigen (CTLA-4; also known as CD152) and programmed cell death protein 1 (PD-1; also known as CD279), which regulate the immune response at different levels. CTLA-4 primarily regulates immune responses early in T-cell activation, whereas PD-1 primarily limits the activity of T-cells in the effector phase within tissues and tumors (Pardoll, 2012, Nat. Rev. Cancer, 12:252-64).

PD-1 has two known ligands: programmed death-ligand 1 (PD-L1; also known as human B7 homolog 1, B7-H1, or cluster of differentiation 274, CD274) and programmed death-ligand 2 (PD-L2; also known as B7-DC and CD273). Both ligands belong to the B7 immunoglobulin superfamily and are type I transmembrane glycoproteins composed of IgC- and IgV-type extracellular domains. However, it was recently reported that PD-L1 and PD-L2, as well as PD-1, also exist in soluble forms in addition to being membrane bound. PD-L1 and PD-L2 share approximately 40% amino acid residue identity. Whereas the expression of PD-L2 is mainly limited to antigen presenting cells, PD-L1 is expressed in both hematopoietic and non-hematopoietic cells. High tumor expression of PD-L1 is associated with increased aggressiveness and worse prognosis (Dai et al, 2014, Cellular Immunology, 290:72-79).

The clinical significance of targeting immune checkpoint pathways has been demonstrated with several monoclonal antibodies inhibiting CTLA-4, PD-1 and PD-L1, which work by restoring protective immune responses to tumor cells. The anti-CTLA-4 antibody ipilimumab (Yervoy®, Bristol Myers Squibb) was approved by FDA in 2011 for the treatment patients with metastatic melanoma where a durable response was observed in 10-15% of the patients. However, ipilimumab is associated with immune-related toxicities, potentially due to its role in the priming phase of the immune response thereby also affecting normal tissues. A safer approach may be to target the PD-1/PD-L1 pathway to restore anti-tumor immunity selectively within the tumor microenvironment. Inhibition of the PD-1/PD-L1 pathway has demonstrated durable response in 30-35% of patients with advanced melanoma, which in 2014 resulted in the FDA approval of the anti-PD-1 antibodies pembrolizumab (formerly lambrolizumab; Keytruda®, Merck) and nivolumab (Bristol Myers Squibb and Ono Pharmaceutical) (Shin and Ribas, 2015, Curr. Opin. Immunol., 33:23-35; Philips and Atkins, 2015, International Immunology, 27:39-46). The first PD-L1 targeting antibody investigated in clinical trials was MDX-1105 which was evaluated in a Phase I study in patients with advanced solid tumors including melanoma, non-small cell lung cancer (NSCLC), colorectal cancer, renal cell carcinoma, ovarian cancer, pancreatic cancer, gastric cancer and breast cancer (Momtaz and Postow, 2014, Pharmgenomics Pers Med. 7:357-65). The results demonstrated potential benefits of PD-L1 blockade. Other antibodies against PD-L1 that are currently in Phase III clinical trials include atezolizumab (MDPL3280A, Genentech), durvalumab (MED14736, MedImmune/Astra Zeneca, Celgene), and avelumab (MSB0010718C, EMD Serono, Pfizer).

To improve the efficacy and increase the number of patients that respond to immunotherapy, it may be beneficial to target the antitumor immune response at multiple levels. This may be achieved through synergistic combinations. For instance, preclinical studies combining CTLA-4 and PD-1 blocking antibodies (ipilimumab and nivolumab) has demonstrated superior antitumor activity, but with a toxicity similar to anti-CTLA-4 monotherapy (Shin and Ribas, 2015, supra). Furthermore, PD-L1 is speculated to be a potential biomarker, due to its abundance in the tumor microenvironment and because tumor expression of PD-L1 has a strong association with response to anti-PD-1/PD-L1 therapy.

The high prevalence of cancer and infectious diseases, together with a high unmet medical need, warrants the development of new modes of treatment. Since tissue penetration rate is negatively associated with the size of the molecule, a relatively large antibody molecule inherently has poor tissue distribution and penetration capacity.

Thus, the use of monoclonal antibodies is not always optimal for therapy and there is continued need for provision of agents with a high affinity for PD-L1. Of great interest is also the provision of uses of such molecules in the treatment, diagnosis and prognosis of PD-L1 related disorders.

SUMMARY OF THE INVENTION

It is an object of the present disclosure to provide new PD-L1 binding agents, which could for example be used for therapeutic, prognostic and diagnostic applications.

It is an object of the present disclosure to provide a new multispecific agent, such as a bispecific agent, which has affinity for PD-L1 and at least one additional antigen.

It is an object of the present disclosure to provide a molecule allowing for efficient therapy of for example various forms of cancer and infectious disease, while alleviating the abovementioned and other drawbacks of current therapies.

It is an object of the present disclosure to provide a molecule suitable for prognostic and diagnostic applications, for example prognostic and diagnostic application in relation to various forms of cancer and infectious disease.

These and other objects, which are evident to the skilled person from the present disclosure, are met by the different aspects of the invention as claimed in the appended claims and as generally disclosed herein.

Thus, in the first aspect of the disclosure, there is provided a PD-L1 binding polypeptide, comprising a PD-L1 binding motif BM, which motif consists of an amino acid sequence selected from:

i)
(SEQ ID NO: 23)
ERTX$_4$AX$_6$WEIX$_{10}$X$_{11}$LPNLX$_{16}$X$_{17}$X$_{18}$QX$_{20}$GAFIX$_{25}$X$_{26}$LHD wherein, independently from each other,
X$_4$ is selected from I, M, V and W;
X$_6$ is selected from T and V;
X$_{10}$ is selected from M and V;
X$_{11}$ is selected from D and Q;
X$_{16}$ is selected from N and T;
X$_{17}$ is selected from A and S;
X$_{18}$ is selected from G, R and W;
X$_{20}$ is selected from K and R;
X$_{25}$ is selected from D, N and W; and
X$_{26}$ is selected from K and S;
and
ii) an amino acid sequence which has at least 89% identity to the sequence defined in i).

The above definition of a class of sequence related, PD-L1 binding polypeptides is based on a statistical analysis of a number of random polypeptide variants of a parent scaffold, that were selected for their interaction with PD-L1 in selection experiments. The identified PD-L1 binding motif, or "BM", corresponds to the target binding region of the parent scaffold, which region constitutes two alpha helices within a three-helical bundle protein domain. In the parent scaffold, the varied amino acid residues of the two BM helices constitute a binding surface for interaction with the constant Fc part of antibodies. In the present disclosure, the random variation of binding surface residues and subsequent selection of variants have replaced the Fc interaction capacity with a capacity for interaction with PD-L1.

As the skilled person will realize, the function of any polypeptide, such as the PD-L1 binding capacity of the polypeptide of the present disclosure, is dependent on the tertiary structure of the polypeptide. It is therefore possible to make minor changes to the sequence of amino acids in a polypeptide without affecting the function thereof. Thus, the disclosure encompasses modified variants of the PD-L1 binding polypeptide, which have retained PD-L1 binding characteristics.

In this way, encompassed by the present disclosure is a PD-L1 binding polypeptide comprising an amino acid sequence with 89% or greater identity to a polypeptide as defined in i). In some embodiments, said polypeptide may comprise a sequence which is at least 93%, such as at least 96% identical to a polypeptide as defined in i). For example, it is possible that an amino acid residue belonging to a certain functional grouping of amino acid residues (e.g. hydrophobic, hydrophilic, polar etc) could be exchanged for another amino acid residue from the same functional group.

In some embodiments, such changes may be made in any position of the sequence of the PD-L1 binding polypeptide as disclosed herein. In other embodiments, such changes may be made only in the non-variable positions, also denoted scaffold amino acid residues. In such cases, changes are not allowed in the variable positions. In other embodiments, such changes may be only in the variable positions.

According to one definition of such "variable positions", these are positions denoted with an "X" in sequence i) as defined above. According to another definition, "variable positions" are those positions that are randomized in a selection library of Z variants prior to selection, and may thus for example be positions 2, 3, 4, 6, 7, 10, 11, 17, 18, 20, 21, 25 and 28 in sequence i), as illustrated in Example 1.

The term "% identity", as used throughout the specification, may for example be calculated as follows. The query sequence is aligned to the target sequence using the CLUSTAL W algorithm (Thompson et al., (1994) Nucleic Acids Research, 22: 4673-4680). A comparison is made over the window corresponding to the shortest of the aligned sequences. The shortest of the aligned sequences may in some instances be the target sequence. In other instances, the query sequence may constitute the shortest of the aligned sequences. The amino acid residues at each position are compared and the percentage of positions in the query sequence that have identical correspondences in the target sequence is reported as % identity.

In another embodiment, there is provided a PD-L1 binding polypeptide wherein in sequence i)
X$_4$ is selected from I, M, V and W;
X$_6$ is selected from T and V;
X$_{10}$ is selected from M and V;
X$_{11}$ is selected from D and Q;
X$_{16}$ is T;
X$_{17}$ is selected from A and S;
X$_{18}$ is selected from G, R and W;
X$_{20}$ is selected from K and R;
X$_{25}$ is selected from D, N and W; and
X$_{26}$ is K.

As used herein, "X$_n$" and "X$_m$" are used to indicate amino acids in positions n and m in the sequence i) as defined above, wherein n and m are integers which indicate the position of an amino acid within said sequence as counted from the N-terminal end of said sequence. For example, X$_4$ and X$_6$ indicate the amino acid in position four and six, respectively, from the N-terminal end of sequence i).

In embodiments according to the first aspect, there are provided polypeptides wherein X$_n$ in sequence i) is independently selected from a group of possible residues according to Table 1. The skilled person will appreciate that X$_n$ may be selected from any one of the listed groups of possible residues and that this selection is independent from the selection of amino acids in X$_m$, wherein n≠m. Thus, any of the listed possible residues in position X$_n$ in Table 1 may be independently combined with any of the listed possible residues any other variable position in Table 1.

The skilled person will appreciate that Table 1 is to be read as follows: In one embodiment according to the first aspect, there is provided a polypeptide wherein amino acid residue "X$_n$" in sequence i) is selected from "Possible residues". Thus, Table 1 discloses several specific and individualized embodiments of the first aspect of the present disclosure. For example, in one embodiment according to the first aspect, there is provided a polypeptide wherein X$_4$ in sequence i) is selected from I, M, and V, and in another embodiment according to the first aspect, there is provided a polypeptide wherein X$_4$ in sequence i) is selected from M, V and W. For avoidance of doubt, the listed embodiments may be freely combined in yet other embodiments. For example, one such combined embodiment is a polypeptide in which X$_4$ is selected from I, V, and W, while X$_{18}$ is selected from G and W, and X$_{25}$ is selected from D and W.

TABLE 1

| $X_n$ | Possible residues |
|---|---|
| $X_4$ | I, M and V |
| $X_4$ | I, M and W |
| $X_4$ | I, V and W |
| $X_4$ | M, V and W |
| $X_4$ | I, M |
| $X_4$ | I, V |
| $X_4$ | I, W |
| $X_4$ | M, V |
| $X_4$ | M, W |
| $X_4$ | V, W |
| $X_4$ | I |
| $X_4$ | M |
| $X_4$ | V |
| $X_4$ | W |
| $X_6$ | T |
| $X_6$ | V |
| $X_{10}$ | M |
| $X_{10}$ | V |
| $X_{11}$ | D |
| $X_{11}$ | Q |
| $X_{16}$ | N |
| $X_{16}$ | T |
| $X_{17}$ | A |
| $X_{17}$ | S |
| $X_{18}$ | G, W |
| $X_{18}$ | R, W |
| $X_{18}$ | G, R |
| $X_{18}$ | G |
| $X_{18}$ | R |
| $X_{18}$ | W |
| $X_{20}$ | K |
| $X_{20}$ | R |
| $X_{25}$ | D, N |
| $X_{25}$ | D, W |
| $X_{25}$ | N, W |
| $X_{25}$ | D |
| $X_{25}$ | N |
| $X_{25}$ | W |
| $X_{26}$ | K |
| $X_{26}$ | S |

In one particular embodiment according to the first aspect, there is provided a polypeptide wherein sequence i) fulfills at least three of the six conditions I-VI:
I. $X_6$ is V;
II. $X_{16}$ is T;
III. $X_{17}$ is A;
IV. $X_{18}$ is W;
V. $X_{25}$ is N; and
VI. $X_{26}$ is K.

In one embodiment, sequence i) fulfills at least four of the six conditions I-VI, such as least five of the sin conditions I-VI. In one particular embodiment, sequence i) fulfills all of the six conditions I-VI.

In some embodiments of a PD-L1 binding polypeptide according to the first aspect $X_6X_{17}$ is VA. In some embodiments, $X_6X_{10}X_{17}$ is selected from VMA and WA. In some embodiments, $X_6X_{17}X_{20}$ is selected from VAK and VAR.

As described in detail in the experimental section to follow, the selection of PD-L1 binding polypeptide variants has led to the identification of a number of individual PD-L1 binding motif (BM) sequences. These sequences constitute individual embodiments of sequence i) according to this aspect. The sequences of individual PD-L1 binding motifs correspond to amino acid positions 8-36 in SEQ ID NO:1-4 presented in FIG. 1. Hence, in one embodiment of the PD-L1 binding polypeptide according to this aspect, corresponds to the sequence from position 8 to position 36 in a sequence selected from the group consisting of SEQ ID NO:1-4. In one embodiment, the PD-L1 binding polypeptide according to this aspect, corresponds to the sequence from position 8 to position 36 in a sequence selected from the group consisting of SEQ ID NO:1, 2 and 3; or SEQ ID NO:2, 3 and 4; or SEQ ID NO:1, 2 and 4; or SEQ ID NO:1, 3 and 4. In one particular embodiment sequence i) corresponds to the sequence from position 8 to position 36 in a sequence selected from the group consisting of SEQ ID NO:1 and 2; or SEQ ID NO:1 and 3; or SEQ ID NO:1 and 4; or SEQ ID NO:2 and 3; or SEQ ID NO:2 and 4; or SEQ ID NO:3 and 4. In one embodiment sequence i) corresponds to the sequence from position 8 to position 36 in a sequence selected from the group consisting of SEQ ID NO:1 and 4. In one embodiment, sequence i) corresponds to the sequence from position 8 to position 36 in SEQ ID NO:1, SEQ ID NO:2, SEQ ID NO:3 or SEQ ID NO:4.

In some embodiments of the present disclosure, the BM as defined above "forms part of" a three-helix bundle protein domain. This is understood to mean that the sequence of the BM is "inserted" into or "grafted" onto the sequence of the original three-helix bundle domain, such that the BM replaces a similar structural motif in the original domain. For example, without wishing to be bound by theory, the BM is thought to constitute two of the three helices of a three-helix bundle, and can therefore replace such a two-helix motif within any three-helix bundle. As the skilled person will realize, the replacement of two helices of the three-helix bundle domain by the two BM helices has to be performed so as not to affect the basic structure of the polypeptide. That is, the overall folding of the Cα backbone of the polypeptide according to this embodiment of the invention is substantially the same as that of the three-helix bundle protein domain of which it forms a part, e.g. having the same elements of secondary structure in the same order etc. Thus, a BM according to the present disclosure "forms part" of a three-helix bundle domain if the polypeptide according to this embodiment has the same fold as the original domain, implying that the basic structural properties are shared, those properties e.g. resulting in similar CD spectra. The skilled person is aware of other parameters that are relevant.

In particular embodiments, the PD-L1 binding motif (BM) thus forms part of a three-helix bundle protein domain. For example, the BM may essentially constitute two alpha helices with an interconnecting loop, within said three-helix bundle protein domain. In particular embodiments, said three-helix bundle protein domain is selected from domains of bacterial receptor proteins. Non-limiting examples of such domains are the five different three-helical domains of Protein A from *Staphylococcus aureus*, such as domain B, and derivatives thereof. In some embodiments, the three-helical bundle protein domain is a variant of protein Z, which is derived from domain B of staphylococcal Protein A (Wahlberg E et al, 2003, PNAS 100(6):3185-3190).

In some embodiments where the PD-L1 binding polypeptide as disclosed herein forms part of a three-helix bundle protein domain, the PD-L1 binding polypeptide may comprise a binding module (BMod), the amino acid sequence of which is selected from:

iii) (SEQ ID NO: 24)
K-[*BM*]-DPSQS$X_a X_b$LL$X_c$EAKKL$X_d X_e X_f$Q;

wherein

[BM] is a PD-L1 binding motif as defined herein;
$X_a$ is selected from A and S;
$X_b$ is selected from N and E;
$X_c$ is selected from A, S and C;
$X_d$ is selected from E, N and S;

$X_e$ is selected from D, E and S; and
$X_f$ is selected from A and S; and iv) an amino acid sequence which has at least 91% identity to a sequence defined in iii).

In some embodiments, said polypeptide may beneficially exhibit a high structural stability, such as resistance to chemical modifications, to changes in physical conditions and to proteolysis, during production and storage, as well as in vivo.

As discussed above, polypeptides comprising minor changes as compared to the above amino acid sequences, which do not largely affect the tertiary structure and the function of the polypeptide, are also within the scope of the present disclosure. Thus, in some embodiments, sequence iv) has at least 91%, such as at least 93%, such as at least 95%, such as at least 97% identity to a sequence defined by iii).

In one embodiment, $X_a$ in sequence iii) is A.
In one embodiment, $X_a$ in sequence iii) is S.
In one embodiment, $X_b$ in sequence iii) is N.
In one embodiment, $X_b$ in sequence iii) is E.
In one embodiment, $X_c$ in sequence iii) is A.
In one embodiment, $X_c$ in sequence iii) is S.
In one embodiment, $X_c$ in sequence iii) is C.
In one embodiment, $X_d$ in sequence iii) is E.
In one embodiment, $X_d$ in sequence iii) is N.
In one embodiment, $X_d$ in sequence iii) is S.
In one embodiment, $X_e$ in sequence iii) is D.
In one embodiment, $X_e$ in sequence iii) is E.
In one embodiment, $X_e$ in sequence iii) is S.
In one embodiment, $X_dX_e$ in sequence iii) is selected from EE, ES, SD, SE and SS.
In one embodiment, $X_dX_e$ in sequence iii) is ES.
In one embodiment, $X_dX_e$ in sequence iii) is SE.
In one embodiment, $X_dX_e$ in sequence iii) is SD.
In one embodiment, $X_f$ in sequence iii) is A.
In one embodiment, $X_f$ in sequence iii) is S.
In one embodiment, in sequence iii), $X_a$ is A; $X_b$ is N; $X_c$ is A and $X_f$ is A.
In one embodiment, in sequence iii), $X_a$ is S; $X_b$ is E; $X_c$ is A and $X_f$ is A.
In one embodiment, in sequence iii), $X_a$ is A; $X_b$ is N; $X_c$ is C and $X_f$ is A.
In one embodiment, in sequence iii), $X_a$ is S; $X_b$ is E; $X_c$ is S and $X_f$ is S.
In one embodiment, in sequence iii), $X_a$ is S; $X_b$ is E; $X_c$ is C and $X_f$ is S.
In one embodiment, in sequence iii), $X_a$ is A; $X_b$ is N; $X_c$ is A; $X_dX_e$ is ND and $X_f$ is A.
In one embodiment, in sequence iii), $X_a$ is S; $X_b$ is E; $X_c$ is A; $X_dX_e$ is ND and $X_f$ is A.
In one embodiment, in sequence iii), $X_a$ is A; $X_b$ is N; $X_c$ is C; $X_dX_e$ is ND and $X_f$ is A.
In one embodiment, in sequence iii), $X_a$ is S; $X_b$ is E; $X_c$ is S; $X_dX_e$ is ND and $X_f$ is S.
In one embodiment, in sequence iii), $X_a$ is S; $X_b$ is E; $X_c$ is C; $X_dX_e$ is ND and $X_f$ is S.
In one embodiment, in sequence iii), $X_a$ is A; $X_b$ is N; $X_c$ is A; $X_dX_e$ is SE and $X_f$ is A.
In one embodiment, in sequence iii), $X_a$ is S; $X_b$ is E; $X_c$ is A; $X_dX_e$ is SE and $X_f$ is A.
In one embodiment, in sequence iii), $X_a$ is A; $X_b$ is N; $X_c$ is C; $X_dX_e$ is SE and $X_f$ is A.
In one embodiment, in sequence iii), $X_a$ is S; $X_b$ is E; $X_c$ is S; $X_dX_e$ is SE and $X_f$ is S.
In one embodiment, in sequence iii), $X_a$ is S; $X_b$ is E; $X_c$ is C; $X_dX_e$ is SE and $X_f$ is S.
In one embodiment, in sequence iii), $X_a$ is A; X is N; $X_c$ is A; $X_dX_e$ is SD and $X_f$ is A.
In one embodiment, in sequence iii), $X_a$ is S; $X_b$ is E; $X_c$ is A; $X_dX_e$ is SD and $X_f$ is A.
In one embodiment, in sequence iii), $X_a$ is A; $X_b$ is N; $X_c$ is C; $X_dX_e$ is SD and $X_f$ is A.
In one embodiment, in sequence iii), $X_a$ is S; $X_b$ is E; $X_c$ is S; $X_dX_e$ is SD and $X_f$ is S.
In one embodiment, in sequence iii), $X_a$ is S; $X_b$ is E; $X_c$ is C; $X_dX_e$ is SD and $X_f$ is S.

In yet a further embodiment, sequence iii) corresponds to the sequence from position 7 to position 55 in a sequence selected from the group consisting of SEQ ID NO:1-4 presented in FIG. 1. Hence, in one embodiment of the PD-L1 binding polypeptide according to this aspect, corresponds to the sequence from position 7 to position 55 in a sequence selected from the group consisting of SEQ ID NO:1-4. In one embodiment, the PD-L1 binding polypeptide according to this aspect, corresponds to the sequence from position 7 to position 55 in a sequence selected from the group consisting of SEQ ID NO:1, 2 and 3; orSEQ ID NO:2, 3 and 4; or SEQ ID NO:1, 2 and 4; or SEQ ID NO:1, 3 and 4. In one embodiment sequence iii) corresponds to the sequence from position 7 to position 55 in a sequence selected from the group consisting of SEQ ID NO:1 and 2; or SEQ ID NO:1 and 3; or SEQ ID NO:1 and 4; or SEQ ID NO:2 and 3; or SEQ ID NO:2 and 4; or SEQ ID NO:3 and 4. In one particular embodiment sequence iii) corresponds to the sequence from position 7 to position 55 in a sequence selected from the group consisting of SEQ ID NO:1 and 4. In one embodiment, sequence iii) corresponds to the sequence from position 7 to position 55 in SEQ ID NO:1, SEQ ID NO:2, SEQ ID NO:3 or SEQ ID NO:4.

Also, in a further embodiment, there is provided a PD-L1 binding polypeptide, which comprises an amino acid sequence selected from:

v)                                                    (SEQ ID NO: 25)
YA-[BMod]-AP;

wherein [BMod] is a PD-L1 binding module as defined herein; and vi) an amino acid sequence which has at least 90% identity to a sequence defined in v).

Alternatively, there is provided a PD-L1 binding polypeptide, which comprises an amino acid sequence selected from:

vii)                                             (SEQ ID NO: 26)
FN-[BMod]-AP;

wherein [BMod] is a PD-L1 binding module as defined herein; and viii) an amino acid sequence which has at least 90% identity to a sequence defined in vii).

For example, in one embodiment there is provided a PD-L1 binding polypeptide selected from the group consisting of ix)                                             (SEQ ID NO: 27)
FNK-[BM]-DPSQS ANLLX$_c$ EAKKL NDAQA P;

wherein [BM] is a PD-L1 binding motif as defined above and X$_c$ is selected from A and C; and x) an amino acid sequence which has at least 90% identity to a sequence defined in ix).

In another embodiment, there is provided a PD-L1 binding polypeptide selected from the group consisting of xi)
(SEQ ID NO: 28)
FAK-[BM]-DPSQS SELLX$_c$ EAKKL SESQA P;

wherein [BM] is a PD-L1 binding motif as defined above and X$_c$ is selected from A, S and C; and xii) an amino acid sequence which has at least 90% identity to a sequence defined in xi).

In another embodiment, there is provided a PD-L1 binding polypeptide selected from the group consisting of xiii) (SEQ ID NO: 29)
FAK-[*BM*]-DPSQS SELLX$_c$ EAKKL NDSQA P;

wherein [BM] is a PD-L1 binding motif as defined above and $X_c$ is selected from A, S and C;

xiv) an amino acid sequence which has at least 90% identity to a sequence defined in xiii).

In yet another embodiment, there is provided a PD-L1 binding polypeptide selected from the group consisting of xv) (SEQ ID NO: 30)
YAK-[*BM*]-DPSQS SELLX$_c$ EAKKL NDSQA P;

wherein [BM] is a PD-L1 binding motif as defined above and $X_c$ is selected from A, S and C;

xvi) and an amino acid sequence which has at least 90% identity to a sequence defined in xv).

As discussed above, polypeptides comprising minor changes as compared to the above amino acid sequences, which do not largely affect the tertiary structure and the function of the polypeptide, also fall within the scope of the present disclosure. Thus, in some embodiments, sequence vi), viii), x), xii), xiv) or xvi) may for example be at least 90%, such as at least 92%, such as at least 94%, such as at least 96%, such as at least 98% identical to a sequence defined by v, vii), ix), xi), xiii) and xv), respectively.

In some embodiments, the PD-L1 binding motif may form part of a polypeptide comprising an amino acid sequence selected from

SEQ ID NO: 31
ADNNFNK-[*BM*]-DPSQSANLLSEAKKLNESQAPK;

SEQ ID NO: 32
ADNKFNK-[*BM*]-DPSQSANLLAEAKKLNDAQAPK;

SEQ ID NO: 33
ADNKFNK-[*BM*]-DPSVSKEILAEAKKLNDAQAPK;

SEQ ID NO: 34
ADAQQNNFNK-[*BM*]-DPSQSTNVLGEAKKLNESQAPK;

SEQ ID NO: 35
AQHDE-[*BM*]-DPSQSANVLGEAQKLNDSQAPK;

SEQ ID NO: 36
VDNKFNK-[*BM*]-DPSQSANLLAEAKKLNDAQAPK;

-continued

SEQ ID NO: 37
AEAKYAK-[*BM*]-DPSESSELLSEAKKLNKSQAPK;

SEQ ID NO: 38
VDAKYAK-[*BM*]-DPSQSSELLAEAKKLNDAQAPK;

SEQ ID NO: 39
VDAKYAK-[*BM*]-DPSQSSELLAEAKKLNDSQAPK;

SEQ ID NO: 40
AEAKYAK-[*BM*]-DPSQSSELLSEAKKLNDSQAPK;

SEQ ID NO: 41
AEAKYAK-[*BM*]-DPSQSSELLSEAKKLNDSQAP;

SEQ ID NO: 42
AEAKFAK-[*BM*]-DPSQSSELLSEAKKLNDSQAPK;

SEQ ID NO: 43
AEAKFAK-[*BM*]-DPSQSSELLSEAKKLNDSQAP;

SEQ ID NO: 44
AEAKYAK-[*BM*]-DPSQSSELLAEAKKLNDAQAPK;

SEQ ID NO: 45
AEAKYAK-[*BM*]-DPSQSSELLSEAKKLSESQAPK;

SEQ ID NO: 46
AEAKYAK-[*BM*]-DPSQSSELLSEAKKLSESQAP;

SEQ ID NO: 47
AEAKFAK-[*BM*]-DPSQSSELLSEAKKLSESQAPK;

SEQ ID NO: 48
AEAKFAK-[*BM*]-DPSQSSELLSEAKKLSESQAP;

SEQ ID NO: 49
AEAKYAK-[*BM*]-DPSQSSELLAEAKKLSEAQAPK;

SEQ ID NO: 50
AEAKYAK-[*BM*]-QPEQSSELLSEAKKLSESQAPK;

SEQ ID NO: 51
AEAKYAK-[*BM*]-DPSQSSELLSEAKKLESSQAPK;

SEQ ID NO: 52
AEAKYAK-[*BM*]-DPSQSSELLSEAKKLESSQAP;

SEQ ID NO: 53
AEAKYAK-[*BM*]-DPSQSSELLAEAKKLESAQAPK;

SEQ ID NO: 54
AEAKYAK-[*BM*]-QPEQSSELLSEAKKLESSQAPK;

SEQ ID NO: 55
AEAKYAK-[*BM*]-DPSQSSELLSEAKKLSDSQAPK;

SEQ ID NO: 56
AEAKYAK-[*BM*]-DPSQSSELLSEAKKLSDSQAP;

SEQ ID NO: 57
AEAKYAK-[*BM*]-DPSQSSELLAEAKKLSDSQAPK;

SEQ ID NO: 58
AEAKYAK-[*BM*]-DPSQSSELLAEAKKLSDAQAPK;

SEQ ID NO: 59
AEAKYAK-[*BM*]-QPEQSSELLSEAKKLSDSQAPK;

SEQ ID NO: 60
VDAKYAK-[*BM*]-DPSQSSELLSEAKKLNDSQAPK;

SEQ ID NO: 61
VDAKYAK-[*BM*]-DPSQSSELLAEAKKLNDAQAPK;

SEQ ID NO: 62
VDAKYAK-[*BM*]-DPSQSSELLSEAKKLSESQAPK;

SEQ ID NO: 63
VDAKYAK-[*BM*]-DPSQSSELLAEAKKLSEAQAPK;

-continued

```
                                SEQ ID NO: 64
VDAKYAK-[BM]-QPEQSSELLSEAKKLSESQAPK;

SEQ ID NO: 65
VDAKYAK-[BM]-DPSQSSELLSEAKKLESSQAPK;

SEQ ID NO: 66
VDAKYAK-[BM]-DPSQSSELLAEAKKLESAQAPK;

SEQ ID NO: 67
VDAKYAK-[BM]-QPEQSSELLSEAKKLESSQAPK;

SEQ ID NO: 68
VDAKYAK-[BM]-DPSQSSELLSEAKKLSDSQAPK;

SEQ ID NO: 69
VDAKYAK-[BM]-DPSQSSELLAEAKKLSDSQAPK;

SEQ ID NO: 70
VDAKYAK-[BM]-DPSQSSELLAEAKKLSDAQAPK;

SEQ ID NO: 71
VDAKYAK-[BM]-QPEQSSELLSEAKKLSDSQAPK;

SEQ ID NO: 72
VDAKYAK-[BM]-DPSQSSELLAEAKKLNKAQAPK;

SEQ ID NO: 73
AEAKYAK-[BM]-DPSQSSELLAEAKKLNKAQAPK;
and

SEQ ID NO: 74
ADAKYAK-[BM]-DPSQSSELLSEAKKLNDSQAPK;
``` wherein [BM] is a PD-L1 binding motif as defined herein.

In one embodiment, the PD-L1 binding polypeptide comprises an amino acid sequence selected from:

```
xvii)
                                SEQ ID NO: 60
VDAKYAK-[BM]-DPSQSSELLSEAKKLNDSQAPK;
``` wherein [BM] is a PD-L1 binding motif as defined herein; and xviii) an amino acid sequence which has at least 89%-identity to the sequence defined in xvii).

In one embodiment, the PD-L1 binding polypeptide comprises an amino acid sequence selected from:

```
xix)
                              (SEQ ID NO: 47)
AEAKFAK-[BM]-DPSQSSELLSEAKKLSESQAPK;
``` wherein [BM] is a PD-L1 binding motif as defined herein; and xx) an amino acid sequence which has at least 89% identity to the sequence defined in xix).

In one embodiment, the PD-L1 binding polypeptide comprises an amino acid sequence selected from:

```
xxi)
                                SEQ ID NO: 40
AEAKYAK-[BM]-DPSQSSELLSEAKKLNDSQAPK;
``` wherein [BM] is a PD-L1 binding motf as defined herein; and xxii) an amino acid sequence which has at least 89% identity to the sequence defined in xxi).

In one embodiment, the PD-L1 binding polypeptide comprises an amino acid sequence selected from:

```
xxiii)
                                SEQ ID NO: 42
AEAKFAK-[BM]-DPSQSSELLSEAKKLNDSQAPK;
``` wherein [BM] is a PD-L1 binding motif as defined herein; and xxiv) an amino acid sequence which has at least 89% identity to the sequence defined in xxiii).

Again, polypeptides comprising minor changes as compared to the above amino acid sequences, which do not largely affect the tertiary structure and the function of the polypeptide, also fall within the scope of the present disclosure. Thus, in some embodiments, sequence xviii), xx), xxii) or xxiv) may for example be at least 89%, such as at least 91%, such as at least 93%, such as at least 94%, such as at least 96%, such as at least 98% identical to a sequence defined by xvii), xix), xxi) and xxiii), respectively.

Sequence xvii) or xxi) in such a polypeptide may be selected from the group consisting of SEQ ID NO:1-5 presented in FIG. 1. In one embodiment of the PD-L1 binding polypeptide according to this aspect, sequence xvii) or xxi) corresponds to the sequence from position 1 to position 58 in a sequence selected from the group consisting of SEQ ID NO:1-5.

In one embodiment, sequence xvii) or xxi) corresponds to the sequence from position 1 to position 58 in a sequence selected from the group consisting of SEQ ID NO:1, 2, 3 and 5; or SEQ ID NO:2, 3 and 4; or SEQ ID NO:1, 2, 4 and 5; or SEQ ID NO:1, 3, 4 and 5. In one embodiment, sequence xvii) corresponds to the sequence from position 1 to position 58 in a sequence selected from the group consisting of SEQ ID NO:1, 2 and 3; or SEQ ID NO:2, 3 and 4; or SEQ ID NO:1, 2 and 4; or SEQ ID NO:1, 3 and 4.

In one embodiment sequence xvii) or xxi) corresponds to the sequence from position 1 to position 58 in a sequence selected from the group consisting of SEQ ID NO:1, 2 and 5; or SEQ ID NO:1, 3 and 5; or SEQ ID NO:1, 4 and 5; or SEQ ID NO:2 and 3; or SEQ ID NO:2 and 4; or SEQ ID NO:3 and 4.

In one embodiment sequence xvii) or xxi) corresponds to the sequence from position 1 to position 58 in a sequence selected from the group consisting of SEQ ID NO:1 and 2; or SEQ ID NO:1 and 3; or SEQ ID NO:1 and 4; or SEQ ID NO:2 and 5; or SEQ ID NO:3 and 5; or SEQ ID NO:4 and 5.

In one particular embodiment sequence xvii) or xxi) corresponds to the sequence from position 1 to position 58 in a sequence selected from the group consisting of SEQ ID NO:1, 4 and 5, such as the group consisting of SEQ ID NO:1 and 4 or the group consisting of SEQ ID NO:1 and 5. In one embodiment, sequence xvii) or xxi) corresponds to the sequence from position 1 to position 58 in SEQ ID NO:1, SEQ ID NO:2, SEQ ID NO:3, SEQ ID NO:4 or SEQ ID NO:5.

The terms "PD-L1 binding" and "binding affinity for PD-L1" as used in this specification refer to a property of a polypeptide which may be tested for example by ELISA or by the use of surface plasmon resonance (SPR) technology.

For example as described in the examples below, PD-L1 binding affinity may be tested in an experiment in which samples of the polypeptide are captured on antibody-coated ELISA plates and biotinylated PD-L1 is added followed by streptavidin-conjugated HRP. TMB substrate is added and the absorbance at 450 nm is measured using a multi-well plate reader, such as Victor[3] (Perkin Elmer). The skilled person may then interpret the results obtained by such experiments to establish at least a qualitative measure of the binding affinity of the polypeptide for PD-L1. If a quantitative measure is desired, for example to determine the EC50 value (the half maximal effective concentration) for the interaction, ELISA may also be used. The response of the polypeptide against a dilution series of biotinylated PD-L1 is measured using ELISA as described above. The skilled person may then interpret the results obtained by such experiments, and EC50 values may be calculated from the results using for example GraphPad Prism 5 and non-linear regression.

PD-L1 binding affinity may also be tested in an experiment in which PD-L1, or a fragment thereof, is immobilized on a sensor chip of a surface plasmon resonance (SPR) instrument, and the sample containing the polypeptide to be tested is passed over the chip. Alternatively, the polypeptide to be tested is immobilized on a sensor chip of the instrument, and a sample containing PD-L1, or a fragment thereof, is passed over the chip. The skilled person may then interpret the results obtained by such experiments to establish at least a qualitative measure of the binding affinity of the polypeptide for PD-L1. If a quantitative measure is desired, for example to determine a $K_D$ value for the interaction, surface plasmon resonance methods may also be used. Binding values may for example be defined in a Biacore (GE Healthcare) or ProteOn XPR 36 (Bio-Rad) instrument. PD-L1 is suitably immobilized on a sensor chip of the instrument, and samples of the polypeptide whose affinity is to be determined are prepared by serial dilution and injected in random order. $K_D$ values may then be calculated from the results using for example the 1:1 Langmuir binding model of the BIAevaluation 4.1 software, or other suitable software, provided by the instrument manufacturer.

The terms "albumin binding" and "binding affinity for albumin" as used in this disclosure refer to a property of a polypeptide which may be tested for example by the use of SPR technology in a Biacore instrument or ProteOn XPR36 instrument, in an analogous way to the example described above for PD-L1.

In one embodiment, the PD-L1 binding polypeptide is capable of binding to PD-L1 such that the $K_D$ value of the interaction with PD-L1 is at most $1 \times 10^{-6}$ M, such as at most $6 \times 10^{-7}$ M, such as at most $1 \times 10^{-7}$ M, such as at most $5 \times 10^{-8}$ M, such as at most $1 \times 10^{-8}$ M, such as at most $5 \times 10^{-8}$ M, such as at most $1 \times 10^{-9}$ M.

In one embodiment, there is provided a PD-L1 binding polypeptide according to any preceding item which is capable of binding to PD-L1 such that the EC50 value of the interaction is at most $1 \times 10^{-9}$ M, such as at most $5 \times 10^{-10}$ M, such as at most $2 \times 10^{-10}$ M.

Binding of a polypeptide as defined herein to PD-L1 may interfere either with signaling via PD-L1 in vivo or in vitro. When PD-L1 binds to PD-1, the ligand/receptor interaction dampens the T-lymphocyte response by e.g. inhibiting kinases involved in T-lymphocyte activation. Thus, blocking the binding of PD-L1 to PD-1 restores the T-lymphocyte response. Blocking activity may for example be quantified by the half maximal inhibitory concentration (IC50), which is a measure of the effectiveness of a substance in inhibiting a specific biological or biochemical function. This quantitative measure indicates how much of a particular substance is needed to inhibit a given biological process by half, and is commonly used in the art.

Thus, in one embodiment, there is provided a PD-L1 binding polypeptide as defined herein which is capable of blocking PD-L1 dependent signaling. In one embodiment, the half maximal inhibitory concentration (IC50) of the blocking is at most $1 \times 10^{-8}$ M, such as at most $7 \times 10^{-9}$ M, such as at most $5 \times 10^{-9}$ M.

In one embodiment, said PD-L1 is human PD-L1.

The skilled person will understand that various modifications and/or additions can be made to a PD-L1 binding polypeptide according to any aspect disclosed herein in order to tailor the polypeptide to a specific application without departing from the scope of the present disclosure. For example, in one embodiment, there is provided a PD-L1 binding polypeptide as described herein, which polypeptide has been extended by and/or comprises additional amino acids at the C terminus and/or N terminus. Such a polypeptide should be understood as a polypeptide having one or more additional amino acid residues at the very first and/or the very last position in the polypeptide chain. Thus, a PD-L1 binding polypeptide may comprise any suitable number of additional amino acid residues, for example at least one additional amino acid residue. Each additional amino acid residue may individually or collectively be added in order to, for example, improve and/or simplify production, purification, stabilization in vivo or in vitro, coupling or detection of the polypeptide. Such additional amino acid residues may comprise one or more amino acid residues added for the purpose of chemical coupling. One example of this is the addition of a cysteine residue. Additional amino acid residues may also provide a "tag" for purification or detection of the polypeptide, such as a His6 tag, a (HisGlu)$_3$ tag ("HEHEHE" tag) or a "myc" (c-myc) tag or a "FLAG" tag for interaction with antibodies specific to the tag or immobilized metal affinity chromatography (IMAC) in the case of a His$_6$-tag.

In one embodiment, there is provided a PD-L1 binding polypeptide as described herein which comprises additional amino acids at the C-terminal and/or N-terminal end. For example, in one embodiment of the PD-L1 binding polypeptide as disclosed herein, it consists of any one of the sequences disclosed herein, having from 0 to 15 additional C-terminal and/or N-terminal residues, such as from 0 to 7 additional C-terminal and/or N-terminal residues. In one embodiment, the PD-L1 binding polypeptide consists of any one of the sequences disclosed herein, having from 0 to 15, such as from 0 to 4, such as 3 additional C-terminal residues. In one particular embodiment, the PD-L1 binding polypeptide as described herein comprises the additional C-terminal residues VDC or VEC.

The further amino acids as discussed above may be coupled to the PD-L1 binding polypeptide by means of chemical conjugation (using known organic chemistry methods) or by any other means, such as expression of the PD-L1 binding polypeptide as a fusion protein or joined in any other fashion, either directly or via a linker, for example an amino acid linker.

A further polypeptide domain may moreover provide another PD-L1 binding moiety. Thus, in a further embodiment, there is provided a PD-L1 binding polypeptide in a multimeric form. Said multimer is understood to comprise at least two PD-L1 binding polypeptides as disclosed herein as monomer units, the amino acid sequences of which may be the same or different. Multimeric forms of the polypeptides may comprise a suitable number of domains, each having a PD-L1 binding motif, and each forming a monomer within the multimer. These domains may have the same amino acid sequence, but alternatively, they may have different amino acid sequences. In other words, the PD-L1 binding polypeptide of the invention may form homo- or heteromultimers, for example homo- or heterodimers. In one embodiment, there is provided a PD-L1 binding polypeptide, wherein said monomer units are covalently coupled together. In another embodiment, said PD-L1 binding polypeptide monomer units are expressed as a fusion protein. In one embodiment, there is provided a PD-L1 binding polypeptide in dimeric form. In one particular embodiment, said dimeric form is a homodimeric form. In another embodiment, said dimeric form is a heterodimeric form. For the sake of clarity, throughout this disclosure, the term "PD-L1 binding polypeptide" is used to encompass PD-L1 binding polypeptides in all forms, i.e. monomeric and multimeric forms.

The further amino acids as discussed above may for example comprise one or more further polypeptide domain(s). A further polypeptide domain may provide the PD-L1 binding dimer with another function, such as for example another binding function, or an enzymatic function, or a toxic function or a fluorescent signaling function, or combinations thereof.

Furthermore, it may be beneficial that the PD-L1 binding polypeptide as defined herein is part of a fusion protein or a conjugate comprising a second or further moieties. Second and further moiety/moieties of the fusion polypeptide or conjugate in such a protein may suitably have a desired biological activity.

Thus, in a second aspect of the present disclosure, there is provided a fusion protein or a conjugate, comprising a first moiety consisting of a PD-L1 binding polypeptide according to the first aspect, and a second moiety consisting of a polypeptide having a desired biological activity. In another embodiment, said fusion protein or conjugate may additionally comprise further moieties, comprising desired biological activities that can be either the same as or different from the biological activity of the second moiety.

Non-limiting examples of a desired biological activity comprise a therapeutic activity, a binding activity and an enzymatic activity. In one embodiment, the second moiety having a desired biological activity is a therapeutically active polypeptide. In one embodiment, said second moiety is an immune response modifying agent. In another embodiment, said second moiety is an anti-cancer agent.

In one embodiment of either the first or second aspect of the present disclosure, there is provided a PD-L1 binding polypeptide, fusion protein or conjugate which comprises an immune response modifying agent. Non-limiting examples of additional immune response modifying agents include immunomodulating agents or other anti-inflammatory agents.

In one embodiment of either the first or second aspect of the present disclosure, there is provided a PD-L1 binding polypeptide, fusion protein or conjugate which comprises an anti-cancer agent. Non-limiting examples of anti-cancer agents include agents selected from the group consisting of auristatin, anthracycline, calicheamycin, combretastatin, doxorubicin, duocarmycin, the CC-1065 anti-tumor-antibiotic, ecteinsascidin, geldanamycin, maytansinoid, methotrexate, mycotoxin, taxol, ricin, bouganin, gelonin, *pseudomonas* exotoxin 38 (PE38), diphtheria toxin (DT), and their analogues, and derivates thereof and combinations thereof. A skilled person would appreciate that the non-limiting examples of anti-cancer agents include all possible variants of said agents, for example the agent auristatin is intended to include for example auristatin E, auristatin F, auristatin PE, and derivatives thereof.

Non-limiting examples of therapeutically active polypeptides are biomolecules, such as molecules selected from the group consisting of human endogenous enzymes, hormones, growth factors, chemokines, cytokines and lymphokines.

Non-limiting examples of binding activities are binding activities which increase the in vivo half-life of the fusion protein or conjugate, and binding activities which act to block a biological activity. One example of such a binding activity is a binding activity, which increases the in vivo half-life of a fusion protein or conjugate. In one embodiment of said fusion protein or conjugate, the in vivo half-life of said fusion protein or conjugate is longer than the in vivo half-life of the polypeptide having the desired biological activity per se. In one embodiment, said in vivo half-life is increased at least 10 times, such as at least 25 times, such as at least 50 times, such as at least 75 times, such as at least 100 times compared the in vivo half-life of the fusion protein or conjugate per se.

The fusion protein or conjugate may comprise at least one further moiety. In one particular embodiment, said target is albumin, binding to which increases the in vivo half-life of said fusion protein or conjugate. In one embodiment, said albumin binding activity is provided by an albumin binding domain (ABD) of streptococcal protein G or a derivative thereof. Thus, said fusion protein may for example comprise a PD-L1 binding polypeptide in monomeric or multimeric form (such as a homodimeric or heterodimeric form) as defined herein and an albumin binding domain of streptococcal protein G or a derivative thereof.

In another embodiment, said there is provided a fusion protein or a conjugate wherein said second moiety having a desired binding activity is a protein based on protein Z, derived from the B domain of protein A from *Staphylococcus aureus*, which has a binding affinity for a target other than PD-L1.

For example, said fusion protein or conjugate, comprising at least one further moiety, may comprise [PD-L1 binding polypeptide]-[albumin binding moiety]-[moiety with affinity for selected target]. It is to be understood that the three moieties in this example may be arranged in any order from the N- to the C-terminal of the polypeptide.

The skilled person is aware that the construction of a fusion protein often involves the use of linkers between the functional moieties to be fused, and there are different kinds of linkers with different properties, such as flexible amino acid linkers, rigid amino acid linkers and cleavable amino acid linkers. Linkers have been used to for example increase stability or improve folding of fusion proteins, to increase expression, improve biological activity, enable targeting and alter pharmacokinetics of fusion proteins. Thus, in one embodiment, the polypeptide according to any aspect disclosed herein further comprises at least one linker, such as at least one linker selected from flexible amino acid linkers, rigid amino acid linkers and cleavable amino acid linkers. In one embodiment, said linker is arranged between said PD-L1 binding polypeptide and a further polypeptide domain, such as between a PD-L1 binding domain as disclosed herein and an antibody or antigen binding fragment thereof (as described in further detail below). Flexible linkers are often used in the art when the joined domains require a certain degree of movement or interaction, and may be particularly useful in some embodiments of the complex. Such linkers are generally composed of small, non-polar (for example G) or polar (for example S or T) amino acids. Some flexible linkers primarily consist of stretches of G and S residues, for example $(GGGGS)_p$. Adjusting the copy number "p" allows for optimization of linker in order to achieve appropriate separation between the functional moieties or to maintain necessary inter-moiety interaction. Apart from G and S linkers, other flexible linkers are known in the art, such as G and S linkers containing additional amino acid residues, such as T and A, to maintain flexibility, as well as polar amino acid residues to improve solubility. Additional non-limiting examples of linkers include GGGGSLVPRGSGGGGS, (GS)$_3$, (GS)$_4$, (GS)$_8$, GGSGGHMGSGG, GGSGGSGGSGG, GGSGG, GGSGGGGG, GGGSEGGGSEGGGSEGGG, AAGAATAA, GGGGG, GGSSG, GSGGGTGGGSG, GSGGGTGGGSG, GSGSGSGSGGSG, GSGGSGGSGGSGGS and GSGGGSGSGGSGGSG, corresponding to SEQ ID NO:6-22, respectively, and GT. The skilled person is aware of other suitable linkers.

In one embodiment, said linker is a flexible linker comprising glycine (G), serine (S) and/or threonine (T) residues. In one embodiment, said linker has a general formula selected from $(G_nS_m)_p$ and $(S_nG_m)_p$, wherein, independently, n=1-7, m=0-7, n+m≤8 and p=1-7. In one embodiment, n=1-5. In one embodiment, m=0-5. In one embodiment, p=1-5. In a more specific embodiment, n=4, m=1 and p=1-4. In one embodiment, said linker is selected from the group consisting of $S_4G$ (SEQ ID NO:75), $(S_4G)_3$ (SEQ ID NO:76) and $(S_4G)_4$ (SEQ ID NO:77). In one embodiment, said linker is selected from the group consisting of $G_4S$ (SEQ ID NO:78) and $(G_4S)_3$ (SEQ ID NO:79). In one particular embodiment, said linker is $G_4S$ (SEQ ID NO:78) and in another embodiment said linker is $(G_4S)_3$ (SEQ ID NO:79).

With regard to the description above of fusion proteins or conjugates incorporating a PD-L1 binding polypeptide according to the disclosure, it is to be noted that the designation of first, second and further moieties is made for clarity reasons to distinguish between PD-L1 binding polypeptide or polypeptides according to the invention on the one hand, and moieties exhibiting other functions on the other hand. These designations are not intended to refer to the actual order of the different domains in the polypeptide chain of the fusion protein or conjugate. Similarly, the designations first and second monomer units are made for clarity reasons to distinguish between said units. Thus, for example, said first moiety (or monomer unit) may without restriction appear at the N-terminal end, in the middle, or at the C-terminal end of the fusion protein or conjugate.

Recently, considerable progress has been made in the development of multispecific agents, such as antibodies with the ability to bind to more than one antigen, for example through engineering of the complementarity determining regions (CDRs) to address two antigens in a single antibody combining site (Bostrom et al, 2009, Science 323(5921): 1610-1614; Schaefer et al, 2011, Cancer Cell 20(4):472-486), via construction of heterodimeric antibodies using engineered Fc units (Carter, 2001, J Immunol Methods 248(1-2):7-15; Schaefer et al, 2011, Proc Natl Acad Sci USA 108(27):11187-11192) and via genetic fusion of auxiliary recognition units to N- or C-termini of light or heavy chains of full-length antibodies (Kanakaraj et al, 2012, MAbs 4(5):600-613; LaFleur et al, 2013, MAbs 5(2):208-218). Thus, it may be beneficial for a molecule incorporating an affinity for PD-L1 as disclosed herein to also exhibit affinity for another factor, such as a factor associated with cancer or an immune response associated factor.

Thus, in third aspect of the present disclosure, there is provided a complex comprising at least one PD-L1 binding polypeptide and at least one antibody or an antigen binding fragment thereof, wherein the PD-L1 binding polypeptide is as described herein.

When used herein, the term "complex" is intended to refer to two or more associated polypeptide chains, at least one having an affinity for PD-L1 and at least one being an antibody or an antigen binding fragment thereof. These polypeptide chains may each contain different protein domains, and the resulting multiprotein complex can have multiple functions. "Complex" intends to refer to two or more polypeptides as defined herein, connected by covalent bonds, for example two or more polypeptide chains connected by covalent bonds through expression thereof as a recombinant fusion protein, or associated by chemical conjugation.

As is well known, antibodies are immunoglobulin molecules capable of specific binding to a target (an antigen), such as a carbohydrate, polynucleotide, lipid, polypeptide or other, through at least one antigen recognition site located in the variable region of the immunoglobulin molecule. As used herein, the term "antibody or an antigen binding fragment thereof" encompasses not only full-length or intact polyclonal or monoclonal antibodies, but also antigen-binding fragments thereof, such as Fab, Fab', F(ab')$_2$, Fab$_3$, Fv and variants thereof, fusion proteins comprising one or more antibody portions, humanized antibodies, chimeric antibodies, minibodies, diabodies, triabodies, tetrabodies, linear antibodies, single chain antibodies, multispecific antibodies (e.g., bispecific antibodies) and any other modified configuration of the immunoglobulin molecule that comprises an antigen recognition site of the required specificity, including glycosylation variants of antibodies, amino acid sequence variants of antibodies and covalently modified antibodies. Further examples of modified antibodies and antigen binding fragments thereof include nanobodies, AlbudAbs, DARTs (dual affinity re-targeting), BiTEs (bispecific T-cell engager), TandAbs (tandem diabodies), DAFs (dual acting Fab), two-in-one antibodies, SMIPs (small modular immunopharmaceuticals), FynomAbs (fynomers fused to antibodies), DVD-Igs (dual variable domain immunoglobulin), CovX-bodies (peptide modified antibodies), duobodies and triomAbs. This listing of variants of antibodies and antigen binding fragments thereof is not to be seen as limiting, and the skilled person is aware of other suitable variants.

A full-length antibody comprises two heavy chains and two light chains. Each heavy chain contains a heavy chain variable region ($V_H$) and first, second and third constant regions ($C_H1$, $C_H2$ and $C_H3$). Each light chain contains a light chain variable region ($V_L$) and a light chain constant region ($C_L$). Depending on the amino acid sequence of the constant domain of its heavy chains, antibodies are assigned to different classes. There are six major classes of antibodies: IgA, IgD, IgE, IgG, IgM and IgY, and several of these may be further divided into subclasses (isotypes), e.g., IgG1, IgG2, IgG3, IgG4, IgA1 and IgA2. The term "full-length antibody" as used herein refers to an antibody of any class, such as IgD, IgE, IgG, IgA, IgM or IgY (or any sub-class thereof). The subunit structures and three-dimensional configurations of different classes of antibodies are well known.

An "antigen binding fragment" is a portion or region of an antibody molecule, or a derivative thereof, that retains all or a significant part of the antigen binding of the corresponding full-length antibody. An antigen binding fragment may comprise the heavy chain variable region ($V_H$), the light chain variable region ($V_L$), or both. Each of the $V_H$ and $V_L$ typically contains three complementarity determining regions CDR1, CDR2 and CDR3. The three CDRs in $V_H$ or $V_L$ are flanked by framework regions (FR1, FR2, FR3 and FR4). As briefly listed above, examples of antigen binding fragments include, but are not limited to: (1) a Fab fragment, which is a monovalent fragment having a $V_L$-$C_L$ chain and a $V_H$-$C_H1$ chain; (2) a Fab' fragment, which is a Fab fragment with the heavy chain hinge region, (3) a F(ab')$_2$ fragment, which is a dimer of Fab' fragments joined by the heavy chain hinge region, for example linked by a disulfide bridge at the hinge region; (4) an Fc fragment; (5) an Fv fragment, which is the minimum antibody fragment having the $V_L$ and $V_H$ domains of a single arm of an antibody; (6) a single chain Fv (scFv) fragment, which is a single polypeptide chain in which the $V_H$ and $V_L$ domains of an scFv are linked by a peptide linker; (7) an (scFv)$_2$, which comprises two $V_H$ domains and two $V_L$ domains, which are associated through the two $V_H$ domains via disulfide bridges and (8) domain antibodies, which can be antibody single variable domain ($V_H$ or $V_L$) polypeptides that specifically bind antigens.

Antigen binding fragments can be prepared via routine methods. For example, F(ab')$_2$ fragments can be produced by pepsin digestion of a full-length antibody molecule, and Fab fragments can be generated by reducing the disulfide bridges of F(ab')$_2$ fragments. Alternatively, fragments can be prepared via recombinant technology by expressing the heavy and light chain fragments in suitable host cells (e.g., E. coli, yeast, mammalian, plant or insect cells) and having them assembled to form the desired antigen-binding fragments either in vivo or in vitro. A single-chain antibody can be prepared via recombinant technology by linking a nucleotide sequence coding for a heavy chain variable region and a nucleotide sequence coding for a light chain variable region. For example, a flexible linker may be incorporated between the two variable regions. The skilled person is aware of methods for the preparation of both full-length antibodies and antigen binding fragments thereof.

Thus, in one embodiment, this aspect of the disclosure provides a complex as defined herein, wherein said at least one antibody or antigen binding fragment thereof is selected from the group consisting of full-length antibodies, Fab fragments, Fab' fragments, F(ab')$_2$ fragments, Fc fragments, Fv fragments, single chain Fv fragments, (scFv)$_2$ and domain antibodies. In one embodiment, said at least one antibody or antigen binding fragment thereof is selected from full-length antibodies, Fab fragments and scFv fragments. In one particular embodiment, said at least one antibody or antigen binding fragment thereof is a full-length antibody.

In one embodiment of said complex as defined herein, the antibody or antigen binding fragment thereof is selected from the group consisting of monoclonal antibodies, human antibodies, humanized antibodies, chimeric antibodies, and antigen-binding fragments thereof.

The term "monoclonal antibodies" as used herein refers to antibodies having monovalent affinity, meaning that each antibody molecule in a sample of the monoclonal antibody binds to the same epitope on the antigen, whereas the term "polyclonal antibodies" as used herein refers to a collection of antibodies that react against a specific antigen, but in which collection there may be different antibody molecules for example identifying different epitopes on the antigen. Polyclonal antibodies are typically produced by inoculation of a suitable mammal and are purified from the mammal's serum. Monoclonal antibodies are made by identical immune cells that are clones of a unique parent cell (for example a hybridoma cell line). The term "human antibody" as used herein refers to antibodies having variable and constant regions corresponding substantially to, or derived from, antibodies obtained from human subjects. The term "chimeric antibodies" as used herein, refers to recombinant or genetically engineered antibodies, such as for example mouse monoclonal antibodies, which contain polypeptides or domains from a different species, for example human, introduced to reduce the antibodies' immunogenicity. The term "humanized antibodies" refers to antibodies from non-human species whose protein sequences have been modified to increase their similarity to antibody variants produced naturally in humans, in order to reduce immunogenicity.

The complex as described herein may for example be present in the form of a fusion protein or a conjugate. Thus, said at least one PD-L1 binding polypeptide and said at least one antibody, or antigen binding fragment thereof, may be coupled by means of chemical conjugation (using known organic chemistry methods) or by any other means, such as expression of the complex as a fusion protein or joined in any other fashion, either directly or via a linker, for example an amino acid linker. The skilled person will appreciate that the above description of linker sequences in relation to fusion polypeptides is equally relevant for the complex as disclosed herein.

Thus in one embodiment, there is provided a complex as defined herein, wherein said complex is a fusion protein or a conjugate. In one embodiment, said complex is a fusion protein. In another embodiment, said complex is a conjugate. In one embodiment of said complex, said PD-L1 binding polypeptide is attached to the N-terminus or C-terminus of the heavy chain of said antibody or antigen binding fragment thereof. In another embodiment, said PD-L1 binding polypeptide is attached to the N-terminus or C-terminus of the light chain of said antibody or antigen binding fragment thereof. In one embodiment, said PD-L1 binding polypeptide is attached to the N-terminus and/or C-terminus of the light chain and heavy chain of said antibody or antigen binding fragment thereof. For example, the PD-L1 binding polypeptide may be attached to only the N-terminus of the heavy chain(s), only the N-terminus of the light chain(s), only the C-terminus of the heavy chain(s), only the C-terminus of the light chain(s), both the N-terminus and the C-terminus of the heavy chain(s), both the N-terminus and the C-terminus of the light chain(s), only the C-terminus of the light chain(s) and the N-terminus of the heavy chain(s), only the C-terminus of the heavy chain(s) and the N-terminus of the light chain(s), of said antibody or antigen binding fragment thereof.

In one embodiment there is provided a complex, wherein said PD-L1 binding polypeptide is attached either to the C-terminus or the N-terminus of the heavy chain or the light chain of said antibody or antigen binding fragment thereof.

In one particular embodiment, there is provided a complex according to any preceding item, wherein said antibody or antigen binding fragment thereof has affinity for an antigen, for example an antigen associated with an infectious disease, or an antigen associated with cancer. For example, said antigen may be PD-1 or CTLA-4.

In one embodiment there is provided a fusion protein, conjugate or complex as described herein, wherein the said second or further moiety/moieties or antibody or antigen binding fragment thereof is an inhibitor selected from the group consisting of inhibitors of PD-1, CTLA-4, T-cell immunoglobulin and mucin containing protein-3 (TIM-3), galectin-9 (GAL-9), lymphocyte activation gene-3 (LAG-3), PD-L2, B7 homolog 3 (B7-H3), B7 homolog 4 (B7-H4), V-domain Ig suppressor of T-cell activation (VISTA), carcinoembryonic antigen-related cell adhesion molecule 1 (CEACAMl), B and T lymphocyte attenuator (BTLA), colony stimulating factor 1 receptor (CSF1R), herpes virus entry mediator (HVEM), killer immunoglobulin receptor (KIR), adenosine, adenosine A2a receptor (A2aR), CD200-CD200R and T cell Ig and ITIM domain.

In one embodiment, said second moiety or antibody or antigen binding fragment thereof is an inhibitor of PD-1, such as an inhibitor selected from the group consisting of nivolumab, pidilizumab, BMS 936559, MPDL328OA (Roche) and pembrolizumab. In a specific embodiment, the inhibitor is pembrolizumab.

In one embodiment, said second moiety or antibody or antigen binding fragment thereof is an inhibitor of CTLA-4, such as an inhibitor selected from the group consisting of belatacept, abatacept, tremelimumab and ipilimumab. In a specific embodiment, the inhibitor is ipilimumab.

In one embodiment there is provide a fusion protein, conjugate or complex as described herein, wherein said second moiety or antibody or antigen binding fragment thereof is an agonist selected from the group consisting of agonists of CD134, CD40, 4-1 BB and glucocorticoid-induced TNFR-related protein (GITR).

The above aspects furthermore encompass polypeptides in which the PD-L1 binding polypeptide according to the first aspect, the PD-L1 binding polypeptide as comprised in a fusion protein or conjugate according to the second aspect or in a complex according to the third aspect, further comprises a label, such as a label selected from the group consisting of fluorescent dyes and metals, chromophoric dyes, chemiluminescent compounds, bioluminescent proteins, enzymes, radionuclides, radioactive particles and pretargeting recognition tags. Such labels may for example be used for detection of the polypeptide. For example, in some embodiments, such labeled polypeptide may for example be used for labeling or targeting tumors which have a high expression of PD-L1.

Indirect labeling of a Z variant polypeptide was recently shown using pretargeting recognition tags (Westerlund et al (2015), Bioconjugate Chem 26:1724-1736). Similarly, the disclosure provides a PD-L1 binding polypeptide as described herein labeled with a pretargeting moiety, which may then be used for indirect labeling with a moiety complementary to the pretargeting moiety. When comprising a pretargeting moiety, a PD-L1 binding agent of the present disclosure is able to associate with a complementary pretargeting moiety, and such complementary pretargeting moiety may then comprise or be attached to a suitable radionuclide. The skilled person is aware of suitable radionuclides for therapeutic, diagnostic and/or prognostic purposes. Such a radionuclide may be chelated to said complementary pretargeting moiety via a chelating environment as generally described for the PD-L1 binding agent below.

In one embodiment, the complementary pair of pretargeting moieties comprise stept(avidin)/biotin, oligonucleotide/complementary oligonucleotide such as DNA/complementary DNA, RNA/complementary RNA, phosphorothioate nucleic acid/complementary phosphorothioate nucleic acid and peptide nucleic acid (PNA)/complementary peptide nucleic acid (cPNA) and morpholinos/complementary morpholinos. In one particular embodiment, said pretargeting moiety is a PNA oligonucleotide, such as a 10-20-mer PNA sequence, such as a 15-mer PNA sequence.

In embodiments in which the polypeptide, fusion protein, conjugate or complex is labeled, directly or indirectly (e.g. via pretargeting as described above), with an imaging agent (e.g. radioactive agent), measuring the amount of labeled polypeptide present in a tumor may be done using imaging equipment, such as through acquiring radioactivity counts or images of radiation density, or derivatives thereof such as radiation concentration. Non-limiting examples of radionuclides, suitable for either direct labeling of the PD-L1 binding agent according to any aspect disclosed herein, or for indirect labeling by labeling of a complementary pretargeting moiety, include $^{68}$Ga, $^{110m}$In, $^{18}$F, $^{45}$Ti, $^{44}$Sc, $^{61}$Cu, $^{66}$Ga, $^{64}$Cu, $^{55}$Co, $^{72}$As, $^{86}$Y, $^{89}$Zr, $^{124}$I, $^{76}$Br, $^{111}$In, $^{99m}$Tc, $^{123}$I, $^{131}$I and $^{67}$Ga.

In one embodiment, the imaging equipment used in such measurements is positron emission tomography (PET) equipment, in which case the radionuclide is selected such that it is suitable for PET. The skilled person is aware of radionuclides suitable for use with PET. For example, a PET radionuclide is selected from the group consisting of $^{68}$Ga, $^{110m}$In, $^{18}$F, $^{45}$Ti, $^{44}$Sc, $^{61}$Cu, $^{66}$Ga, $^{64}$Cu, $^{55}$Co, $^{72}$As, $^{86}$Y, $^{89}$Zr, $^{124}$I and $^{76}$Br.

In another embodiment, the imaging equipment used is single-photon emission computed tomography (SPECT) equipment, in which case the radionuclide is selected such that it is suitable for SPECT. The skilled person is aware of radionuclides suitable for use with SPECT. For example, a SPECT radionuclide is selected from the group consisting of $^{111}$In, $^{99m}$Tc, $^{123}$I, $^{131}$I and $^{67}$Ga.

Thus, in one embodiment there is provided a PD-L1 binding polypeptide, fusion protein or complex as described herein, which comprises a direct or indirect radionuclide label, such as a radionuclide selected from the group consisting of $^{68}$Ga, $^{110m}$In, $^{18}$F, $^{45}$Ti, $^{44}$Sc, $^{61}$Cu, $^{66}$Ga, $^{64}$Cu, $^{55}$Co, $^{72}$As, $^{86}$Y, $^{89}$Zr, $^{124}$I, $^{76}$Br, $^{111}$In, $^{99m}$Tc, $^{123}$I, $^{131}$I and $^{67}$Ga, such as the group consisting of $^{68}$Ga, $^{110m}$In, $^{18}$F, $^{45}$Ti, $^{44}$Sc, $^{61}$Cu, $^{66}$Ga, $^{64}$Cu, $^{55}$Co, $^{72}$As, $^{86}$Y, $^{89}$Zr, $^{124}$I and $^{76}$Br, such as $^{18}$F.

In some embodiments, the labeled PD-L1 binding polypeptide is present as a moiety in a fusion protein, conjugate or complex also comprising a second moiety having a desired biological activity. The label may in some instances be coupled only to the PD-L1 binding polypeptide, and in some instances both to the PD-L1 binding polypeptide and to the second moiety of the fusion protein or conjugate and/or the antibody or antigen binding fragment thereof the complex. Furthermore, it is also possible that the label may be coupled to a second moiety, or antibody or antigen binding fragment thereof only and not to the PD-L1 binding moiety. Hence, in yet another embodiment, there is provided a PD-L1 binding polypeptide comprising a second moiety, wherein said label is coupled to the second moiety only. In another embodiment, there is provided a complex as defined herein, wherein said label is coupled to the antibody or antigen binding fragment thereof only.

When reference is made to a labeled polypeptide, this should be understood as a reference to all aspects of polypeptides as described herein, including PD-L1 binding polypeptides, fusion proteins, conjugates and complexes comprising a PD-L1 binding polypeptide. Thus, a labeled polypeptide may contain only the PD-L1 binding polypeptide and e.g. a therapeutic radionuclide, which may be chelated or covalently coupled to the PD-L1 binding polypeptide, or contain the PD-L1 binding polypeptide, a therapeutic radionuclide and a second moiety such as a small molecule having a desired biological activity, for example a therapeutic efficacy. A labeled polypeptide may contain a PD-L1 binding polypeptide in heterodimeric form and e.g. a therapeutic radionuclide, which may be chelated or covalently coupled to the PD-L1 binding polypeptide, or contain the PD-L1 binding polypeptide in heterodimeric form, a therapeutic radionuclide and a second moiety such as a small molecule having a desired biological activity, for example a therapeutic efficacy. Also envisioned is a complex which contains a PD-L1 binding polypeptide as defined herein, an antibody or antigen binding fragment thereof and a e.g. a therapeutic radionuclide, which may be chelated or covalently coupled to the PD-L1 binding polypeptide or to the antibody or antigen binding fragment thereof. The skilled person is aware of other possible variants.

In embodiments where the PD-L1 binding polypeptide, fusion protein, conjugate or complex is radiolabeled, such a radiolabeled polypeptide may comprise a radionuclide. A majority of radionuclides have a metallic nature and metals are typically incapable of forming stable covalent bonds with elements presented in proteins and peptides. For this reason, labeling of proteins and peptides with radioactive metals is performed with the use of chelators, i.e. multidentate ligands, which form non-covalent compounds, called chelates, with the metal ions. In an embodiment of the PD-L1 binding polypeptide, fusion protein, conjugate or complex, the incorporation of a radionuclide is enabled through the provision of a chelating environment, through which the radionuclide may be coordinated, chelated or complexed to the polypeptide. One example of a chelator is the polyaminopolycarboxylate type of chelator. Two classes of such polyaminopolycarboxylate chelators can be distinguished: macrocyclic and acyclic chelators.

In one embodiment, the PD-L1 binding polypeptide, fusion protein, conjugate or complex comprises a chelating environment provided by a polyaminopolycarboxylate chelator conjugated to the PD-L1 binding polypeptide via a thiol group of a cysteine residue or an epsilon amine group of a lysine residue.

The most commonly used macrocyclic chelators for radioisotopes of indium, gallium, yttrium, bismuth, radioactinides and radiolanthanides are different derivatives of DOTA (1,4,7,10-tetraazacyclododecane-1,4,7, 10-tetraacetic acid). In one embodiment, a chelating environment of the PD-L1 binding polypeptide, PD-L1 binding polypeptide in heterodimeric form, fusion protein, conjugate or complex is provided by DOTA or a derivative thereof. More specifically, in one embodiment, a chelating polypeptide encompassed by the present disclosure is obtained by reacting the DOTA derivative 1,4,7,10-tetraazacyclododecane-1, 4,7-tris-acetic acid-10-maleimidoethylacetamide (maleimidomonoamide-DOTA) with said polypeptide. In one embodiment, a chelating polypeptide encompassed by the present disclosure is obtained by reacting the DOTA derivative DOTAGA (2,2',2"-(10-(2,6-dioxotetrahydro-2H-pyran-3-yl)-1,4,7,10-tetraazacyclododecane-1,4,7-triyl)triacetic acid) with said polypeptide. Additionally, 1,4,7-triazacyclononane-1,4,7-triacetic acid (NOTA) and derivatives thereof may be used as chelators. Hence, in one embodiment, a chelating environment of the PD-L1 binding polypeptide, PD-L1 binding polypeptide in heterodimeric form, fusion protein, conjugate or complex is provided by NOTA or a derivative thereof. In one embodiment, a chelating polypeptide encompassed by the present disclosure is obtained by reacting the NOTA derivative NODAGA (2,2'-(7-(1-carboxy-4-((2,5-dioxopyrrolidin-1-yl)oxy)-4-oxobutyl)-1,4,7-triazonane-1,4-diyl)diacetic acid) with said polypeptide. The most commonly used acyclic polyaminopolycarboxylate chelators are different derivatives of DTPA (diethylenetnamine-pentaacetic acid). Hence, polypeptides having a chelating environment provided by diethylenetriaminepentaacetic acid or derivatives thereof are also encompassed by the present disclosure.

In further aspects of the present disclosure, there is provided a polynucleotide encoding a PD-L1 binding polypeptide, fusion protein or complex as described herein; an expression vector comprising said polynucleotide; and a host cell comprising said expression vector.

Also encompassed by this disclosure is a method of producing PD-L1 binding polypeptide, fusion protein or complex as described above, comprising culturing said host cell under conditions permissive of expression of said polypeptide from its expression vector, and isolating the polypeptide.

The PD-L1 binding polypeptide, fusion protein or complex of the present disclosure may alternatively be produced by non-biological peptide synthesis using amino acids and/ or amino acid derivatives having protected reactive sidechains, the non-biological peptide synthesis comprising
    step-wise coupling of the amino acids and/or the amino acid derivatives to form a polypeptide, fusion protein or complex as described herein having protected reactive side-chains,
    removal of the protecting groups from the reactive side-chains of the polypeptide fusion protein or complex, and
    folding of the polypeptide in aqueous solution.

A complex as disclosed herein may also be produced by the conjugation of at least one PD-L1 binding polypeptide or fusion protein as described herein to at least one antibody or antigen binding fragment thereof. The skilled person is aware of conjugation methods, such as conventional chemical conjugation methods, for example using charged succinimidyl esters or carbodiimides.

It should be understood that the PD-L1 binding polypeptide according to the present disclosure may be useful as a therapeutic, diagnostic and/or prognostic agent in its own right or as a means for targeting other therapeutic or diagnostic agents, with e.g. direct or indirect effects on PD-L1. A direct therapeutic effect may for example be accomplished by inhibiting PD-L1 signaling. An indirect therapeutic effect may for example be accomplished by pretargeting using PD-L1 binding polypeptides as described above.

Thus, in another aspect, there is provided a composition comprising a PD-L1 binding polypeptide, fusion protein, conjugate or complex as described herein and at least one pharmaceutically acceptable excipient or carrier. In one embodiment, said composition further comprises at least one additional active agent, such as at least two additional active agents, such as at least three additional active agents. Non-limiting examples of additional active agents that may prove useful in such combination are immune response modifying agents and anti-cancer agents as described herein.

The small size and robustness of the PD-L1 binding polypeptides of the present disclosure confer several advantages over conventional monoclonal antibody based therapies. Such advantages include advantages in formulation, modes of administration, such as alternative routes of administration, administration at higher doses than antibodies and absence of Fc-mediated side effects. The agents of the present disclosure are contemplated for oral, topical, intravenous, intraperitoneal, subcutaneous, pulmonary, transdermal, intramuscular, intranasal, buccal, sublingual or suppository administration, such as for topical administration. Also, many diseases and disorders, such as cancers and infectious disease, are associated with more than one factor. Thus, a complex as defined herein confers the advantage of targeting an additional antigen together with PD-L1.

In another aspect of the present disclosure, there is provided a PD-L1 binding polypeptide, fusion protein, conjugate, complex or composition as described herein for use as a medicament, a prognostic agent and/or a diagnostic agent. In one embodiment, there is provided a PD-L1 binding polypeptide, fusion protein, conjugate, complex or composition for use in the treatment, diagnosis or prognosis of a PD-L1 related disorder.

In one embodiment, said PD-L1 binding polypeptide, fusion protein, conjugate, complex or composition is provided for use as a medicament. In a more specific embodiment, there is provided a PD-L1 binding polypeptide, fusion protein, conjugate, complex or composition as described herein, for use as a medicament to modulate PD-L1 function in vivo. As used herein, the term "modulate" refers to changing the activity, such as rendering PD-L1 function hypomorph, partially inhibiting or fully inhibiting PD-L1 function.

In one embodiment, there is provided a PD-L1 binding polypeptide, fusion protein, conjugate, complex or composition for use in the treatment of a PD-L1 related disorder.

In one embodiment, there is provided a PD-L1 binding polypeptide, fusion protein, conjugate, complex or composition for use in the diagnosis of a PD-L1 related disorder.

In one embodiment, there is provided a PD-L1 binding polypeptide, fusion protein, conjugate, complex or composition for use in the prognosis of a PD-L1 related disorder.

As used herein, the term "PD-L1 related disorder" refers to any disorder, disease or condition in which PD-L1 signalling plays a regulatory role. Examples of such PD-L1 related disorder include infectious diseases and cancers.

It is to be understood that said PD-L1 binding polypeptide, fusion protein, conjugate, complex or composition may be used as the sole diagnostic or prognostic agent or as a companion diagnostic and/or prognostic agent.

In one embodiment, said PD-L1 related disorder is selected from the group consisting of infectious diseases and cancers. Non-limiting examples of infectious diseases include chronic viral infection, for example selected from the group consisting of human immunodeficiency virus (HIV), hepatitis B virus (HBV) and hepatitis C virus (HCV). The skilled person will appreciate that a cancer suitable for treatment, diagnosis and/or prognosis using PD-L1 binding polypeptide, fusion protein, conjugate, complex or composition may be a solid tumor cancer or a non-solid tumor cancer characterized by over-expression of PD-L1. Non-limiting examples of such cancers include skin cancer; such as melanoma and nonmelanoma skin cancer (NMSC); lung cancers such as small cell lung cancer, non-small cell lung cancer (NSCLC); head and neck cancer, renal cell carcinoma (RCC), bladder cancer, breast cancer, colorectal cancer, gastric cancer, ovarian cancer, pancreatic cancer, prostate cancer, glioma, glioblastoma, liver carcinoma, gallbladder cancer, thyroid cancer, bone cancer, cervical cancer, uterine cancer, vulval cancer, endometrial cancer, testicular cancer, kidney cancer, esophageal carcinoma, brain/CNS cancers, neuronal cancers, mesothelioma, sarcomas, small bowel adenocarcinoma and pediatric malignancies; leukaemia, acute myeloid leukaemia, acute lymphoblastic leukaemia and multiple myeloma.

In one particular embodiment, said cancer is selected from the group consisting of melanoma, NSCLC, head and neck cancer, RCC, bladder cancer, breast cancer, colorectal cancer, gastric cancer, ovarian cancer, pancreatic cancer and prostate cancer, such as a cancer selected from the group consisting of melanoma, NSCLC, head and neck cancer, RCC and bladder cancer.

In one embodiment, it may be beneficial to administer a therapeutically effective amount of a PD-L1 binding polypeptide, fusion protein, conjugate, complex or composition as described herein together with at least one second drug substance, such as an anti-cancer agent or an immune response modifying agent.

In one embodiment, there is provided a PD-L1 binding polypeptide, fusion protein, conjugate, complex or composition for use in prognosis and/or diagnosis together with at least one cell proliferation marker. Non-limiting examples of contemplated cell proliferation markers are those selected from the group consisting of Ki-67, AgNOR, choline, claspin, cyclin A, CYR61, Cdk1, histone H3, HsMCM2, IL-2, Ki-S1, Ki-S2, Ligl, MCM2, MCM6, MCM7, mitosin, p120, PCNA, PDPK, PLK, STK1, TK-1, topoisomerase II alpha and TPS.

In a related aspect, there is provided a method of treatment of a PD-L1 related disorder, comprising administering to a subject in need thereof an effective amount of a PD-L1 binding polypeptide, fusion protein, conjugate, complex or composition as described herein. In a more specific embodiment of said method, the PD-L1 binding polypeptide, fusion protein, conjugate, complex or composition as described herein modulates PD-L1 function in vivo. The skilled person will appreciate that any description in relation to the use of PD-L1 binding polypeptide, fusion protein, conjugate, complex or composition as described herein for treatment of a disease or disorder is equally relevant for the related therapeutic method. For the sake of brevity, such description will not be repeated here.

In one particular embodiment, said method of treatment, particularly relevant for the treatment of PD-L1 related cancers, comprises the steps of
  contacting the subject with a PD-L1 binding polypeptide, fusion protein, conjugate or complex comprising a pretargeting moiety as described herein, or with a composition comprising said PD-L1 binding polypeptide, fusion protein, conjugate or complex comprising a pretargeting moiety, and
  contacting the subject with a complementary pretargeting moiety comprising a radionuclide.

In another aspect of the present disclosure, there is provided a method of detecting PD-L1, comprising providing a sample suspected to contain PD-L1, contacting said sample with a PD-L1 binding polypeptide, fusion protein, conjugate, complex or composition as described herein, and detecting the binding of the PD-L1 binding polypeptide, fusion protein, conjugate, complex or composition to indicate the presence of PD-L1 in the sample.

In one embodiment, said method further comprises an intermediate washing step for removing non-bound polypeptide, fusion protein, conjugate, complex or composition, after contacting the sample.

In another embodiment, said method is a diagnostic or prognostic method for determining the presence of PD-L1 in a subject, the method comprising the steps:
a) contacting the subject, or a sample isolated from the subject, with a PD-L1 binding polypeptide, fusion protein, conjugate, complex or composition as described herein, and
b) obtaining a value corresponding to the amount of the PD-L1 binding polypeptide, fusion protein, conjugate, complex or composition that has bound in said subject or to said sample.

In one embodiment, said method further comprises an intermediate washing step for removing non-bound polypeptide, fusion protein, conjugate or composition, after contacting the subject or sample and before obtaining a value.

In one embodiment of this diagnostic or prognostic method, said PD-L1 binding polypeptide, fusion protein, conjugate or complex comprises a pretargeting moiety as described herein, and the contacting step a) of the method further comprises contacting the subject with a complementary pretargeting moiety labeled with a detectable label, such as a radionuclide label.

In one embodiment, said method further comprises a step of comparing said value to a reference. Said reference may be by a numerical value, a threshold or a visual indicator, for example based on a color reaction. The skilled person will appreciate that different ways of comparison to a reference are known in the art and may be suitable for use.

In one embodiment of such a method, said subject is a mammalian subject, such as a human subject. In one embodiment, said method is performed in vivo. In another embodiment, said method is performed in vitro.

In one embodiment, the diagnostic or prognostic method is a method for medical imaging in vivo as discussed above. Such a method comprises the systemic administration of a PD-L1 binding entity as disclosed herein (i.e. the polypeptide perse, or the fusion protein, conjugate, complex or composition containing it) to a mammalian subject. The PD-L1 binding entity is directly or indirectly labelled, with a label comprising a radionuclide suitable for medical imaging (see above for a list of contemplated radionuclides). Furthermore, the method for medical imaging comprises obtaining one or more images of at least a part of the subject's body using a medical imaging instrument, said image(s) indicating the presence of the radionuclide inside the body.

While the invention has been described with reference to various exemplary aspects and embodiments, it will be understood by those skilled in the art that various changes may be made and equivalents may be substituted for elements thereof without departing from the scope of the invention. In addition, many modifications may be made to adapt a particular situation or molecule to the teachings of the invention without departing from the essential scope thereof. Therefore, it is intended that the invention not be limited to any particular embodiment contemplated, but that the invention will include all embodiments falling within the scope of the appended claims.

BRIEF DESCRIPTION OF THE FIGURES

FIG. 1 is a listing of the amino acid sequences of examples of PD-L1 binding polypeptides of the present disclosure (SEQ ID NO:1-5). The deduced PD-L1 binding motifs (BMs) extend from residue 8 to residue 36 in each sequence. The amino acid sequences of the 49 amino acid residues long polypeptides (BMod) predicted to constitute the complete three-helix bundle within each of these Z variants extend from residue 7 to residue 55.

FIG. 6 shows PET maximum intensity projection (MIP) images of xenograft mice with LOX tumor (left) and SUDHL6 tumor (right) 30-90 min after administration of (A) [$^{18}$F]AlF-NOTA-Z15171 or (B) [$^{18}$F]FBA-Z15171.

FIG. 7 shows ex vivo biodistribution results for LOX and SUDHL6 mouse xenograft models, analyzed directly after PET data acquisition. The results are displayed in units of (A) Standard Uptake Value (SUV) and (B) tumor:blood ratio. Error bars represent standard deviation.

FIG. 8 shows the result of whole body scan of rhesus monkeys. MIPs (summed over 90-180 min; colour inverted images) of rhesus monkeys administered with (A) [$^{18}$F]AlF-NOTA-Z15171 and (B) [$^{18}$F]FBA-Z15171. (C) Average tracer uptake over ≈120-180 min in different organs displayed in the units of SUV.

EXAMPLES

Summary

Figure 2:
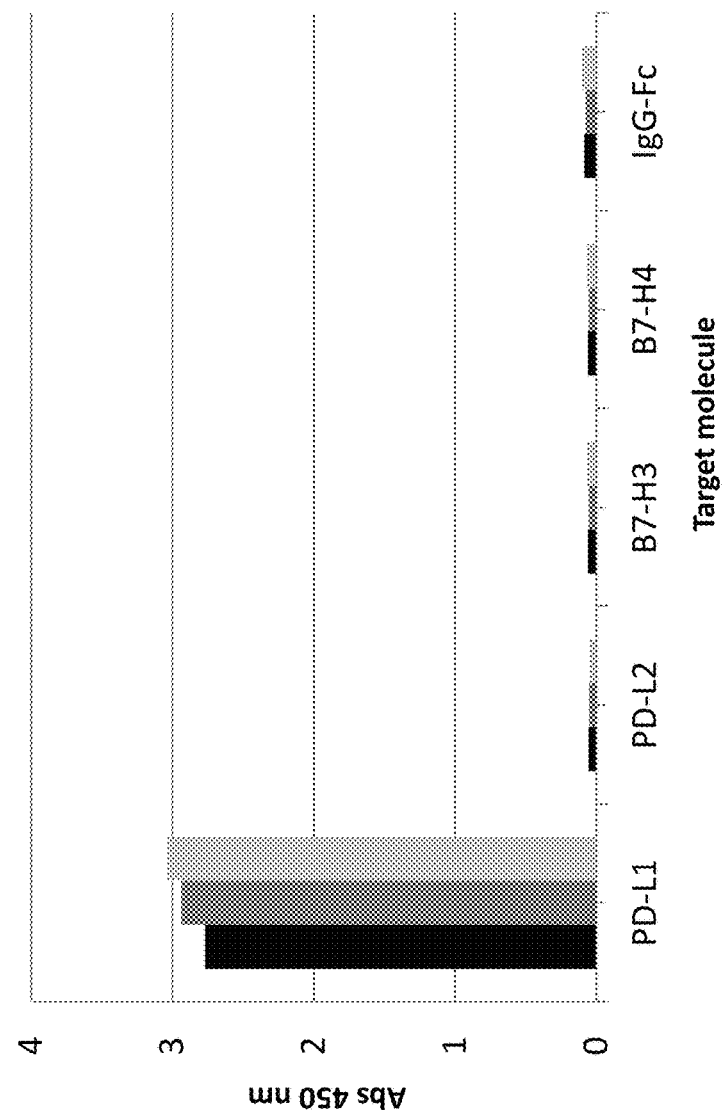
FIG. 2 shows specific binding of polypeptides to human PD-L1 analyzed by ELISA as described in Example 1. The Z variants Z13166 (SEQ ID NO:1; black bar), Z13359 (SEQ ID NO:3, dark grey bar) and Z13398 (SEQ ID NO:4; light gray bar), bind to hPD-L1, whereas no response was seen against hPD-L2, hB7-H3, hB7-H7 or IgG-Fc added at a concentration of 8 nM.

The following Examples disclose the development of novel Z variant molecules targeted to human programmed death ligand 1 (PD-L1), also known as human B7 homolog 1 (B7-H1) and cluster of differentiation 274 (CD274), based on phage display technology. The PD-L1 binding polypeptides described herein were sequenced, and their amino acid sequences are listed in FIG. 1 with the sequence identifiers SEQ ID NO:1-4. The Examples further describes the characterization of PD-L1 binding polypeptides and demonstrate in vitro functionality of said polypeptides.

Example 1

Selection and Screening of PD-L1 Binding Z Variants

In this Example, human PD-L1 (hPD-L1) was used as target in phage display selections using a phage library of Z variants. Selected clones were DNA sequenced, produced in E. coli periplasmic fractions and assayed against PD-L1 in ELISA (enzyme-linked immunosorbent assay).

Materials and Methods

Biotinylation of Target Protein:

hPD-L1 (human PD-L1 Fc Chimera, R&D Systems, cat. no. 156-B7-100) was biotinylated using No-Weigh EZ-Link Sulfo-NHS-LC-Biotin (Thermo Scentific, cat. no. 21327) at a 10× molar excess, according to the manufacturer's recommendations. The reaction was performed at room temperature (RT) for 40 min. Next buffer exchange to PBS (10 mM phosphate, 137 mM NaCl, 2.68 mM KCl, pH 7.4) was performed using a Slide-a-lyzer dialysis cassette (10000 MWCO, Thermo Scientific, cat. no. 66383) according to the manufacturer's instructions.

Phage Display Selection of PD-L1 Binding Z Variants:

A library of random variants of protein Z displayed on bacteriophage, constructed in phagemid pAY02592 essentially as described in GrOnwall et al. (2007) J Biotechnol, 128:162-183, was used to select PD-L1 binding Z variants. In this library, an albumin binding domain (ABD, GA3 of protein G from *Streptococcus* strain G148) is used as fusion partner to the Z variants. The library is denoted Zlib006Naive.II and has a size of $1.5 \times 10^{10}$ library members (Z variants). *E. coli* RRIΔM15 cells (Ruther et al., (1982) Nucleic Acids Res 10:5765-5772) from a glycerol stock containing the phagemid library Zlib006Naive.II, were inoculated in 20 l of a defined proline free medium [3 g/l $KH_2PO_4$, 2 g/l $K_2HPO_4$, 0.02 g/l uracil, 6.7 g/l YNB (Difco™ Yeast Nitrogen Base w/o amino acids, Becton Dickinson), 5.5 g/l glucose monohydrate, 0.3 g/l L-alanine, 0.24 g/l L-arginine monohydrochloride, 0.11 g/l L-asparagine monohydrate, 0.1 g/l L-cysteine, 0.3 g/l L-glutamic acid, 0.1 g/l L-glutamine, 0.2 g/l glycine, 0.05 g/l L-histidine, 0.1 g/l L-isoleucine, 0.1 g/l L-leucine, 0.25 g/l L-lysine monohydrochloride, 0.1 g/l L-methionine, 0.2 g/l L-phenylalanine, 0.3 g/l L-serine, 0.2 g/l L-threonine, 0.1 g/l L-tryptophane, 0.05 g/l L-tyrosine, 0.1 g/l L-valine], supplemented with 100 µg/ml ampicillin. The cultivations were grown at 37° C. in a fermenter (Belach Bioteknik, BR20). When the cells reached an optical density at 600 nm ($OD_{600}$) of 0.75, approximately 2.6 l of the cultivation was infected using a 10× molar excess of M13K07 helper phage (New England Biolabs, cat. no. N0315S). The cells were incubated for min, whereupon the fermenter was filled up to 20 l with cultivation medium (2.5 g/l $(NH_4)_2SO_4$; 5.0 g/l Yeast Extract (Merck 1.03753.0500); 25 g/l Peptone (Scharlau 07-119); 2 g/l $K_2HPO_4$; 3 g/l $KH_2PO_4$; 1.25 g/l $Na_3C_6H_5O_7 \cdot 2H_2O$; 0.1 ml/l Breox FMT30 antifoaming agent) supplemented with 100 µM isopropyl-β-D-1-thiogalactopyranoside (IPTG) for induction of expression and with 50 µg/ml ampicillin, 12.5 µg/ml carbenicillin, 25 µg/ml kanamycin, 35 ml/l of 1.217 M $MgSO_4$ and 10 ml of a trace element solution [129 mM $FeCl_3$; 36.7 mM $ZnSO_4$; 10.6 mM $CuSO_4$; 78.1 mM $MnSO_4$; 94.1 mM $CaCl_2$, dissolved in 1.2 M HCl]. A glucose-limited fed-batch cultivation was started where a 600 g/l glucose solution was fed to the reactor (15 g/h in the start, 40 g/h at the end of the fermentation after 17 h). pH was maitained at 7 through the automatic addition of 25% $NH_4OH$, air was supplemented (10 l/min), and the stirrer was set to keep the dissolved oxygen level above 30%. The cells in the cultivation were removed by tangential flow filtration.

The phage particles were precipitated in PEG/NaCl (polyethylene glycol/sodium chloride) from the supernatant twice, filtered and dissolved in PBS and glycerol as described in Grönwall et al., supra. Phage stocks were stored at −80° C. before use.

Selections against biotinylated hPD-L1 were performed in four cycles. In track 1 with descendants, Dynabeads® M-280 Streptavidin (SA-beads, Invitrogen, cat. no. 11206D) were used to catch the hPD-L1:Z-variant complexes. As selection proceeded, the tracks were further divided according to target concentration and number and/or time of washes. Phage stock preparation, selection procedure and amplification of phage between selection cycles were performed essentially as described for selection against another biotinylated target in WO2009/077175 with the following exception: the selection buffer consisted of PBS supplemented with 10% Fetal Bovine Serum (FBS, Gibco, cat. no. 10108-165) and 0.1% Tween20 (Acros Organics, cat. no. 233362500).

In order to reduce the amount of background binders, a pre-selection was performed in each cycle using SA-beads coated with biotinylated human IgG-Fc (Jackson ImmunoResearch Lab, cat. no. 009-060-008). Furthermore in cycle 1, track 1, the pre-selection was performed using SA-beads coated with a mix of hPD-L2 (human PD-L2 Fc Chimera; R&D Systems, cat no. 1224-PL-100), hB7-H3 (human B7-H3 Fc Chimera; R&D Systems, cat. no. 1027-B3-100), hB7-H4 (human B7-H4; R&D Systems, cat. no. 6576-B7-50), biotinylated previously as described for hPD-L1. During pre-selection the phage stock was incubated with coated beads end-over-end for 30-90 min at RT. All tubes and beads used in the pre-selections or selection were pre-blocked with PBS supplemented with 3% Bovine Serum Albumin (BSA, Sigma A3059-100G) and 0.1% Tween20. Selection was performed in solution at RT and the time for selection was approximately 120 min followed by wash with PBS+0.1% Tween20 and catch of target-phage complexes on SA-beads using 1 mg beads per 1.6 µg biotinylated hPD-L1.

For amplification of phage particles between selection cycle 1 and 2, *E. coli* strain ER2738 cells (Lucigen, Middleton, Wis., USA) were used for infection and grown in medium supplemented with 20 µg/ml tetracycline. A 5× excess of M13K07 helper phage compared to bacteria were allowed to infect log phase bacteria.

The amplification of phage particles between the selection cycles 2 and 4 was done by performing infection of bacteria in solution as follows. After infection of log phase *E. coli* ER2738 with phage particles, TSB supplemented with 2% glucose, 10 µg/ml tetracycline and 100 µg/ml ampicillin was added, followed by incubation with rotation for 30 min at 37° C. Thereafter, the bacteria were infected with M13K07 helper phage in 5× excess. The infected bacteria were pelleted by centrifugation, re-suspended in TSB-YE medium supplemented with 100 µM IPTG, 25 µg/ml kanamycin and 100 µg/ml ampicillin, and grown overnight at 30° C. The overnight cultures were centrifuged, and phage particles in the supernatant were precipitated twice with PEG/NaCl buffer. Finally, the phage particles were re-suspended in selection buffer before entering the next selection cycle. In the final selection cycle, log phase bacteria were infected with eluate and diluted before spreading onto TBAB plates (30 g/l tryptose blood agar base, Oxoid, cat. no. CMO233B) supplemented with 0.2 g/l ampicillin in order to form single colonies to be used in ELISA screening.

TABLE 2

Overview of the selection against biotinylated hPD-L1 Fc chimera using a primary library

| Cycle | Selection track | Phage stock from library or selection track | Proteins used in pre-selection | Target conc. (nM) | Number of washes | Duration of last wash (h) |
|---|---|---|---|---|---|---|
| 1 | 1 | Zlib006Naive.II | IgG-Fc, hPD-L2, hB7-H3, hB7-H4 | 100 | 2 | |
| 2 | 1-1 | 1 | IgG-Fc | 66 | 4 | |
| 3 | 1-1-1 | 1-1 | IgG-Fc | 44 | 6 | |
| 3 | 1-1-2 | 1-1 | IgG-Fc | 10 | 6 | |
| 4 | 1-1-1-2 | 1-1-1 | IgG-Fc | 10 | 31 | 1 |
| 4 | 1-1-2-1 | 1-1-2 | IgG-Fc | 10 | 31 | 15 |

An overview of the selection strategy, describing an increased stringency in subsequent cycles, using a lowered target concentration and an increased number of washes, is shown in Table 2. Washes were performed for 1 min, if nothing else is noted in Table 2, using PBST 0.1% (PBS supplemented with 0.1% Tween-20) and elution was carried out as described in WO2009/077175.

Production of Z Variants for ELISA:

The Z variants were produced by inoculating single colonies from the selections into 1 ml TSB-YE medium supplemented with 100 μg/ml ampicillin and 1 mM IPTG in deep-well plates (Nunc, cat. no. 278752). The plates were incubated with rotation for 24 h at 37° C. Cells were pelleted by centrifugation, re-suspended in 200 μl PBST 0.05% and frozen at −80° C. to release the penplasmic fraction of the cells. Frozen samples were thawed in a water bath and the freeze-thawing procedure was repeated eight times. 600 μl PBST 0.05% was added to the thawed samples and cells were pelleted by centrifugation.

The final supernatant of the periplasmic extract contained the Z variants as fusions to ABD, expressed as AQH-DEALE-[Z#####]-VDYV-[ABD]-YVPG (SEQ ID NO:80) (GrOnwall et al., supra). Z##### refers to individual, 58 amino acid residue Z variants.

ELISA Screening of Z Variants:

The binding of Z variants to hPD-L1 was analyzed in ELISA assays. Half-area 96-well ELISA plates (Costar, cat. no. 3690) were coated at 4° C. overnight with 2 μg/ml of an anti-ABD goat antibody (produced in-house) diluted in coating buffer (50 mM sodium carbonate, pH 9.6; Sigma, cat. no. C3041). The antibody solution was poured off and the wells were washed in water and blocked with 100 μl of PBSC (PBS supplemented with 0.5% casein; Sigma, cat. no. C8654) for 1 to 3 h at RT. The blocking solution was discarded and 50 μl periplasmic solutions, diluted 1:1 with PBST 0.05%, were added to the wells and incubated for 1.5 to 2.5 h at RT under slow agitation. As a blank control, PBST 0.05% was added instead of a periplasmic sample. The supematants were poured off and the wells were washed 4 times with PBST 0.05%. Then, 50 μl of biotinylated hPD-L1 at a concentration of 0.32 nM in PBSC was added to each well. The plates were incubated for 1.0 h at RT followed by washes as described above. Streptavidin conjugated HRP (Thermo Scientific, cat no. N100) diluted 1:30,000 in PBSC, was added to the wells and the plates were incubated for approximately 1 h. After washing as described above, 50 μl ImmunoPure TMB substrate (Thermo Scientific, cat. no. 34021) was added to the wells and the plates were treated according to the manufacturers recommendations. The absorbance at 450 nm was measured using a multi-well plate reader, Victor$^3$ (Perkin Elmer).

Sequencing:

In parallel with the ELISA screening, all clones were sequenced. PCR fragments were amplified from single colonies, sequenced and analyzed essentially as described in WO2009/077175

EC50 Analysis of Z Variants:

A selection of PD-L1 binding Z variants was subjected to an analysis of the response against a dilution series of biotinylated hPD-L1 following the procedure described above. The Z variants, Z13166 (SEQ ID NO:1), Z13359 (SEQ ID NO:3) and Z13398 (SEQ ID NO:4) were diluted 1:1 in PBST 0.05% and biotinylated hPD-L1 was added at a concentration of 40 nM and diluted stepwise 1:4 down to 32 μM. The Z variant Z13178 (SEQ ID NO:2) was diluted 1:8 in PBST 0.05% and biotinylated hPD-L1 was added at a concentration of 15 nM and diluted stepwise 1:3 down to 0.25 μM. As a background control, all Z variants were also assayed with no target protein added. A periplasm sample containing a Z variant confirmed to bind PD-L1 in the ELISA screen, was included on all plates as a positive control and used to normalize different plates to each other. Periplasm containing the ABD moiety only was used as a negative control. In the same assay as used for Z13166, Z13359 and Z13398, the specificity of the Z variants was tested by incubating periplasm samples with the four different biotinylated control proteins hPD-L2, hB7-H3, hB7-H4 and IgGFc, respectively, added at a concentration of 8 nM. Data were analyzed using GraphPad Prism 5 and non-linear regression and EC50 values (the half maximal effective concentration) were calculated.

Results

Phage Display Selection of PD-L1 Binding Z Variants:

Individual clones were obtained after four cycles of phage display selections against biotinylated hPD-L1.

ELISA Screening of Z Variants:

The clones obtained after four cycles of selection were produced in 96-well plates and screened for hPD-L1 binding activity in ELISA. Several unique Z variants were found to give a response of 0.3 AU or higher (corresponding to at least 3× the blank control) against hPD-L1 at a concentration of 0.32 nM. The average response of the blank controls was 0.067 AU.

Sequencing:

Sequencing was performed for clones obtained after four cycles of selection. Each variant was given a unique identification number #####, and individual variants are referred to as Z#####. The amino acid sequences of the 58 amino acid residues long Z variants are listed in FIG. 1 and in the sequence listing as SEQ ID NO: 1-4. The deduced PD-L1 binding motifs extend from residue 8 to residue 36 in each sequence. The amino acid sequences of the 49 amino acid residues long polypeptides predicted to constitute the complete three-helix bundle within each of these Z variants extend from residue 7 to residue 55.

EC50 Analysis of Z Variants:

A subset of Z variants having the highest ELISA values in the ELISA screening experiment described above was selected and subjected to a target titration in ELISA format. Periplasm samples were incubated with a serial dilution of biotinylated hPD-L1. A periplasm sample containing a Z variant confirmed to bind PD-L1 in the ELISA screen, was included on all plates as a positive control and used to normalize different plates to each other. Obtained values were analyzed and their respective EC50 values were calculated (Table 3).

No significant binding was detected to any of the included control proteins of the B7-family (hPD-L2, hB7-H3 and hB7-H4) nor to the control protein IgGFc (included here because Fc chimeric proteins were used in the selection and screening) (FIG. 2). These results indicate that the selected Z variants are specific to PD-L1.

TABLE 3

Calculated EC50 values from ELISA titration analysis.

| Designation | SEQ ID NO: | EC50 (M) |
|---|---|---|
| Z13166 | 1 | $1.9 \times 10^{-10}$ |
| Z13178 | 2 | $2.6 \times 10^{-10}$ |
| Z13359 | 3 | $3.0 \times 10^{-10}$ |
| Z13398 | 4 | $1.5 \times 10^{-10}$ |

Example 2

Subcloning and Production of PD-L1 Binding Z Variants

Materials and Methods

Subcloning of Z Variants with a His$_6$-Tag:

The DNA of four PD-L1 binding Z variants, Z13166 (SEQ ID NO:1), Z13178 (SEQ ID NO:2), Z13359 (SEQ ID NO:3) and Z13398 (SEQ ID NO:4) were amplified from the library vector pAY02592. A subcloning strategy for construction of monomeric Z variant molecules with N-terminal Hise tag was applied using standard molecular biology techniques (essentially as described in detail in WO 2009/077175 for Z variants binding another target). The Z gene fragments were subcloned into the expression vector pAY01448 resulting in the encoded sequence MGSSHHH-HHHLQ-[Z#####]-VD (SEQ ID NO:81).

Subcloning of a Z Variant with a C-Terminal Cys:

The Z variant Z13166 (SEQ ID NO:1) was mutated to start with the N-terminal amino acids AE instead of VD, resulting in Z15171 and further subcloned with a C-terminal cysteine using standard molecular biology techniques. The resulting encoding sequence was Z15171-VDC, referred to as Z15171-Cys (SEQ ID NO:5).

Cultivation:

E. coli T7E2 cells (GeneBridges) were transformed with plasmids containing the gene fragment of each respective PD-L1 binding Z variant and cultivated at 37° C. in 940 ml of TSB-YE medium supplemented with 50 µg/ml kanamycin. In order to induce protein expression, IPTG was added to a final concentration of 0.2 mM at $OD_{600}$=2 and the cultivation was incubated at 37° C. for another 5 h. The cells were harvested by centrifugation.

Purification of PD-L1 Binding Z Variants with a His$_6$-Tag:

Approximately 1-2 g of each cell pellet was resuspended in 30 ml of binding buffer (20 mM sodium phosphate, 0.5 M NaCl, 20 mM imidazole, pH 7.4) supplemented with Benzonase® (Merck, cat. no. 1.01654.0001) to a concentration of 15 U/ml. After cell disruption by sonication, cell debris was removed by centrifugation and each supernatant was applied on a 1 ml His GraviTrap IMAC column (GE Healthcare, cat. no. 11-0033-99). Contaminants were removed by washing with wash buffer (20 mM sodium phosphate, 0.5 M NaCl, 60 mM imidazole, pH 7.4) and the PD-L1 binding Z variants were subsequently eluted with elution buffer (20 mM sodium phosphate, 0.5 M NaCl, 500 mM imidazole, pH 7.4). After the IMAC purification, the protein buffer was exchanged to PBS using PD-10 columns (GE Healthcare, cat. no. 17-0851-01).

Purification of PD-L1 Binding Z Variant with a C-Terminal Cys:

The cell pellet was resuspended in 20 mM Tris-HCl, pH 8 (10 ml buffer/g cell pellet) and lysed by heat treatment in a water bath at 90° C., for 10 min, followed by cooling on ice until approximately 20° C. Benzonase® was added (1 µl/g cell pellet) and the cell lysate was incubated at RT for 30 min, before cell debris was removed by centrifugation. For reduction of disulfides, dithiothreitol (DTT; Acros organics, cat. no. 165680250) was added to a final concentration of 20 mM followed by incubation at RT for 1 h. Purification was performed by anion exchange followed by reverse phase chromatography (RPC). Buffer exchange to 20 mM HEPES, 1 mM EDTA, pH 7.2 was carried out using HiPrep 26/10 columns (GE Healthcare, cat. no. 17-5087-01). Finally, the Z variant was purified on an EndoTrap® red column (Hyglos, cat. no. 321063) to ensure low endotoxin content.

For each protein purified by any method described above, the concentration was determined by measuring the absorbance at 280 nm, using a NanoDrop® ND-1000 spectrophotometer and the extinction coefficient of the protein. The purity was analyzed by SDS-PAGE stained with Coomassie Blue and the identity of each purified Z variant was confirmed using HPLC-MS analysis (HPLC-MS 1100; Agilent Technologies).

Results

Cultivation and Purification:

The PD-L1 binding Z variants with a His$_6$-tag or a C-terminal Cys were expressed as soluble gene products in E. coli. SDS-PAGE analysis of each final protein preparation showed that these predominantly contained the PD-L1 binding Z variant. The correct identity and molecular weight of each Z variant were confirmed by HPLC-MS analysis.

Example 3

Characterization of Primary PD-L1 Binding Z Variants

In this Example, a subset of Z variants was characterized in terms of various in vitro binding properties and stability. The specificity and affinity for human PD-L1 of the Z variants were analyzed by Biacore and binding to PD-L1 expressing cells was analyzed using Fluorescence Activated Cell Sorting (FACS). Furthermore, the ability of Z variants to block the binding of PD-L1 to its receptor PD1 was investigated using AlphaLisa. The melting temperature and secondary structure was analyzed by circular dichroism (CD) spectroscopy.

Materials and Methods

Biacore Kinetic and Specificity Analysis:

Kinetic constants ($k_a$ and $k_d$) and affinities ($K_D$) for hPD-L1 were determined for the His$_6$-tagged Z variants Z13166 (SEQ ID NO:1), Z13178 (SEQ ID NO:2), Z13359 (SEQ ID NO:3) and Z13398 (SEQ ID NO:4) using a Biacore 2000 instrument (GE Healthcare). All four Z variants were also tested for binding against the sequence-related proteins hPD-L2, hB7-H3, hB7-H4. Z13166 and Z13398 were further analyzed against mPD-L1 (mouse PD-L1 Fc Chimera, R&D Systems, cat. no. 1019-B7) and Z13178 and Z13359 were analyzed against rhesus monkey PD-L1 (RhPD-L1; rhesus PD-L1/Fc Chimera, Sino Biological Inc., cat. no. 90251-C02H)

hPD-L1, hPD-L2, hB7-H3, hB7-H4, mPD-L1 and RhPD-L1 were immobilized in separate flow cells on the carboxylated dextran layer of different CM5 chip surfaces (GE Healthcare, cat. no. BR100012). The immobilization was performed using amine coupling chemistry according to the manufacturers protocol and using HBS-EP (0.01 M HEPES pH 7.4, 0.15 M NaCl, 3 mM EDTA, 0.005% v/v Surfactant P20, GE Healthcare, cat. no. BR100188) as running buffer. In a first set of experiments, in which Z13166 and Z13398 were analyzed, the ligand immobilization levels on the surfaces were 468-894 RU for hPD-L1, 482 RU for mPD-L1, 537-742 RU for hPD-L2, 383 RU for hB7-H3, and 538-659 RU for hB7-H4. One flow cell surface on each chip was activated and deactivated for use as blank during analyte injections. In the kinetic experiment, HBS-EP was used as running buffer and the flow rate was 50 µl/min. The analytes, i.e. the Z variants, were each diluted in HBS-EP buffer within a concentration range of 1000 to 0.01 nM and injected for 5 min, followed by dissociation in running buffer for 15-25 min. After dissociation, the surfaces were regenerated with one or two injections of 0.1% SDS. Kinetic constants were calculated from the sensorgrams using the Langmuir 1:1 model of BiaEvaluation software 4.1 (GE Healthcare). In a second set of experiments, in which Z13178 and Z13359 were analyzed, the ligand immobilization levels on the surfaces were 1030 RU for hPD-L1, 1060 RU for RhPD-L1, 1070 RU for hPD-L2, 1090 RU for hB7-H3, and 770 RU for hB7-H4. Analyses were performed essentially as described above for the first set of experiments, but using a flow rate of 30 µl/min and the Z variants were injected at concentrations of 5 and 50 nM over chips immobilized with hPD-L1 and RhPD-L1, and at a concentration of 500 nM over immobilized hPD-L2, hB7-H3 and hB7-H4, AlphaLISA Blocking Assay:

The potential of Z variants to inhibit binding of PD-L1 to PD-1 was analyzed by AlphaLISA and recordings in an EnSpire multiplate reader 2300 (Perkin Elmer). hPD-1 (human PD-1 Fc-chimera; R&D Systems, cat. no. 1086-PD-050) was immobilized on AlphaLISA Acceptor beads (Perkin Elmer, cat. no. 6772002) according to the manufacturers recommendations. Stepwise serial dilutions 1:3 of the His-tagged Z variants Z13166 (SEQ ID NO:1) and Z13398 (SEQ ID NO:4) to final concentrations of 250 nM to 12 µM were made in a 384 plate (Perkin Elmer, cat. no. G6005350) and incubated for 1 h with 10 nM biotinylated hPD-L1 in AlphaLISA buffer (Perkin Elmer, cat. no. AL000F). hPD-1-coated Acceptor beads were added to a final concentration of 10 µg/ml and incubated for 1 h. Finally, streptavidin coated Donor beads (Perkin Elmer, cat. no. 6772002) were added to a final concentration of 40 µg/ml and incubated for 30 min. All incubations were performed at RT in the dark. The plate was analyzed in the EnSpire instrument and the IC50 values were calculated using GraphPad Prism 5. AlphaLISA analysis of the Z variants Z13178 (SEQ ID NO:2) and Z13359 (SEQ ID NO:3) was performed essentially as described above but with the following exceptions: Exception 1: stepwise serial dilutions 1:3 of Z variants to final concentrations of 250 nM to 4 µM were made in a 384SW plate (Perkin Elmer, cat. no. 6008350) and incubated for 45 min with 8 nM biotinylated hPD-L1 (R&D Systems) in AlphaLISA buffer (Perkin Elmer, cat. no. AL000F); and Exception 2: hPD-1-coated Acceptor beads were added to a final concentration of 10 µg/ml and incubated for 50 min.

Cell Binding Analysis by FACS:

The potential of two selected Z variants, Z13166 (SEQ ID NO:1) and Z13398 (SEQ ID NO:4), to bind PD-L1 expressing cells was investigated using Fluorescence Activated Cell Sorting (FACS). THP-1 cells, cultivated in RPMI (Lonza, cat. no. BE12-702F) containing 10% FBS, were stimulated with 10 ng/ml IFNg (R&D Systems, cat. no. 285-IF-100) overnight which results in up-regulation of PD-L1. 150,000 stimulated and unstimulated cells were pipetted per well of a v-bottomed 96 well plate (Nunc, cat. no. 277143) and the cells in the plate were subsequently pelleted at 400 g for 3 min at RT. The supernatants were removed and the cells were resuspended in 100 µl PBS plus 2.5% FBS (staining buffer) containing 10 µg/ml of the different His-tagged Z variants. A mouse antiPD-L1 antibody (R&D Systems, cat. no. MAB1561) at 1 µg/ml was used as a positive control. Cells incubated with buffer alone were used as negative controls. The cells were incubated for 1 h at 8° C. in the dark, washed twice with 100 µl staining buffer and resuspended in 100 µl of staining buffer containing a goat anti-Z antibody (produced in house) at a concentration of. 5 µg/ml. Cells stained with the positive control were treated with buffer only. The cells were incubated for 1 h at 8° C. in the dark, washed twice with 100 µl staining buffer and resuspended in 100 µl of staining buffer containing an Alexa Fluor 647 chicken anti-goat IgG antibody (Life technologies, cat. no. A21469) or an Alexa Fluor 647 goat anti-mouse IgG antibody (Life technologies cat. No. A21236). The cells were once again incubated for 1 h at 8° C. in the dark, washed twice with 100 µl staining buffer and resuspended in 200 µl of staining buffer. Data from 10,000 cells were obtained using a FACS Calibur (Beckman Coulter) and the data was analyzed using Flowing software 2.5.0 (Turku University). Mean fluorescence intensity (MFI) was used as a read out of binding capacity.

Circular Dichroism (CD) Spectroscopy Analysis:

The Z variant Z15171-Cys (SEQ ID NO:5), was diluted to 0.5 mg/ml in 20 mM HEPES, 1 mM EDTA, pH 7.2. A CD spectrum at 250-195 nm was obtained at 20° C. In addition, a variable temperature measurement (VTM) was performed to determine the melting temperature (Tm). In the VTM, the absorbance was measured at 221 nm while the temperature was raised from 20 to 90° C., with a temperature slope of 5° C./min. A new CD spectrum was obtained at 20° C. after the heating procedure in order to study the refolding ability of the Z variants. The CD measurements were performed on a Jasco J-810 spectropolarimeter (Jasco Scandinavia AB) using a cell with an optical path length of 1 mm. The His-tagged Z variants Z13178 (SEQ ID NO:2) and Z13398 (SEQ ID NO:4) were analyzed by CD spectroscopy as described above, but with the exceptions that PBS was used as analysis buffer and the temperature was raised to 80° C. in the VTM.

Results

Figure 3:
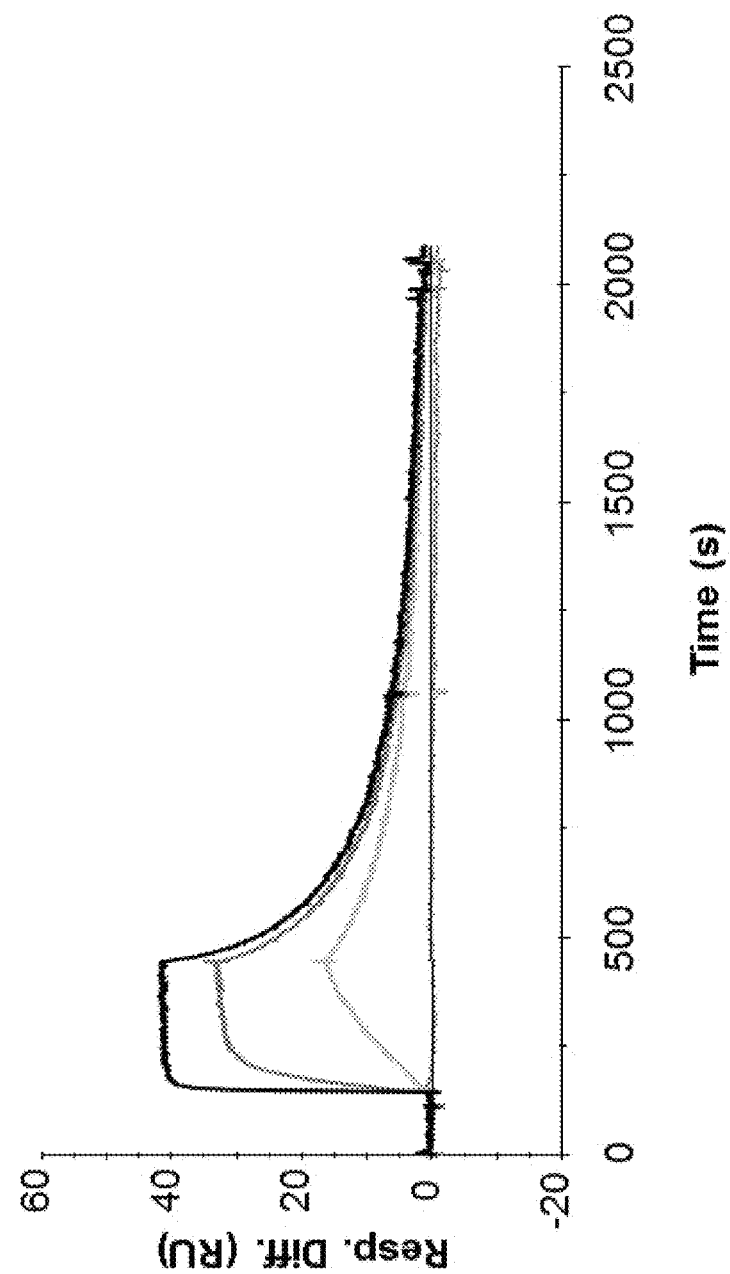
FIG. 3 shows binding of a polypeptide to human PD-L1 analyzed by Biacore as described in Example 3. The Z variant Z13166 (SEQ ID NO:1) was injected at concentrations of 50 nM (black), 5 nM (dark grey) and 0.5 nM (light grey) over a CM5 chip with immobilized hPD-L1.

Biacore Kinetic and Specificity Analysis:

The interactions of the four $His_6$-tagged PD-L1-binding Z variants Z13166 (SEQ ID NO:1), Z13178 (SEQ ID NO:2), Z13359 (SEQ ID NO:3) and Z13398 (SEQ ID NO:4) with hPD-L1 were analyzed in a Biacore instrument by injecting various concentrations of the Z variants over a surface containing immobilized hPD-L1. All tested Z variants showed binding to hPD-L1. A summary of the approximate (based on data from only two concentrations, 5 and 50 nM, of injected Z variant) kinetic parameters ($K_D$, $k_a$ and $k_d$) for binding of the Z variants to hPD-L1 obtained using a 1:1 interaction model is given in Table 4. Resulting curves, where responses from a blank surface were subtracted, are displayed in FIG. 3 for a selected Z variant, Z13166 (SEQ ID NO:1).

No binding was detected to the sequence-related proteins hPD-L2, hB7-H3 and hB7-H4 which is in line with the ELISA results presented in Example 1 and FIG. 2. Furthermore, no binding was detected to mouse PD-L1 for the two Z variants, Z13166 and Z13398, analyzed against mPD-L1. However, both Z variants, Z13178 and Z13359, analyzed for binding against Rhesus monkey PD-L1 showed binding to RhPD-L1 and the approximate (based on data from only one concentration, 5 nM, of injected Z variant) kinetic parameters are presented in Table 5.

TABLE 4

Approximate kinetic parameters for binding of Z variants to hPD-L1.

| Designation | SEQ ID NO: | $k_a$ (1/Ms) | $k_d$ (1/s) | $K_D$ (M) |
|---|---|---|---|---|
| Z13166 | 1 | $7.4 \times 10^6$ | $2.6 \times 10^{-3}$ | $4.0 \times 10^{-10}$ |
| Z13178 | 2 | $1.9 \times 10^1$ | $1.0 \times 10^{-5}$ | $5.4 \times 10^{-7}$ |
| Z13359 | 3 | $1.9 \times 10^6$ | $2.8 \times 10^{-2}$ | $1.5 \times 10^{-8}$ |
| Z13398 | 4 | $5.1 \times 10^6$ | $3.7 \times 10^{-3}$ | $7.3 \times 10^{-10}$ |

TABLE 5

Approximate kinetic parameters for binding of Z variants to RhPD-L1.

| Designation | SEQ ID NO: | $k_a$ (1/Ms) | $k_d$ (1/s) | $K_D$ (M) |
|---|---|---|---|---|
| Z13178 | 2 | $1.1 \times 10^5$ | $2.5 \times 10^{-3}$ | $2.2 \times 10^{-8}$ |
| Z13359 | 3 | $4.9 \times 10^5$ | $9.7 \times 10^{-3}$ | $2.0 \times 10^{-8}$ |

AlphaLISA Blocking Assay:

The ability of the $His_6$-tagged Z variants to inhibit hPD-L1 binding to hPD-1 was tested in an AlphaLISA blocking assay. Serial dilutions of the Z variants were incubated with biotinylated hPD-L1 and the blocking ability of each respective variant was measured after addition of hPD-1 coated Acceptor beads and subsequently streptavidin coated Donor beads. Inhibition could be measured as a decrease in AlphaLISA counts for positive Z variants. The calculated IC50 values for the four variants that were all shown to block PD-L1 binding to PD-1 in this assay are shown in Table 6.

TABLE 6

IC50 values for Z variants inhibiting binding of PD-L1 to PD-1

| Designation | SEQ ID NO: | IC50 (M) |
|---|---|---|
| Z13166 | 1 | $6.2 \times 10^{-9}$ |
| Z13178 | 2 | $\sim 1 \times 10^{-8}$ |
| Z13359 | 3 | $1.8 \times 10^{-9}$ |
| Z13398 | 4 | $4.9 \times 10^{-9}$ |

Figure 4:
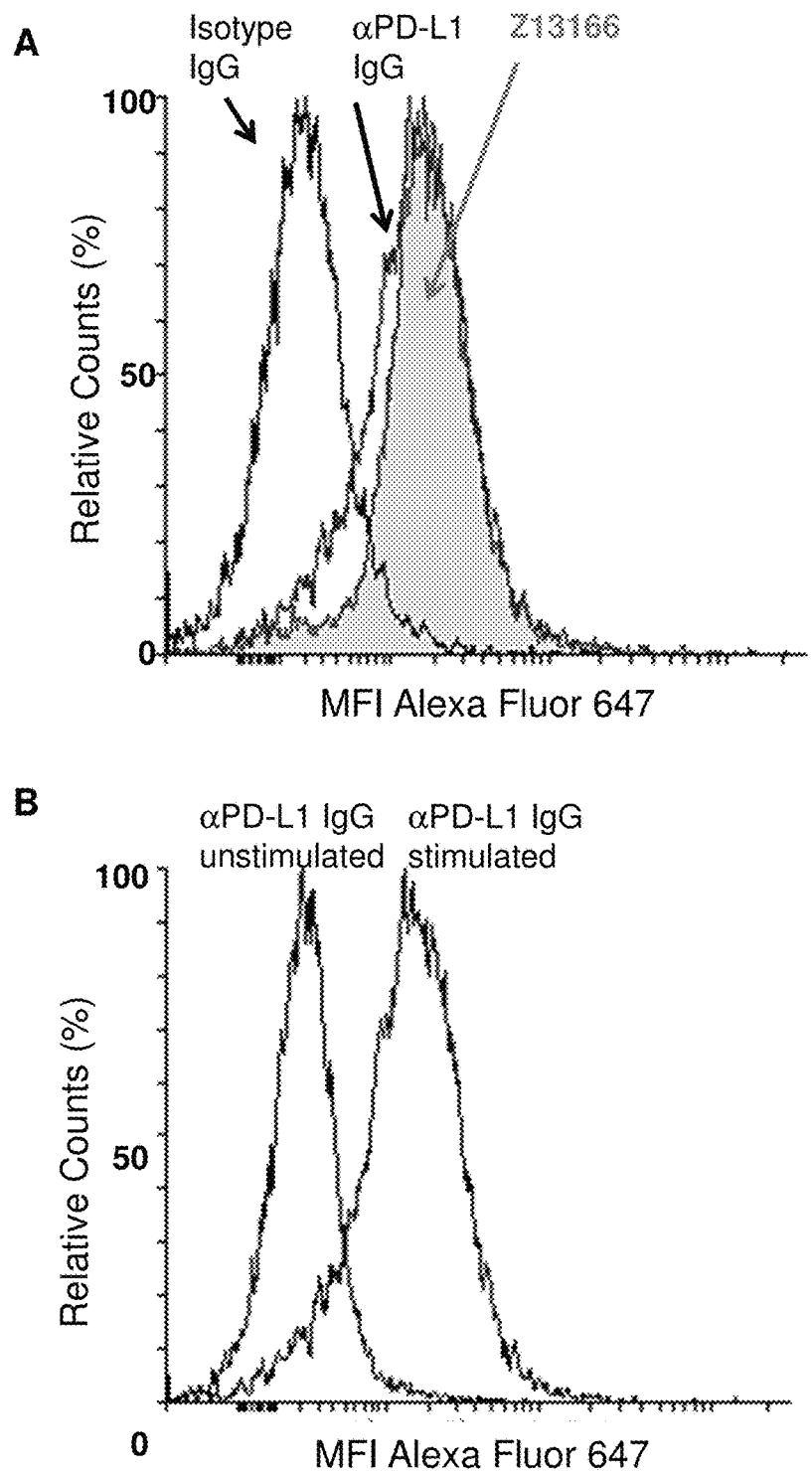
FIG. 4 shows histograms of Z13166 (SEQ ID NO:1) binding to PD-L1 expressing THP-1 cells analyzed by FACS as described in Example 3. In (A) THP-1 cells were stimulated with 10 ng/ml IFNγ overnight and stained with 10 μg/ml of Z13166 (filled gray histogram). Staining with an anti PD-L1 specific antibody or a mouse IgG isotype control is shown for comparison. In (B) stimulated and unstimulated THP-1 cells were stained with 1 μg/ml of a PD-L1 specific antibody.

Cell Binding Analysis by FACS:

This experiment confirmed binding of the PD-L1 specific Z variants to PD-L1 expressing cells. THP-1 cells stimulated with IFNγ overnight, which increases the PD-L1 expression, were stained with 10 μg/ml of each of the His-tagged Z variants Z13166 and Z13398. The analyses were performed at two different occasions and the MFI values normalized against a positive control Z variant included in both experiments are presented in Table 7 and the histogram for Z13166 is shown in FIG. 4.

TABLE 7

Normalized MFI for binding of Z variants to PD-L1 expressing THP-1 cells

| Designation | SEQ ID NO: | MFI (normalized) |
|---|---|---|
| Z13166 | 1 | 0.76 |
| Z13398 | 4 | 0.94 |
| anti-PD-L1 antibody | — | 0.40 |

Figure 5:
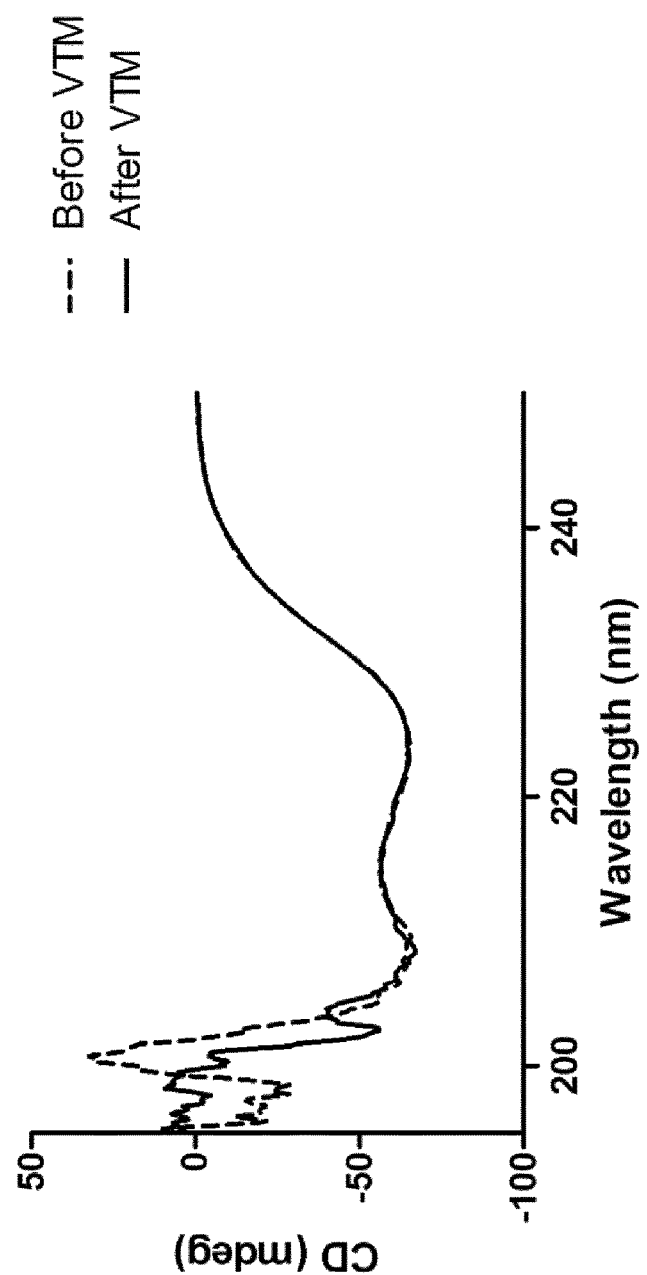
FIG. 5 shows circular dichroism (CD) spectra of the PD-L1 binding Z variant Z15171-Cys (SEQ ID NO:5). The CD spectra at wavelengths ranging from 250 to 195 nm collected at 20° C. before (broken line) and after (solid line) the variable temperature measurement (VTM) are shown.

CD Analysis:

The CD spectra determined for three PD-L1 binding Z variants showed that all variants had an α-helical structure at 20° C. as judged from the typical minima at 208 and 222 nm. Reversible folding was seen for all Z variants when overlaying spectra measured before and after heating to 90° C., exemplified in FIG. 5 showing Z15171-Cys. The noisy signal observed in the far UV region is expected to result from buffer effects (HEPES, which was used as analysis buffer, absorbs strongly at 200 nM and below). The melting temperatures (Tm) are summarized in Table 8.

TABLE 8

Melting temperatures (Tm)

| Designation | SEQ ID NO: | Tm (° C.) |
|---|---|---|
| Z13178 | 2 | 52 |
| Z13398 | 4 | 53 |
| Z15171-Cys | 5 | 51 |

Example 4

Conjugation and Radiolabeling of PD-L1 Binding Z Variant

Materials and Methods

NOTA Conjugation and [$^{18}$F]AlF-Labeling:

To 5 mg of Z variant in [20 mM HEPES, 1 mM EDTA, pH 7.2] was added three molar equivalents of tris(2-carboxyethyl)phosphine (TCEP) in 0.5 ml of degassed 0.2 M ammonium acetate buffer (pH 7.0). The reaction was kept at RT for 60 min before being transferred to an Ultracel 3K Centrifugal Filter and centrifuged at 4000 rpm for 90 min. The flow-through was discarded and an additional 1 ml of 0.2 M ammonium acetate buffer added, and the process repeated. The reduced Z variant was then transferred to a second reaction vessel in 2 ml of oxygen free 0.2 M ammonium acetate buffer (pH 7.0). 4 mg of NOTA-maleimide (Macrocyclics) in 0.5 ml of 0.2 M ammonium acetate buffer (pH 7.0) was then added, and the reaction vessel purged with argon before heated to 40° C. for 3 h, at which point the reaction mixture was transferred to an Ultracel 3K Centrifugal Filter and centrifuged for 90 min at 4000 rpm. The flow-through was discarded and 2 ml milliQ water added. Centrifugation was performed for an additional 90 min and the flow-through discarded. Purified NOTA-conjugated Z variant was collected in 1 ml milliQ water, lyophilized and stored at −70° C. prior to use. Purity of the final product was determined by LC/MS.

A cartridge containing [$^{18}$F]-fluoride was first washed with 1.5 ml of ultrapure water, then [$^{18}$F]-fluoride was eluted with 1.0 ml of 0.4 M KHCO$_3$. 100 µl of the eluted [$^8$F]-fluoride solution was added to a stem vial charged with 10 µl acetic acid, 50 µl AlCl$_3$ (2 mM in 0.1 M NaOAc buffer, pH 4) and 125 µl 0.1 M NaOAc pH 4. The solution was incubated for 2 min at RT before 1 mg of NOTA-conjugated Z variant in 400 µl of a 1:1 solution of acetrontrile and 0.1 M NaOAc pH 4 was added, then heated to 100° C. for 15 min. After heating was complete, the sample was transferred to a vial containing 0.7 ml of 0.1% formic acid, mixed and purified by HPLC [Waters Xselect CSH C18 column (250× 10 mm, 130 µm)] using a gradient of 10-30% MeCN over 15 min at a flow rate of 5 ml/min, the balance being 0.1% formic acid. The peak corresponding to [$^{18}$F]AlF-NOTA-Z##### was collected, the MeCN was removed in vacuo, and transferred to a sterile vial using physiologic saline as a rinse to give [$^{18}$F]AlF-NOTA-Z#####. Specific activity and radiochemical purity was determined using a Waters Acquity LC/MS system (Milford, Mass., USA) and a β-RAM Model 4 Radio-HPLC detector (IN/US Systems, Brandon, Fla., USA).

Aminooxy conjunction and [$^1$F]-fluorobenzaldehyde ([$^{18}$F]FBA) labeling:

Using the same procedure as described for the NOTA conjugated analogue, the maleimide (E)-ethyl N-2-((2-(2,5-dioxo-2,5-dihydro-1H-pyrrol-1-yl)ethyl)amino)-2-oxoethoxyacetimidate was conjugated to Z15171-Cys followed by TFA deprotection to generate aminooxy-conjugated Z15171-Cys. Purified aminooxy-conjugated Z variant was collected in 1 ml of milliQ water, lyophilized and stored at −70° C. prior to use. Purity of the final product was determined by LC/MS.

[$^{18}$F]FBA was prepared as previously described (Namavari et al, 2008, Mol. Imaging and Biol., 10:177-181). After the reaction was complete, [$^{18}$F]FBA was purified via HPLC [Waters Xselect CSH C18 column (250×10 mm, 130 µm)] using a gradient of 30-50% MeCN over 15 min at a flow rate of 5 ml/min, the balance being 0.1% formic acid. The peak corresponding to [$^{18}$F]FBA was collected, diluted with the addition of 10 ml milliQ water and loaded onto a 6 ml Strata X polymeric C18 SPE Cartridge (Phenomenex, Torrance, Calif. USA) and washed with an additional 10 ml milliQ water. [$^{18}$F]FBA was then eluted into a 10 ml sterile vial with 2 ml of methanol.

500 µl of the methanol solution of [$^{18}$F]FBA was added to 100 µl (≈10 mg/ml) of aminooxy-conjugated Z15171-Cys (SEQ ID NO:5), and heated at 60° C. for 10 min. After heating was complete, the sample was transferred to a vial containing 0.7 ml of 0.1% formic acid, mixed and purified by HPLC [Waters Xselect CSH C18 column (250×10 mm, 130 µm)] using a gradient of 10-30% MeCN over 15 min at a flow rate of 5 ml/min, the balance being 0.1% formic acid. The peak corresponding to [$^{18}$F]FBA-aminooxy-conjugated Z15171-Cys was collected, the MeCN was removed in vacuo, and transferred to a sterile vial using physiologic saline as a rinse to give [$^{18}$F]FBA-aminooxy-conjugated Z15171-Cys. Specific activity and radiochemical purity was determined using a Waters Acquity LC/MS system (Milford, Mass., USA) and a β-RAM Model 4 Radio-HPLC detector (IN/US Systems, Brandon, Fla., USA).

Results

NOTA Conjugation and [$^{18}$F]AlF-Labeling:

The PD-L1 binding Z variant Z15171-Cys (SEQ ID NO:5) was site-specifically conjugated with NOTA at its unique C-terminal cysteine residue. Subsequent radiolabeling with [$^{18}$F]AlF resulted in a radiochemical purity of 97-100% and a specific activity of 14.6±6.5 GBq/mmol at the end of synthesis.

Aminooxy Conjunction and [$^{18}$F]-Fluorobenzaldehvde ([$^{18}$F]FBA) Labeling:

Z15171-Cys was site-specifically aminooxy-conjugated at its unique C-terminal cysteine residue and subsequently radiolabeled with [$^{18}$F]FBA. The radiochemical purity of [$^{18}$F]FBA-Z15171 was determined to 100% by LC/MS and the specific activity was 16.5 GBq/pmol at the end of synthesis.

Example 5

In vivo imaging and biodistribution in tumor bearing mice
Materials and Methods
Animal Models:

Female SCID Beige mice (6-8 week old, Charles River Laboratories) were housed in a temperature and humidity controlled room and kept on a regular diet. LOXIMVI (human melanoma cell line; PD-L1 positive) or SUDHL-6 (PD-L1 negative) cells were cultured in complete growth medium containing RPMI 1640 medium with 10% fetal bovine serum at 37° C. with 5% CO$_2$. The growth media was changed 2 or 3 times per week and the cells were subcultured at a ratio of 1:10 when needed. Tumors were implanted at the right shoulder by subcutaneous injection of 1×10$^6$ LOXIMVI cells in 100 µl PBS or 10×10$^8$ SUDHL-6 cells in 100 µl PBS+Growth Factor Reduced Matrigel (1:1). The mice were used for micro-PET and ex vivo studies about 5-7 days and 3 weeks after the injection of LOXIMVI and SUDHL-6 cells, respectively, when tumors reached a mass of 100-400 mg.

PET Data Acquisition:

Mice were anesthetized with isoflurane (4-5% induction, 1-3% maintenance), prepared with tail vein catheters, and placed in a dedicated small animal PET scanner (microPET Focus220, Siemens Preclinical Solutions). A 20 min transmission scan with $^{57}$Co was obtained to correct for photon attenuation and scatter. Then, 0.4-0.7 MBq of [$^{18}$F]AlF-NOTA-Z15171 or 0.03-0.3 MBq of [$^{18}$F]FBA-Z15171 was administered via the tail vein catheters and PET data were collected for 90 min.

Ex Vivo Biodistribution Measurements:

Immediately following PET acquisition, mice were euthanized. Tumor, heart, lung, spleen, liver, kidneys, blood, plasma and muscle were collected and measured using a gamma counter (PerkinElmer). For each mouse, biodistribution measurements were converted into units of Standard Uptake Value (SUV). Regions of Interest (ROI) were drawn on all tumors that could be identified in PET images, and time activity curves (TACs) were calculated.

Results

Representative PET images following injection of [$^{18}$F] AlF-NOTA-Z15171 and [$^{18}$F]FBA-Z15171, respectively, are shown in FIG. 6A-B. PD-L1 positive LOX tumors could be clearly seen in these images, while PD-L1 negative SUDHL6 tumors were not visible. The kidney uptake for [$^{18}$F]FBA-Z15171 (SUV=3.1±0.7 for LOX xenograft mice) was lower than for [$^{18}$F]AlF-NOTA-Z15171 (SUV=57±10 for LOX xenograft mice). The kidney tracer retention of the latter is likely due to tubular reuptake of proteins, where the [$^{18}$F]AlF label is trapped after cleavage of the Z variants. On the contrary, the liver uptake was higher for [$^{18}$F]FBA-Z15171 than for [$^{18}$F]AlF-NOTA-Z15171.

Ex vivo biodistribution measurements at 90 min after injection were in agreement with PET images (FIG. 7A). The LOX tumor uptake of [$^{18}$F]AlF-NOTA-Z15171 and [$^{18}$F]FBA-Z15171 was approximately the same, but the tumor:blood ratio was higher for [$^{18}$F]AlF-NOTA-Z15171 (FIG. 7B), indicating a slower clearance of [$^{18}$F]FBA-Z15171. To summarize, the results show that Z variant ligand was effective in targeting PD-L1 positive tumors in vivo, exhibiting specific binding and a rapid clearance.

Example 6

In Vivo Imaging in Rhesus Monkey

Materials and Methods

Fasted rhesus monkeys were sedated with Ketamine (10 mg/kg, intramuscular). An intravenous catheter was inserted into the right and left saphenous veins and the animals were maintained on propofol anesthesia (5 mg/kg for induction and 0.45 mg/kg/min throughout the scanning procedure). Following the initial induction with propofol, the animal was intubated and maintained on a ventilated oxygen/air gas mixture at approximately 10 cm$^3$/kg/breath, and 23 respirations per minute. Animals were instrumented with a temperature probe, a pulse oximeter and an end tidal $CO_2$ monitor. Body temperature was maintained using K-module heating pads. General fluid therapy was maintained with Lactated Ringer's solution (10 ml/kg/h i.v.) throughout the scanning procedure. 167-199 MBq of [$^{18}$F]AlF-NOTA-Z15171 and 42-106 MBq of [$^{18}$F]FBA-Z15171, respectively, were administered as a 2 min infusion. Whole body dynamic scan was initiated at the start of the tracer injection and aquired for 180 min using a Siemens Biograph 64 TPTV PET/CT scanner. Whole body reconstruction was performed using the PET/CT scanner vendor supplied software. PET image analysis was performed using customized Matlab based software.

Results

Representative maximum intensity projection images of rhesus monkeys administered with [$^{18}$F]AlF-NOTA-Z15171 and [$^{18}$F]FBA-Z15171, respectively, are shown in FIG. 8A-B and graphs of the average tracer uptake ($\approx$120-180 min) are shown in FIG. 8C. As in mice, the kidney uptake of [$^{18}$F]FBA-Z15171 (SUV$\approx$30±4) was lower than for [$^{18}$F] AlF-NOTA-Z15171 (SUV$\approx$114±9) whereas [$^{18}$F]FBA-Z15171 showed a higher liver uptake. Lymph node and spleen targeting was observed for both tracers, which is consistent with PD-L1 expression.

Itemized List of Embodiments

1. PD-L1 binding polypeptide, comprising a PD-L1 binding motif BM, which motif consists of an amino acid sequence selected from:

i)
(SEQ ID NO: 23)
ERTX$_4$AX$_6$WEIX$_{10}$X$_{11}$LPNLX$_{16}$X$_{17}$X$_{18}$QX$_{20}$GAFIX$_{25}$X$_{26}$LHD wherein, independently from each other,
$X_4$ is selected from I, M, V and W;
$X_6$ is selected from T and V;
$X_{10}$ is selected from M and V;
$X_{11}$ is selected from D and Q;
$X_{16}$ is selected from N and T;
$X_{17}$ is selected from A and S;
$X_{18}$ is selected from G, R and W;
$X_{20}$ is selected from K and R;
$X_{25}$ is selected from D, N and W; and
$X_{26}$ is selected from K and S;
and ii) an amino acid sequence which has at least 89% identity to the sequence defined in i).

2. PD-L1 binding polypeptide according to item 1, wherein in sequence i)
$X_4$ is selected from I, M, V and W;
$X_6$ is selected from T and V;
$X_{10}$ is selected from M and V;
$X_{11}$ is selected from D and Q;
$X_{16}$ is T;
$X_{17}$ is selected from A and S;
$X_{18}$ is selected from G, R and W;
$X_{20}$ is selected from K and R;
$X_{25}$ is selected from D, N and W; and
$X_{26}$ is K.

3. PD-L1 binding polypeptide according to any one of item 1-2, wherein sequence i) fulfills at least three of the six conditions I-VI:
I. $X_6$ is V;
II. $X_{16}$ is T;
III. $X_{17}$ is A;
IV. $X_{18}$ is W;
V. $X_{25}$ is N; and
VI. $X_{26}$ is K.

4. PD-L1 binding polypeptide according to item 3, wherein sequence i) fulfills at least four of the six conditions I-VI.

5. PD-L1 binding polypeptide according to item 4, wherein sequence i) fulfills at least five of the six conditions I-VI.

6. PD-L1 binding polypeptide according to item 5, wherein sequence i) fulfills all of the six conditions I-VI.

7. PD-L1 binding polypeptide according to any one of items 1-6, wherein $X_6X_{17}$ is VA.

8. PD-L1 binding polypeptide according to any one of items 1-6, wherein $X_6X_{10}X_{17}$ is selected from VMA and WA.

9. PD-L1 binding polypeptide according to any one of items 1-6, wherein $X_6X_{17}X_{20}$ is selected from VAK and VAR.

10. PD-L1 binding polypeptide according to any preceding item, wherein sequence i) corresponds to the sequence from position 8 to position 36 in a sequence selected from the group consisting of SEQ ID NO:1-4.

11. PD-L1 binding polypeptide according to item 10, wherein sequence i) corresponds to the sequence from position 8 to position 36 in a sequence selected from the group consisting of SEQ ID NO:1 and 4.

12. PD-L1 binding polypeptide according to item 10 or 11, wherein sequence i) corresponds to the sequence from position 8 to position 36 in SEQ ID NO: 1.

13. PD-L1 binding polypeptide according to item 10, wherein sequence i) corresponds to the sequence from position 8 to position 36 in SEQ ID NO:2.

14. PD-L1 binding polypeptide according to item 10, wherein sequence i) corresponds to the sequence from position 8 to position 36 in SEQ ID NO:3.
15. PD-L1 binding polypeptide according to item 10 or 11, wherein sequence i) corresponds to the sequence from position 8 to position 36 in SEQ ID NO:4.
16. PD-L1 binding polypeptide according to any preceding item, wherein said PD-L1 binding motif forms part of a three-helix bundle protein domain.
17. PD-L1 binding polypeptide according to item 16, wherein said PD-L1 binding motif essentially forms part of two helices with an interconnecting loop, within said three-helix bundle protein domain.
18. PD-L1 binding polypeptide according to item 17, wherein said three-helix bundle protein domain is selected from bacterial receptor domains.
19. PD-L1 binding polypeptide according to item 18, wherein said three-helix bundle protein domain is selected from domains of protein A from *Staphylococcus aureus* or derivatives thereof.
20. PD-L1 binding polypeptide according to any preceding item, which comprises a binding module BMod, the amino acid sequence of which is selected from:

iii)
(SEQ ID NO: 24)
K-[BM]DPSQSX$_a$X$_b$LLX$_c$EAKKLX$_d$X$_e$X$_f$Q;

wherein
[BM] is a PD-L1 binding motif as defined in any one of items 1-15;
X$_a$ is selected from A and S;
X$_b$ is selected from N and E;
X$_c$ is selected from A, S and C;
X$_d$ is selected from E, N and S;
X$_e$ is selected from D, E and S; and
X$_f$ is selected from A and S; and
iv) an amino acid sequence which has at least 91% identity to a sequence defined by iii).
21. PD-L1 binding polypeptide according to any preceding item, wherein sequence iii) corresponds to the sequence from position 7 to position 55 in a sequence selected from the group consisting of SEQ ID NO:1-4.
22. PD-L1 binding polypeptide according to item 21 wherein sequence iii) corresponds to the sequence from position 7 to position 55 in a sequence selected from the group consisting of SEQ ID NO:1 and 4.
23. PD-L1 binding polypeptide according to item 21 or 22, wherein sequence iii) corresponds to the sequence from position 7 to position 55 in SEQ ID NO:1.
24. PD-L1 binding polypeptide according to item 21, wherein sequence iii) corresponds to the sequence from position 7 to position 55 in SEQ ID NO:2.
25. PD-L1 binding polypeptide according to item 21, wherein sequence iii) corresponds to the sequence from position 7 to position 55 in SEQ ID NO:3.
26. PD-L1 binding polypeptide according to item 21 or 22, wherein sequence iii) corresponds to the sequence from position 7 to position 55 in SEQ ID NO:4.
27. PD-L1 binding polypeptide according to any preceding item, which comprises an amino acid sequence selected from:

v)
(SEQ ID NO: 25)
YA-[BMod]-AP;

wherein [BMod] is a PD-L1 binding module as defined in any one of items 20-26; and
vi) an amino acid sequence which has at least 90% identity to a sequence defined by v).
28. PD-L1 binding polypeptide according to any one of items 1-26, which comprises an amino acid sequence selected from:

vii) (SEQ ID NO: 26)
FN-[*BMod*]-AP;

wherein [BMod] is a PD-L1 binding module as defined in any one of items 20-26; and
viii) an amino acid sequence which has at least 90% identity to a sequence defined by vi).
29. PD-L1 binding polypeptide according to any preceding item, which comprises an amino acid sequence selected from:

SEQ ID NO: 31
ADNNFNK-[*BM*]-DPSQSANLLSEAKKLNESQAPK;

SEQ ID NO: 32
ADNKFNK-[*BM*]-DPSQSANLLAEAKKLNDAQAPK;

SEQ ID NO: 33
ADNKFNK-[*BM*]-DPSVSKEILAEAKKLNDAQAPK;

SEQ ID NO: 34
ADAQQNNFNK-[*BM*]-DPSQSTNVLGEAKKLNESQAPK;

SEQ ID NO: 35
AQHDE-[*BM*]-DPSQSANVLGEAQKLNDSQAPK;

SEQ ID NO: 36
VDNKFNK-[*BM*]-DPSQSANLLAEAKKLNDAQAPK;

SEQ ID NO: 37
AEAKYAK-[*BM*]-DPSESSELLSEAKKLNKSQAPK;

SEQ ID NO: 38
VDAKYAK-[*BM*]-DPSQSSELLAEAKKLNDAQAPK;

SEQ ID NO: 39
VDAKYAK-[*BM*]-DPSQSSELLAEAKKLNDSQAPK;

SEQ ID NO: 40
AEAKYAK-[*BM*]-DPSQSSELLSEAKKLNDSQAPK;

SEQ ID NO: 41
AEAKYAK-[*BM*]-DPSQSSELLSEAKKLNDSQAP;

SEQ ID NO: 42
AEAKFAK-[*BM*]-DPSQSSELLSEAKKLNDSQAPK;

SEQ ID NO: 43
AEAKFAK-[*BM*]-DPSQSSELLSEAKKLNDSQAP;

SEQ ID NO: 44
AEAKYAK-[*BM*]-DPSQSSELLAEAKKLNDAQAPK;

SEQ ID NO: 45
AEAKYAK-[*BM*]-DPSQSSELLSEAKKLSESQAPK;

SEQ ID NO: 46
AEAKYAK-[*BM*]-DPSQSSELLSEAKKLSESQAP;

SEQ ID NO: 47
AEAKFAK-[*BM*]-DPSQSSELLSEAKKLSESQAPK;

SEQ ID NO: 48
AEAKFAK-[*BM*]-DPSQSSELLSEAKKLSESQAP;

SEQ ID NO: 49
AEAKYAK-[*BM*]-DPSQSSELLAEAKKLSEAQAPK;

-continued

```
                                          SEQ ID NO: 50
AEAKYAK-[BM]-QPEQSSELLSEAKKLSESQAPK;

SEQ ID NO: 51
AEAKYAK-[BM]-DPSQSSELLSEAKKLESSQAPK;

SEQ ID NO: 52
AEAKYAK-[BM]-DPSQSSELLSEAKKLESSQAP;

SEQ ID NO: 53
AEAKYAK-[BM]-DPSQSSELLAEAKKLESAQAPK;

SEQ ID NO: 54
AEAKYAK-[BM]-QPEQSSELLSEAKKLESSQAPK;

SEQ ID NO: 55
AEAKYAK-[BM]-DPSQSSELLSEAKKLSDSQAPK;

SEQ ID NO: 56
AEAKYAK-[BM]-DPSQSSELLSEAKKLSDSQAP;

SEQ ID NO: 57
AEAKYAK-[BM]-DPSQSSELLAEAKKLSDSQAPK;

SEQ ID NO: 58
AEAKYAK-[BM]-DPSQSSELLAEAKKLSDAQAPK;

SEQ ID NO: 59
AEAKYAK-[BM]-QPEQSSELLSEAKKLSDSQAPK;

SEQ ID NO: 60
VDAKYAK-[BM]-DPSQSSELLSEAKKLNDSQAPK;

SEQ ID NO: 61
VDAKYAK-[BM]-DPSQSSELLAEAKKLNDAQAPK;

SEQ ID NO: 62
VDAKYAK-[BM]-DPSQSSELLSEAKKLSESQAPK;

SEQ ID NO: 63
VDAKYAK-[BM]-DPSQSSELLAEAKKLSEAQAPK;

SEQ ID NO: 64
VDAKYAK-[BM]-QPEQSSELLSEAKKLSESQAPK;

SEQ ID NO: 65
VDAKYAK-[BM]-DPSQSSELLSEAKKLESSQAPK;

SEQ ID NO: 66
VDAKYAK-[BM]-DPSQSSELLAEAKKLESAQAPK;

SEQ ID NO: 67
VDAKYAK-[BM]-QPEQSSELLSEAKKLESSQAPK;

SEQ ID NO: 68
VDAKYAK-[BM]-DPSQSSELLSEAKKLSDSQAPK;

SEQ ID NO: 69
VDAKYAK-[BM]-DPSQSSELLAEAKKLSDSQAPK;

SEQ ID NO: 70
VDAKYAK-[BM]-DPSQSSELLAEAKKLSDAQAPK;

SEQ ID NO: 71
VDAKYAK-[BM]-QPEQSSELLSEAKKLSDSQAPK;

SEQ ID NO: 72
VDAKYAK-[BM]-DPSQSSELLAEAKKLNKAQAPK;

SEQ ID NO: 73
AEAKYAK-[BM]-DPSQSSELLAEAKKLNKAQAPK;
and

SEQ ID NO: 74
ADAKYAK-[BM]-DPSQSSELLSEAKKLNDSQAPK;
``` wherein [BM] is a PD-L1 binding motif as defined in any one of items 1-15.

30. PD-L1 binding polypeptide according to any one of items 1-29, which comprises an amino acid sequence selected from:

xvii)
```
                                          SEQ ID NO: 60
VDAKYAK-[BM]-DPSQSSELLSEAKKLNDSQAPK;
``` wherein [BM] is a PD-L1 binding motif as defined in any one of items 1-15; and xviii) an amino acid sequence which has at least 89% identity to the sequence defined in xvii).

31. PD-L1 binding polypeptide according to any one of items 1-29, which comprises an amino acid sequence selected from:

xix)
```
                                          SEQ ID NO: 47
AEAKFAK-[BM]-DPSQSSELLSEAKKLSESQAPK;
``` wherein [BM] is a PD-L1 binding motif as defined in any one of items 1-15; and xx) an amino acid sequence which has at least 89% identity to the sequence defined in xix).

32. PD-L1 binding polypeptide according to any one of items 1-29, which comprises an amino acid sequence selected from:

xxi)
```
                                          SEQ ID NO: 40
AEAKYAK-[BM]-DPSQSSELLSEAKKLNDSQAPK;
``` wherein [BM] is a PD-L1 binding motif as defined in any one of items 1-15; and xxii) an amino acid sequence which has at least 89% identity to the sequence defined in xxi).

33. PD-L1 binding polypeptide according to any one of items 1-29, which comprises an amino acid sequence selected from:

xxiii)
```
                                          SEQ ID NO: 42
AEAKFAK-[BM]-DPSQSSELLSEAKKLNDSQAPK;
``` wherein [BM] is a PD-L1 binding motif as defined in any one of items 1-15; and xxiv) an amino acid sequence which has at least 89% identity to the sequence defined in xxiii).

34. PD-L1 binding polypeptide according to any preceding item, wherein sequence xvii) or xxi) corresponds to the sequence from position 1 to position 58 in a sequence selected from the group consisting of SEQ ID NO:1-5.

35. PD-L1 binding polypeptide according to item 34 wherein xvii) or xxi) corresponds to the sequence from position 1 to position 58 in a sequence selected from the group consisting of SEQ ID NO:1, 4 and 5.

36. PD-L1 binding polypeptide according to item 34 or 35, wherein sequence xvii) or xxi) corresponds to the sequence from position 1 to position 58 in a sequence selected from the group consisting of SEQ ID NO:1 and 5.

37. PD-L1 binding polypeptide according to any one of items 34-36, wherein sequence xvii) corresponds to the sequence from position 1 to position 58 in SEQ ID NO:1.

38. PD-L1 binding polypeptide according to item 34, wherein sequence xvii) corresponds to the sequence from position 1 to position 58 in SEQ ID NO:2.

39. PD-L1 binding polypeptide according to item 34, wherein sequence xvii) corresponds to the sequence from position 1 to position 58 in SEQ ID NO:3.
40. PD-L1 binding polypeptide according to item 34, wherein sequence xvii) corresponds to the sequence from position 1 to position 58 in SEQ ID NO:4.
41. PD-L1 binding polypeptide according to any one of items 34-36, wherein sequence xxi) corresponds to the sequence from position 1 to position 58 in SEQ ID NO:5
42. PD-L1 binding polypeptide according to any preceding item, which is capable of blocking the PD-L1 dependent signaling.
43. PD-L1 binding polypeptide according to item 42, wherein the half maximal inhibitory concentration (IC50) of the blocking is at most $1 \times 10^{-8}$ M, such as at most $7 \times 10^{-9}$ M, such as at most $5 \times 10^{-9}$ M.
44. PD-L1 binding polypeptide according to item 42 or 43, which is capable of blocking the interaction of PD-L1 with PD-1.
45. PD-L1 binding polypeptide according to any preceding item which is capable of binding to PD-L1 such that the $K_D$ value of the interaction is at most $1 \times 10^{-6}$ M, such as at most $1 \times 10^{-7}$ M, such as at most $5 \times 10^{-8}$ M, such as at most $1 \times 10^{-9}$ M.
46. PD-L1 binding polypeptide according to any preceding item which is capable of binding to PD-L1 such that the EC50 value of the interaction is at most $1 \times 10^{-9}$ M, such as at most $5 \times 10^{-10}$ M, such as at most $2 \times 10^{-10}$ M.
47. PD-L1 binding polypeptide according to any one of items 42-46, wherein said PD-L1 is human PD-L1.
48. PD-L1 binding polypeptide according to any preceding item which comprises additional amino acids at the C-terminal and/or N-terminal end.
49. PD-L1 binding polypeptide according to item 48, wherein said additional amino acid(s) improve(s) production, purification, stabilization in vivo or in vitro, coupling or detection of the polypeptide.
50. PD-L1 binding polypeptide according to any preceding item in multimeric form, comprising at least two PD-L1 binding polypeptide monomer units, whose amino acid sequences may be the same or different
51. PD-L1 binding polypeptide according to item 50, wherein said PD-L1 binding polypeptide monomer units are covalently coupled together.
52. PD-L1 binding polypeptide according to item 51, wherein the PD-L1 binding polypeptide monomer units are expressed as a fusion protein.
53. PD-L1 binding polypeptide according to any one of items 50-52, in dimeric form.
54. Fusion protein or conjugate comprising
  a first moiety consisting of a PD-L1 binding polypeptide according to any preceding item; and
  a second moiety consisting of a polypeptide having a desired biological activity.
55. Fusion protein or conjugate according to item 54, wherein said desired biological activity is a therapeutic activity.
56. Fusion protein or conjugate according to item 54, wherein said desired biological activity is a binding activity.
57. Fusion protein or conjugate according to item 54, wherein said desired biological activity is an enzymatic activity.
58. Fusion protein or conjugate according to item 56, wherein said binding activity is albumin binding activity which increases in vivo half-life of the fusion protein or conjugate.
59. Fusion protein or conjugate according to item 58, wherein said second moiety comprises the albumin binding domain of streptococcal protein G or a derivative thereof.
60. Fusion protein or conjugate according to item 56, wherein said binding activity acts to block a biological activity.
61. Fusion protein or conjugate according to item 55, wherein the second moiety is a therapeutically active polypeptide.
62. Fusion protein or conjugate according to item 61, wherein the second moiety is an immune response modifying agent.
63. Fusion protein or conjugate according to item 61, wherein the second moiety is an anti-cancer agent.
64. Fusion protein or conjugate according to any one of items 54-57 and 60-63, wherein the second moiety is selected from the group consisting of human endogenous enzymes, hormones, growth factors, chemokines, cytokines and lymphokines.
65. Fusion protein according to any one of items 54-64, wherein the second further comprising a linker.
66. Complex comprising at least one PD-L1 binding polypeptide according to any one of the preceding items and at least one antibody or an antigen binding fragment thereof.
67. Complex according to item 66, wherein said at least one antibody or antigen binding fragment thereof is selected from the group consisting of full-length antibodies, Fab fragments, Fab' fragments, F(ab)$_2$ fragments, Fc fragments, Fv fragments, single chain Fv (scFv) fragments, (scFv)$_2$ and domain antibodies.
68. Complex according to item 67, wherein said at least one antibody or antigen binding fragment thereof is selected from the group consisting of full-length antibodies, Fab fragments and scFv fragments.
69. Complex according to item 67, wherein said at least one antibody or antigen binding fragment thereof is a full-length antibody.
70. Complex according to any one of items 67-69, wherein said antibody or antigen binding fragment thereof is a monoclonal antibody or an antigen binding fragment thereof.
71. Complex according to any one of items 66-70, wherein said antibody or antigen binding fragment thereof is selected from the group consisting of human antibodies, humanized antibodies and chimeric antibodies, and antigen binding fragments thereof.
72. Complex according to item 71, wherein said antibody or antigen binding fragment thereof is a human or humanized antibody, or an antigen binding fragment thereof.
73. Complex according to any one of items 66-72, wherein said PD-L1 binding polypeptide is attached at either the C-terminus or the N-terminus of the heavy chain or the light chain of said antibody or antigen binding fragment thereof.
74. Complex according to any one of items 66-73, further comprising a linker.
75. Complex according to any of items 66-74, wherein said antibody or antigen binding fragment thereof has affinity for an antigen, for example an antigen associated with an infection disease, or an antigen associated with cancer.
76. Fusion protein or conjugate according to any one of items 54-65 or complex according to any one of items 66-75, herein said second moiety or antibody or antigen binding fragment thereof is selected from the group consisting of inhibitors of PD-1, CTLA-4, T-cel immunoglobulin and mucin containing protein-3 (TIM-3), galectin-9 (GAL-9), lymphocyte activation gene-3 (LAG-3), PD-L2, B7 homolog 3 (B7-H3), B7 homolog 4 (B7-H4), V-domain Ig suppressor of T-cell activation (VISTA), carcinoembryonic antigen-related cell adhesion molecule 1 (CEACAMI), B and T lymphocyte attenuator (BTLA), colony stimulating factor 1 receptor (CSF1R), herpes virus entry mediator (HVEM), killer immunoglobulin receptor (KIR), adenosine, adenosine A2a receptor (A2aR), CD200-CD200R and T cell Ig and ITIM domain.

77. Fusion protein, conjugate or complex according to item 76, wherein said second moiety, antibody or antigen binding fragment thereof is an inhibitor of PD-1, such an inhibitor selected from the group consisting of nivolumab, pidilizumab, BMS 936559, MPDL328OA and pembrolizumab, such as pembrolizumab.

78. Fusion protein, conjugate or complex according to item 76, wherein said second moiety, antibody or antigen binding fragment thereof is an inhibitor of CTLA-4, such an inhibitor selected from the group consisting of belatacept, abatacept and ipilimumab, such as ipilimumab.

79. Fusion protein or conjugate according to any one of items 54-65 or complex according to any one of items 66-75, wherein said second moiety or antibody or antigen binding fragment thereof is selected from the group consisting of agonists of CD134, CD40, 4-1 BB and glucocorticoid-induced TNFR-related protein (GITR).

80. PD-L1 binding polypeptide, fusion protein, conjugate or complex according to any one of items 1-79, further comprising a label.

81. PD-L1 binding polypeptide, fusion protein, conjugate or complex according to item 80, wherein said label is selected from the group consisting of fluorescent dyes and metals, chromophoric dyes, chemiluminescent compounds and bioluminescent proteins, enzymes, radionuclides, radioactive particles and pretargeting recognition tags.

82. PD-L1 binding polypeptide, fusion protein, conjugate or complex according to item 81, comprising a chelating environment provided by a polyaminopolycarboxylate chelator conjugated to the PD-L1 binding polypeptide via a thiol group of a cysteine residue or an amine group of a lysine residue.

83. PD-L1 binding polypeptide, fusion protein, conjugate or complex according to item 80, which comprises a pretargeting recognition tag forming part of a complementary pair of pretargeting moieties, for example selected from stept (avidin)/biotin, oligonucleotide/complementary oligonucleotide such as DNA/complementary DNA, RNA/complementary RNA, phosphorothioate nucleic acid/complementary phosphorothioate nucleic acid and peptide nucleic acid/complementary peptide nucleic acid and morpholinos/complementary morpholinos.

84. PD-L1 binding polypeptide, fusion protein, conjugate or complex according to item 83, wherein said pretargeting recognition tag is a peptide nucleic acid tag.

85. PD-L1 binding polypeptide, fusion protein, conjugate or complex according to any one of item 84, wherein said pretargeting recognition tag is a 10-20-mer peptide nucleic acid sequence, such as a 15-mer peptide nucleic acid sequence.

86. A polynucleotide encoding a polypeptide according to any one of items 1-79.

87. Expression vector comprising a polynucleotide according to item 86.

88. Host cell comprising an expression vector according to item 87.

89. Method of producing a polypeptide according to any one of items 1-79, comprising
culturing a host cell according to item 87 under conditions permissive of expression of said polypeptide from said expression vector, and
isolating said polypeptide.

90. Composition comprising a PD-L1 binding polypeptide, fusion protein, conjugate or complex according to any one of items 1-85 and at least one pharmaceutically acceptable excipient or carrier.

91. Composition according to item 90, further comprising at least one additional active agent, such as an agent selected from an immune response modifying agent and an anticancer agent.

92. PD-L1 binding polypeptide, fusion protein, conjugate or complex according to any one of items 1-85 or a composition according to any one of items 90-91 for oral, topical, intravenous, intraperitoneal, subcutaneous, pulmonary, transdermal, intramuscular, intranasal, buccal, sublingual or suppository administration, such as for topical administration.

93. PD-L1 binding polypeptide, fusion protein, conjugate or complex according to any one of items 1-85 or a composition according to any one of items 90-91 for use as a medicament, a diagnostic agent and/or a prognostic agent.

94. PD-L1 binding polypeptide, fusion protein, conjugate, complex or composition according to item 93 for use as a medicament.

95. PD-L1 binding polypeptide, fusion protein, conjugate, complex or composition according to item 93 for use as a diagnostic agent and/or a prognostic agent.

96. PD-L1 binding polypeptide, fusion protein, conjugate, complex or composition for use according to item 94, wherein said polypeptide, fusion protein, conjugate or composition modulates PD-L1 function in vivo.

97. PD-L1 binding polypeptide, fusion protein, conjugate, complex or composition for use according to any one of items 94-96, in the treatment, prognosis or diagnosis of a PD-L1 related disorder.

98. PD-L1 binding polypeptide, fusion protein, conjugate, complex or composition for use according to item 97, wherein said PD-L1 related disorder is selected from the group consisting of infectious diseases and cancers.

99. PD-L1 binding polypeptide, fusion protein, conjugate, complex or composition for use according to item 98, wherein said PD-L1 related disorder is an infectious disease, such as a chronic viral infection, such as a chronic viral infection selected from the group consisting of such as human immunodeficiency virus (HIV), hepatitis B virus (HBV) and hepatitis C virus (HCV).

100. PD-L1 binding polypeptide, fusion protein, conjugate, complex or composition for use according to item 98, wherein said PD-L1 related disorder is cancer.

101. PD-L1 binding polypeptide, fusion protein, conjugate, complex or composition for use according to item 100, wherein said cancer is
a cancer selected from the group consisting of
cancers manifesting solid tumors, for example selected from the group consisting of skin cancer, such as melanoma and nonmelanoma skin cancer (NMSC); lung cancers, such as small cell lung cancer, non-small cell lung cancer (NSCLC); head and neck cancer; renal cell carcinoma (RCC); bladder cancer; breast cancer; colorectal cancer; gastric cancer; ovarian cancer; pancreatic cancer; prostate cancer; glioma; glioblastoma; liver carcinoma; gallbladder cancer; thyroid cancer; bone cancer; cervical cancer; uterine cancer; vulval cancer endometrial cancer; testicular cancer; kidney cancer; esophageal carcinoma; brain/CNS cancers;

neuronal cancers; mesothelioma; sarcomas; small bowel adenocarcinoma; and pediatric malignancies; and cancers manifesting non-solid tumors, for example leukaemia, acute myeloid leukaemia, acute lymphoblastic leukaemia and multiple myeloma.

102. PD-L1 binding polypeptide, fusion protein, conjugate, complex or composition for use according to item 101, wherein said cancer is selected from the group consisting of melanoma, NSCLC, head and neck cancer, RCC, bladder cancer, breast cancer, colorectal cancer, gastric cancer, ovarian cancer, pancreatic cancer and prostate cancer, such as a cancer is selected from the group consisting of melanoma, NSCLC, head and neck cancer, RCC and bladder cancer.

103. Method of treatment of a PD-L1 related disorder, comprising administering to a subject in need thereof an effective amount of a PD-L1 binding polypeptide, fusion protein, conjugate or complex according to any one of items 1-85 or a composition according to any one of items 90-91.

104. Method according to item 103, wherein said PD-L1 related disorder is selected from the group consisting of infectious disease and cancer.

105. Method according to item 104, wherein said PD-L1 related disorder is an infectious disease, such as a chronic viral infection, such as a chronic viral infection selected from the group consisting of such as human immunodeficiency virus (HIV), hepatitis B virus (HBV) and hepatitis C virus (HCV).

106. Method according to item 104, wherein said PD-L1 related disorder is cancer, such as a cancer selected from the group consisting of:

cancers manifesting solid tumors, for example selected from the group consisting of skin cancer, such as melanoma and nonmelanoma skin cancer (NMSC); lung cancers, such as small cell lung cancer, non-small cell lung cancer (NSCLC); head and neck cancer; renal cell carcinoma (RCC); bladder cancer; breast cancer; colorectal cancer; gastric cancer; ovarian cancer; pancreatic cancer; prostate cancer; glioma; glioblastoma; liver carcinoma; gallbladder cancer; thyroid cancer; bone cancer; cervical cancer; uterine cancer; vulval cancer endometrial cancer; testicular cancer; kidney cancer; esophageal carcinoma; brain/CNS cancers; neuronal cancers; mesothelioma; sarcomas; small bowel adenocarcinoma; and pediatric malignancies; and cancers manifesting non-solid tumors, for example leukaemia, acute myeloid leukaemia, acute lymphoblastic leukaemia and multiple myeloma.

107. Method according to item 106, in which said cancer is selected from the group consisting of melanoma, NSCLC, head and neck cancer, RCC, bladder cancer, breast cancer, colorectal cancer, gastric cancer, ovarian cancer, pancreatic cancer and prostate cancer, such as selected from the group consisting of melanoma, NSCLC, head and neck cancer, RCC and bladder cancer.

108. Method according to any one of items 106-107, comprising the steps of:

contacting the subject with a PD-L1 binding polypeptide, fusion protein, conjugate or complex according to any one of items 83-85 comprising a pretargeting recognition tag, or with a composition comprising such a PD-L1 binding polypeptide, fusion protein, conjugate or complex, and contacting the subject with a complementary pretargeting moiety, comprising a radionuclide.

109. Method of detecting PD-L1, comprising providing a sample suspected to contain PD-L1, contacting said sample with a PD-L1 binding polypeptide, fusion protein, conjugate or complex according to any one of items 1-85 or a composition according to any one of items 90-91, and detecting the binding of the PD-L1 binding polypeptide, fusion protein, conjugate, complex or composition to indicate the presence of PD-L1 in the sample.

110. Method for determining the presence PD-L1 in a subject, comprising the steps of:

a) contacting the subject, or a sample isolated from the subject, with a PD-L1 binding polypeptide, fusion protein, conjugate or complex according to any one of items 1-85 or a composition according to any one of items 90-91, and b) obtaining a value corresponding to the amount of the PD-L1 binding polypeptide, fusion protein, conjugate or composition that has bound in said subject or to said sample.

111. Method according to item 110, in which said PD-L1 binding polypeptide, fusion protein, conjugate or complex is according to any one of items 83-85, or said composition comprises such a PD-L1 binding polypeptide, fusion protein, conjugate or complex, and step a) further comprises contacting the subject with a complementary pretargeting moiety labeled with a detectable label, such as a radionuclide label.

112. Method according to item 110 or 111, further comprising a step of comparing said value to a reference.

113. Method according to any one of items 103-112, wherein said subject is a mammalian subject, such as a human subject.

114. Method according to any one of items 109-112, wherein the method is performed in vivo.

115. Method according to item 114, which is a method for medical imaging in which step a) comprises the systemic administration of said PD-L1 binding polypeptide, fusion protein, conjugate, complex or composition to a mammalian subject;

said PD-L1 binding polypeptide, fusion protein, conjugate, complex, composition or pretargeting moiety comprises a radionuclide label suitable for medical imaging; and step b) comprises obtaining one or more images of at least a part of the subjects body using a medical imaging instrument, said image(s) indicating the presence of the radionuclide inside the body.

The invention claimed is:

1. A Programmed Death Ligand 1 (PD-L1) binding polypeptide comprising a PD-L1 binding motif (BM), wherein the PD-L1 binding motif consists of an amino acid sequence selected from:

i)
(SEQ ID NO: 23)
$ERTX_4AX_6WEIX_{10}X_{11}LPNLX_{16}X_{17}X_{18}QX_{20}GAFIX_{25}X_{26}LHD$ wherein, independently from each other, $X_4$ is selected from I, M, V and W;

$X_6$ is selected from T and V;

$X_{10}$ is selected from M and V;

$X_{11}$ is selected from D and Q;

$X_{16}$ is selected from N and T;

$X_{17}$ is selected from A and S;

$X_{18}$ is selected from G, R and W;

$X_{20}$ is selected from K and R;

$X_{25}$ is selected from D, N and W; and $X_{26}$ is selected from K and S;

and ii) an amino acid sequence which has at least 96% identity to the sequence defined in i).

2. The PD-L1 binding polypeptide according to claim 1, wherein sequence i) corresponds to the sequence from position 8 to position 36 in a sequence selected from the group consisting of SEQ ID NO: 1-4.

3. The PD-L1 binding polypeptide according to claim 1, wherein said PD-L1 binding motif forms part of a three-helix bundle protein domain.

4. The PD-L1 binding polypeptide according to claim 1 comprising a binding module (BMod), wherein the amino acid sequence of the binding module is selected from:

iii) (SEQ ID NO: 24)
K-[*BM*]-$DPSQSX_aX_bLLX_c$ $EAKKLX_dX_eX_fQ$;

wherein

[BM] is the PD-L1 binding motif;

$X_a$ is selected from A and S;

$X_b$ is selected from N and E;

$X_c$ is selected from A, S and C;

$X_d$ is selected from E, N and S;

$X_e$ is selected from D, E and S; and $X_f$ is selected from A and S; and iv) an amino acid sequence which has at least 97% identity to a sequence defined in iii).

5. The PD-L1 binding polypeptide according to claim 1 comprising an amino acid sequence selected from:

xvii) SEQ ID NO: 60
VDAKYAK-[*BM*]-DPSQSSELLSEAKKLNDSQAPK wherein [BM] is the PD-L1 binding motif; and xviii) an amino acid sequence which has at least 98% identity to the sequence defined in xvii).

6. The PD-L1 binding polypeptide according to claim 1 comprising an amino acid sequence selected from:

xxi) SEQ ID NO: 40
AEAKYAK-[*BM*]-DPSQSSELLSEAKKLNDSQAPK;

wherein [BM] is the PD-L1 binding motif; and xxii) an amino acid sequence which has at least 98% identity to the sequence defined in xxi).

7. The PD-L1 binding polypeptide according to claim 5 or 6, wherein sequence xvii) or xxi) corresponds to the sequence from position 1 to position 58 in a sequence selected from the group consisting of SEQ ID NO: 1-5.

8. The PD-L1 binding polypeptide according to claim 1 which is capable of binding to PD-L1 such that the $K_D$ value of the interaction is at most $1\times10^{-6}$ M.

9. A Fusion protein or conjugate comprising
a first moiety consisting of a PD-L1 binding polypeptide according to claim 1; and
a second moiety consisting of a polypeptide having a desired biological activity.

10. A Complex comprising at least one PD-L1 binding polypeptide according to claim 1 and at least one antibody or an antigen binding fragment thereof.

11. The PD-L1 binding polypeptide according to claim 1, further comprising a label.

12. A polynucleotide encoding a polypeptide according to claim 1.

13. The Composition comprising a PD-L1 binding polypeptide, according to claim 1 and at least one pharmaceutically acceptable excipient or carrier.

14. The PD-L1 binding polypeptide according to claim 1, wherein sequence i) corresponds to the sequence from position 8 to position 36 in a sequence selected from the group consisting of SEQ ID NO: 1 or 4.

15. The PD-L1 binding polypeptide according to claim 7, wherein sequence xvii) or xxi) corresponds to the sequence from position 1 to position 58 in a sequence selected from the group consisting of SEQ ID NO: 1, 4 and 5.

16. The PD-L1 binding polypeptide according to claim 8 which is capable of binding to PD-L1 such that the $K_D$ value of the interaction is at most $1\times10^{-7}$ M.

17. The PD-L1 binding polypeptide according to claim 8 which is capable of binding to PD-L1 such that the $K_D$ value of the interaction is at most $1\times10^{-8}$ M.

18. The PD-L1 binding polypeptide according to claim 8 which is capable of binding to PD-L1 such that the $K_D$ value of the interaction is at most $1\times10^{-9}$ M.

19. The PD-L1 binding polypeptide according to claim 11, wherein said label is selected from the group consisting of fluorescent dyes and metals, chromophoric dyes, chemiluminescent compounds and bioluminescent proteins, enzymes, radionuclides, radioactive particles and pretargeting recognition tags.

20. A method of treating a PD-L1 related disorder, comprising:
administering to a subject in need thereof an effective amount of a PD-L1 binding polypeptide according to claim 1.

21. The method according to claim 20, wherein said PD-L1 related disorder is selected from the group consisting of infectious disease and cancer.

22. The method according to claim 21, wherein the infectious disease is a chronic viral infection selected from the group consisting of human immunodeficiency virus (HIV), hepatitis B virus (HBV) and hepatitis C virus (HCV).

23. The method according to claim 21, wherein the cancer is selected from the group consisting of melanoma and nonmelanoma skin cancer (NMSC); lung cancers, head and neck cancer; renal cell carcinoma (RCC); bladder cancer; breast cancer; colorectal cancer; gastric cancer; ovarian cancer; pancreatic cancer; prostate cancer; glioma; glioblastoma; liver carcinoma; gallbladder cancer; thyroid cancer; bone cancer; cervical cancer; uterine cancer; vulval cancer; endometrial cancer; testicular cancer; kidney cancer; esophageal carcinoma; brain/CNS cancers; neuronal cancers; mesothelioma; sarcomas; small bowel adenocarcinoma; and pediatric malignancies; leukaemia, acute myeloid leukaemia, acute lymphoblastic leukaemia and multiple myeloma.

24. A method of detecting PD-L1 comprising
contacting a sample suspected to contain PD-L1 with a PD-L1 binding polypeptide according to claim 1, and
detecting binding of the PD-L1 binding polypeptide to indicate the presence of PD-L1 in the sample.

25. A method for medical imaging in a mammalian subject comprising
administering a PD-L1 binding polypeptide according to claim 1 systemically to a mammalian subject, wherein the PD-L1 binding polypeptide comprises a label suitable for medical imaging; and
obtaining one or more images of at least a part of the mammalian subject's body using a medical imaging instrument, said image(s) indicating the presence of the label inside the body.

* * * * *